US009440077B2

(12) United States Patent
Popovic et al.

(10) Patent No.: US 9,440,077 B2
(45) Date of Patent: *Sep. 13, 2016

(54) FUNCTIONAL ELECTRICAL STIMULATION DEVICE AND SYSTEM, AND USE THEREOF

(71) Applicant: University Health Network, Toronto (CA)

(72) Inventors: Milos R. Popovic, Mississauga (CA); Massimo Tarulli, Toronto (CA); Aleksandar Prodic, Toronto (CA); Peter Lehn, Toronto (CA)

(73) Assignee: University Health Network, Toronto (CA)

(*) Notice: Subject to any disclaimer, the term of this patent is extended or adjusted under 35 U.S.C. 154(b) by 0 days.

This patent is subject to a terminal disclaimer.

(21) Appl. No.: 14/500,749

(22) Filed: Sep. 29, 2014

(65) Prior Publication Data

US 2015/0039051 A1 Feb. 5, 2015

Related U.S. Application Data

(63) Continuation of application No. 13/701,722, filed as application No. PCT/CA2011/000637 on Jun. 2, 2011, now Pat. No. 8,880,178.

(60) Provisional application No. 61/351,715, filed on Jun. 4, 2010.

(51) Int. Cl.
*A61N 1/36* (2006.01)
*H03K 3/78* (2006.01)
*A61N 1/04* (2006.01)

(52) U.S. Cl.
CPC ......... *A61N 1/36125* (2013.01); *A61N 1/0476* (2013.01); *A61N 1/36003* (2013.01);
(Continued)

(58) Field of Classification Search
CPC .............. A61N 1/36125; A61N 1/36067; A61N 1/36003; A61N 1/36167
See application file for complete search history.

(56) References Cited

U.S. PATENT DOCUMENTS 4,580,569 A 4/1986 Petrofsky
4,996,987 A 3/1991 Petrofsky
(Continued)

FOREIGN PATENT DOCUMENTS

EP 1352673 10/2003

OTHER PUBLICATIONS

Ghovanloo et al., "A Wireless Implantable Multichannel Microstimulating System-on-a-Chip with Modular Architecture," IEEE Transactions on Neural Systems and Rehabilitation Engineering (2007), 15(3):449-457.
(Continued)

*Primary Examiner* — Catherine Voorhees
(74) *Attorney, Agent, or Firm* — Bret E. Field; Bozicevic, Field & Francis LLP

(57) ABSTRACT

A functional electrical stimulation (FES) device and system. In one embodiment, sequential bipolar pulse stimulation may be provided to an area of a living body via one or more electrode leads applied to the area via a FES device comprising a current pulse generating circuit comprising output nodes for operative coupling to the one or more electrode leads, and configured for operative coupling to a voltage supply. The current pulse generating circuit generally comprises positive and negative stimulation paths drawing from the voltage supply to respectively apply positive and negative currents through the area via the one or more electrode leads. In one example, the stimulation paths comprise respective capacitive elements, a capacitance ratio of which dictating, at least in part, an amplitude ratio of the positive and negative currents, wherein periodic alternative activation of the stimulation paths provides the sequential bipolar pulse stimulation.

18 Claims, 36 Drawing Sheets

(52) U.S. Cl.
CPC ....... *A61N1/36014* (2013.01); *A61N 1/36067* (2013.01); *A61N 1/36167* (2013.01); *H03K 3/78* (2013.01); *A61N 1/3615* (2013.01); *A61N 1/36103* (2013.01); *A61N 1/36171* (2013.01)

(56) References Cited

U.S. PATENT DOCUMENTS

| | | | |
|---|---|---|---|
| 6,029,090 A | 2/2000 | Herbst | |
| 6,290,661 B1 | 9/2001 | Cutler et al. | |
| 6,871,092 B2 | 3/2005 | Piccone | |
| 6,988,005 B2 | 1/2006 | McGraw et al. | |
| 7,450,987 B2 * | 11/2008 | Varrichio | H02M 3/07 607/2 |
| 8,880,178 B2 * | 11/2014 | Popovic | A61N 1/36003 607/148 |
| 2004/0015203 A1 * | 1/2004 | McGraw | A61N 1/326 607/48 |
| 2008/0058878 A1 | 3/2008 | King | |
| 2009/0088812 A1 * | 4/2009 | Wulfman | A61N 1/056 607/9 |
| 2011/0077698 A1 * | 3/2011 | Tsampazis | A61N 1/08 607/2 |
| 2011/0276107 A1 | 11/2011 | Simon et al. | |

OTHER PUBLICATIONS

Gong et al., "A CMOS Multichannel Electrical Stimulation Prototype System," Int. J. Circ. Theor. Appl. (2013), 41:238-258.

Gong et al., "An Efficient Micro-Stimulator Array Using Unitary-Size DAC with Adiabatic Baseband Scheme," IEEE (2006), pp. 29-32.

Gong et al., "Prototype Neural Semicircular Canal Prosthesis Using Patterned Electrical Stimulation," Annals of Biomedical Engineering (2000), 28:572-581.

Gracanin, "Functional Electrical Stimulation in External Control of Motor Activity and Movements of Paralysed Extremities," Int. Rehabil. Med. (1984), 6:25-30.

Gudnason et al, "A Chip for an Implantable Neural Stimulator," Analog Integrated Circuits and Signal Processing (1999), 22:81-89.

Gudnason et al., "A Distributed Transducer System for Functional Electrical Stimulation," IEEE (2001), pp. 397-400.

Gudnason et al., "An Implantable Mixed Analog/Digital Neural Stimulator Circuit", IEEE (1999), pp. V-375-V-378.

Guiraud et al., "Original Electronic Design to Perform Epimysial and Neural Stimulation in Paraplegia," J. Neural Eng. (2006), 3:276-286.

Guiraud, "Interfacing the Neural System to Restore Deficient Functions: from Theoretical Studies to Neuroprothesis Design," C.R. Biologies (2012), 335:1-8.

Haas et al., "Wireless Implantable Micro-Stimulation Device for High Frequency Bilateral Deep Brain Stimulation in Freely Moving Mice," Journal of Neuroscience Methods (2012), 209: 113-119.

Harnack et al., "Continuous High-Frequency Stimulation in Freely Moving Rats: Development of an Implantable Microstimulation System," Journal of Neuroscience Methods (2008), 167:278-291.

Hart et al., "A Microcontroller System for Investigating the Catch Effect: Functional Electrical Stimulation of the Common Peroneal Nerve," Medical Engineering & Physics (2006), 28:438-448.

Hart et al., "Design and Testing of an Advanced Implantable Neuroprosthesis with Myoelectric Control," IEEE Transactions on Neural Systems and Rehabilitation Engineering (2011), 19(1):45-53.

Hodgins et al., "Healthy Aims: Developing New Medical Implants and Diagnostic Equipment," IEEE (2009), pp. 14-21.

Houdayer et al., "Technical Solutions for Modifying the Cochlear Mini-22 Implantable Stimulator to a Portable FES Device for Paraplegic Standing," Theme 5: Neuromuscular Systems/Biomechanics (1997), pp. 1139-1140.

Hu et al., "A 96-Channel Neural Stimulation System for Driving AIROF Microelectrodes," Proceedings of the 26th Annual International Conference of the IEEE EMBS (Sep. 2004), pp. 4244-4247.

Hu et al., "A Wide Range Charge-Balancing Circuit Using Floating-Gate Transistors," Proceedings of the 29th Annual International Conference of the IEEE EMBS (Aug. 2007), pp. 5695-5698.

Huys et al., "A Novel 16k Micro-Nail CMOS-Chip for in-Vitro Single-Cell Recording, Stimulation and Impedance Measurements," 32nd Annual International Conference of the IEEE EMBS (Aug. 2010), pp. 2276-2279.

Ilic et al., "A Programmable Electronic Stimulator for FES Systems," IEEE Transactions on Rehabilitation Engineering (1994), 2(4):234-239.

Jalilian et al., "Implantable Neural Electrical Stimulator for External Control of Gastrointestinal Motility," Medical Engineering & Physics (2007), 29:238-252.

Jarvis et al., "A Family of Neuromuscular Stimulators with Optical Transcutaneous Control," Journal of Medical Engineering & Technology (1991), 15(2):53-57.

Jaw et al., "Portable Current Stimulator for Transdermal Iontophoretic Drug Delivery," Med. Eng. Phys. (1995), 17 (5):385-386.

Jones et al., "An Advanced Demultiplexing System for Physiological Stimulation," IEEE Transactions on Biomedical Engineering (1997), 44(12):1210-1220.

Kaczmarek et al., "A 16-Channel 8-Parameter Waveform Electrotactile Stimulation System," IEEE Transactions on Biomedical Engineering (1991), 38(10):933-943.

Karcnik et al., "Application of Microprocessor Controlled Multichannel Stimulator to the Rehabilitation of SCI Subjects," Hong Kong Physiotherapy Journal (2000), 18(1):27-32.

Kim, "A 64-Site Multishank CMOS Low-Profile Neural Stimulating Probe," IEEE Journal of Solid-State Circuits (1996), 31(9):1230-1238.

Kouzani et al., "A Low Power Micro Deep Brain Stimulation Device for Murine Preclinical Research," Animal Models, vol. 1, (2013), 9 pages.

Krishnan et al., "On the Cause and Control of Residual Voltage Generated by Electrical Stimulation of Neural Tissue," 34th Annual International Conference of the IEEE EMBS (2012), pp. 3899-3902.

Langlois et al., "High-Power Integrated Stimulator Output Stages with Floating Discharge over a Wide Voltage Range for Nerve Stimulation," IEEE Transactions on Biomedical Circuits and Systems (2010), 4(1):39-48.

Laotaveerungrueng et al., "A High-Voltage, High-Current CMOS Pulse Generator ASIC for Deep Brain Stimulation," 32nd Annual International Conference of the IEEE EMBS (2010), pp. 1519-1522.

Lee et al. "A Biomedical Implantable FES Battery-Powered Micro Stimulator," IEEE Transactions on Biomedical Circuits and Systems (2009), 56(12)2583-2596.

Li et al., "Microelectronics Neural Bridge IC with Voltage Stimulation," 4th International Conference on Biomedical Engineering and Informatics (BMEI), (2011), pp. 1139-1143.

Li et al., "Parylene-Based Integrated Wireless Single-Channel Neurostimulator," Sensors and Actuators A: Physical (2011), 166:193-200.

Liang et al., "A Microcontroller-Based Implantable Neuromuscular Stimulation System with Wireless Power and Data Transmission for Animal Experiments," Journal of the Chinese Institute of Engineers (2003), 26(4):493-501.

Lim et al., "A 16-Channel Neural Stimulator with DAC Sharing Scheme for Visual Prostheses," IEEE (2013), pp. 1873-1876.

Liu et al., "A Fully Integrated Fail-Safe Stimulator Output Stage Dedicated to FES Stimulation," IEEE (2007), pp. 2076-2079.

Liu et al., "A Miniaturized, Power-Efficient Stimulator Output Stage Based on the Bridge Rectifier Circuit," IEEE (2006), pp. 498-501.

Liu et al., "A Neuro-Stimulus Chip with Telemetry Unit for Retinal Prosthetic Device," IEEE Journal of Solid-State Circuits (2000), 35(10):1487-1497.

Liu et al., "A Stimulator ASIC with Capability of Neural Recording during Inter-Phase Delay," IEEE (2011), pp. 215-218.

Liu et al., "A Stimulator Output Stage with Capacitor Reduction and Failure-Checking Techniques," IEEE (2006), pp. 641-644.

(56) References Cited

OTHER PUBLICATIONS

Liu et al., "An Ambient Light Adaptive Subrential Stimulator," IEEE (2009), pp. 240-423.
Liu et al., "An Integrated Implantable Stimulator that is Fail-Safe Without Off-Chip Blocking-Capacitors," IEEE Transactions on Biomedical Circuits and Systems (2008), 2(3):231-244.
Liu et al., "An Integrated Stimulator with DC-Isolation and Fine Current Control for Implanted Nerve Tripoles," IEEE Journal of Solid-State Circuits (2011), 46(7):1701-1714.
Liu et al., "Retinal Prosthesis to Aid the Visually Impaired," IEEE (1999), pp. 364-369.
Liu et al., "Retinal Prosthesis," IEEE International Solid-State Circuits Conference, (2004), 8 pages.
Loeb et al., "BION System for Distributed Neural Prosthetic Interfaces," Medical Engineering & Physics (2001), 23:9-18.
Gloeb et al., "Injectable Microstimulator for Functional Electrical Stimulation," Med. Biol. Eng. Comput (1991), 29(6): NS13-NS19.
Manikopoulos et al., "A Versatile Wide-Range Electrical Heart Stimulator," IEEE Transactions on Biomedical Circuits and Systems (1980), BME-27(7):416-418.
Masdar et al., "Development of Wireless-Based Low-Cost Current Controlled Stimulator for Patients with Spinal Cord Injuries," IEEE EMBS International Conference on Biomedical Engineering and Sciences (Dec. 2012), pp. 493-498.
Sooksood et al., "An Active Approach for Charge Balancing in Functional Electrical Stimulation," IEEE Transactions on Biomedical Circuits and Systems (2010), 4(3):162-170.
Sooksood et al., "An Active Approach for Charge Balancing in Functional Electrical Stimulation," Laboratory for Biomedical Microtechnology (2009), pp. 341-344.
Soulier et al., "A Neural Stimulator Output Stage for Dodecapolar Electrodes," IEEE Computer Society Annual Symposium on VLSI, (2008), pp. 487-490.
Soulier et al., "Advances in Implanted Functional Electrical Stimulation," Presented at the Design & Technology of Integrated Systems in Nanoscale Era (DTIS), (2011), pp. 1-6.
Souquet et al., "From Neuroprosthetics to Implanted FES Control Architecture," International Conference on Intelligent Robots and Systems (2008), pp. 2380-2385.
Stanslaski et al., "Design and Validation of a Fully Implantable, Chronic, Closed-Loop Neuromodulation Device with Concurrent Sensing and Stimulation," IEEE Transactions on Neural Systems and Rehabilitation Engineering (2012), 20(4):410-421.
Strojnik et al., "Multichannel FES System with Distributed Microstimulators," Engineering in Medicine and Biology Society (1992), 4:1352-1353.
Suaning et al., "CMOS Neurostimulation ASIC with 100 Channels, Scaleable Output, and Bidirectional Radio-Frequency Telemetry," IEEE Transactions on Biomedical Engineering (2001), 48(2):248-260.
Tai et al., "Stimulation of Nerve Block by High-Frequency Sinusoidal Electrical Current Based on the Hodgkin-Huxley Model," IEEE Transactions on Neural Systems and Rehabilitation Engineering (2005), 13(3):415-421.
Tang et al., "Multichannel Implantable Stimulation and Telemetry System for Neuromuscular Control," IEEE (1994), pp. 442-443.
Tanghe et al., "A 16-Channel CMOS Neural Stimulating Array," IEEE Journal of Solid-State Circuits (1992), 27 (12):1819-1825.
Techer et al., "New Implantable Stimulator for the FES of Paralyzed Muscles," IEEE (2004), pp. 455-458.
Theogarajan, "A Low-Power Fully Implantable 15-Channel Retinal Stimulator Chip," IEEE Journal of Solid-State Circuits (2008), 43(10):2322-2337.
Thrope et al., "A Computer-Controlled Multichannel Stimulation System for Laboratory Use in Functional Neuromuscular Stimulation," IEEE Transactions on Biomedical Engineering (1985), BME-32(6):363-370.
Tobar et al., "Functional Electrical Stimulation System for Walking Based on Mixed Signal Circuits," IFMBE Proceedings (2013), 33:587-590.
Tran al., "A Prototype 64-Electrode Stimulator in 65 nm CMOS Process Towards a High Density Epi-Retinal Prosthesis," 33rd Annual International Conference of the IEEE EMBS (2011), pp. 6729-6732.
Troyk et al., "An Implantable Neural Stimulator for Intraspinal MicroStimulation," 34th Annual International Conference of the IEEE EMBS (Sep. 2012), pp. 900-903.
Troyk et al., "Development of BionTM Technology for Functional Electrical Stimulation: Bidirectional Telemetry," 2001 Proceedings of the 23rd Annual EMBS International Conference, (Oct. 2001), pp. 1317-1320.
Uranga et al., "An Integrated Implantable Electrical Sacral Root Stimulator for Bladder Control," Special Section on Functional Electrical Stimulation (2002), 5(4):248-247.
Uranga et al., "Electrode-Tissue Impedance Measurement CMOS ASIC for Functional Electrical Stimulation Nueroprostheses," IEEE Transactions on Instrumentation and Measurement (2007), 56(5):2043-2050.
Velloso et al., "A Programmable System of Functional Electrical Stimulation (FES)", Proceedings of the 29th Annual International Conference of the IEEE EMBS, (2007), pp. 2234-2237.
Venkatraman et al., "A System for Neural Recording and Closed-Loop Intracortical Microstimulation in Awake Rodents," IEEE Transactions on Biomedical Engineering (2009), 56(1):15-22.
Wang et al., "An Electrical Muscle Stimulator Based on Functional Electrical Stimulation," Proceedings of the IEEE International Conference on Robotics an Biomimetics (2012), pp. 1906-1911.
Wang et al., "Micro-Stimulator Circuitry Design for Visual Prosthesis Based on Optic Nerve Stimulation in Artificial Vision," IEEE, vol. 4, (2006), 4 pages.
Weiland et al., "Retinal Prosthesis," Annu. Rev. Biomed. Eng. (2005), 7:3601-3401.
Wheeler et al., "Wireless Wearable Controller for Upper-Limb Neuroprosthesis," Journal of Rehabilitation Research & Development (2009), 46(2):243-256.
Williams et al., "An Energy-Efficient, Dynamic Voltage Scaling Neural Stimulator for a Proprioceptive Prosthesis," IEEE (2012), pp. 1091-1094.
Winter et al., "A Stimulator with Wireless Power and Signal Transmission for Implantation in Animal Experiments and Other Applications," Journal of Neuroscience Methods (1998), 79: 79-85.
Wong et al., "A Very Low-Power CMOS Mixed-Signal IC for Implantable Pacemaker Applications," IEEE International Solid-State Circuits Conference, (2004), 10 pages.
Wongsarnpigoon et al., "Efficiency Analysis of Waveform Shape for Electrical Excitation of Nerve Fibers," IEEE Transactions on Neural Systems and Rehabilitation Engineering (2010), 18(3):319-328.
Woods et al., "Offset Prediction for Charge-Balanced Stimulus Waveforms," J. Neural Eng. (2011), 8:1-9.
Wu et al., "A Versatile Multichannel Direct-Synthesized Electrical Stimulator for FES Applications," IEEE Transactions on Instrumentation and Measurement (2002), 51(1):2-9.
Wu et al., "A Versatile Multichannel Direct-Synthesized Electrical Stimulator for FES Applications," IEEE, (2000), pp. 180-185.
Wu et al., "Inductive Generation of Arbitrary Waveforms for Electrical Stimulation Using Implantable Microcoils," J. Micromech. Microeng. (2004), 14:1012-1021.
Xu et al., "A Multi-Channel Telemetry System for Brain Microstimulation in Freely Roaming Animals," Journal of Neuroscience Methods (2004), 133:57-63.
Xu et al., "A Programmable Multi-Channel Stimulator for Array Electrodes in Transcutaneous Electrical Stimulation," Proceeding of the IEEE/ICME International Conference on Complex Medical Engineering, (May 2011), pp. 652-656.
Xu et al., "A Versatile Microprocessor-Based Multichannel Stimulator for Experimental Use in Epidural Spinal Cord Stimulation," 2005 First International Conference on Neural Interface and Control Proceedings.
Yao et al., "A Low-Profile Three-Dimensional Neural Stimulating Array with On-Chip Current Generation," Proceedings of the 26th Annual International Conference of the IEEE EMBS (Sep. 2004), pp. 1994-1997.

(56) References Cited

OTHER PUBLICATIONS

Yao, "CMOS Based 16-Channel Neural/Muscular Stimulation System with Arbitrary Waveform and Active Charge Balancing Circuit," IEEE (2011), pp. 456-459.
Ye et al., "A Portable Telemetry System for Brain Stimulation and Neuronal Activity Recording in Freely Behaving Small Animals," Journal of Neuroscience Methods (2008), 174:186-193.
Zakzewski et al., "Design and Implementation of a Constant-Current Pulsed Iontophoretic Stimulation Device," Medical & Biological Engineering & Computing (Nov. 1996), pp. 484-488.
Zanos et al., "The Neurochip-2: An Autonomous Head-Fixed Computer for Recording and Stimulating in Freely Behaving Monkeys," IEEE Transactions on Neural Systems and Rehabilitation Engineering (2011), 19(4):427-438.
Zaraska et al., "Design and Fabrication of Neurostimulator Implants—Selected Problems," Microelectronics Reliability (2005), 45:1930-1934.
Zhang et al., "A Simple Miniature Device for Wireless Stimulation of Neural Circuits in Small Behaving Animals," Journal of Neuroscience Methods (2011), 202:1-8.
Zhang et al., "Implantable CMOS Neuro-Stimulus Chip for Visual Prosthesis," Research Papers (2011), 54 (4):898-908.
Ziaie et al., "A Single-Channel Implantable Microstimulator for Functional Neuromuscular Stimulation," IEEE Transactions on Biomedical Engineering (1997), 44(10):909-920.
Zierhofer et al., "Electronic Design of a Cochlear Implant for Multichannel High-Rate Pulsatile Stimulation Strategies," IEEE Transactions on Rehabilitation Engineering (1995), 3(1):112-116.
Chiang et al., "Design and performance of a multichannel vestibular prosthesis that restores semicircular canal sensation in rhesus monkey", IEEE Trans Neural Syst Rehabil Eng (2011), 19(5):588-598.
Hottowy et al., "Properties and application of a multichannel integrated circuit for low-artifact, patterned electrical stimulation of neural tissue", J Neural Eng (2012), 9(6):066005.
Amer et al., "Novel Design of Multichannel Electrotherapeutic System," Journal of Medical Engineering and Technology (2009), 33(5):394-402.
Andreu et al., "A Distributed Architecture for Activating the Peripheral Nervous System," Journal of Neural Engineering (2009), 6:1-18.
Andrianova et al., "An Apparatus for Electrical Stimulation of Muscles, Model Stimul-1," All-union Scientific-Research Institute of Medica Instrumentation, Moscow (1977), No. 2, pp. 17-19.
Arabi et al., "Electronic Design of a Multichannel Programmable Implant for Neuromuscular Electrical Stimulation," IEEE Transactions on Rehabilitation Engineering (1999), 7(2):204-214.
Arfin et al., "Wireless Neural Stimulation in Freely Behaving Small Animals," J. Neurophysical (2009), 102:598-605.
Azin et al., "A Battery-Powered Activity-Dependent Intracortical Microstimulation IC for Brain-Machine-Brain Interface," IEEE Journal of Solid-State Circuits (2011), 46(4):731-745.
Ba et al., "Multi-Waveforms Generator Dedicated to Selective and Continuous Stimulations of the Bladder," IEEE (Sep. 2003), pp. 1569-1572.
Berger et al., "A Hippocampal Cognitive Prosthesis: Multi-Input, Multi-Output Nonlinear Modeling and VLSI Implementation," IEEE Transactions on Neural Systems and Rehabilitation Engineering (2012), 20(2):198-211.
Bhadra et al., "Implanted Stimulators for Restoration of Function in Spinal Cord Injury," Medical Engineering & Physics (2001), 23:19-28.
Bourret et al., "Programmable High-Amplitude Balanced Stimulus Current-Source for Implantable Microstimulators," Proceedings—19th International Conference (Oct. 1997), pp. 1938-1941.
Boyer et al., "Implantable Selective Stimulator to Improve Bladder Voiding: Design and Chronic Experiments in Dogs," IEEE Transactions on Rehabilitation Engineering (2000), 8(4):464-470.
Breen et al., "A System for the Delivery of Programmable, Adaptive Stimulation Intensity Envelopes for Drop Foot Correction Applications," Medical Engineering & Physics (2006), 28:177-186.
Broberg et al., "A Custom-Chip-Based Functional Electrical Stimulation System," IEEE Transactions on Biomedical Engineering (1994), 41(9):909-912.
Buckett et al., "A Flexible, Portable System for Neuromuscular Stimulation in the Paralyzed Upper Extremity," IEEE Transactions on Biomedical Engineering (1998), 35(11):897-904.
Bugbee et al., "An Implant for Chronic Selective Stimulation of Nerves," Medical Engineering & Physics (2001), 23:29-36.
Cameron et al., "Micromodular Electronic Devices to Activate Paralyzed Muscles and Limbs," Proceedings of the 15th Annual International Conference of the IEEE (1993), pp. 1242-1243.
Cameron et al., "Micromodular Implants to Provide Electrical Stimulation of Paralyzed Muscles and Limbs," IEEE Transactions on Biomedical Engineering (1997), 44(9):781-790.
Chaing et al., "Design and Performance of a Multichannel Vestibular Prosthesis that Restores Semicircular Canal Sensation in Rhesus Monkey," IEEE Transactions on Neural Systems and Rehabilitation Engineering (2011), 19 (5):588-598.
Chang et al., "A Novel System Design for Implantable Stimulator Application," Proceedings of the 26th Annual International Conference of the IEEE EMBS, (Sep. 1-5, 2004), pp. 4107-4110.
Chao et al., "A System to Integrate Electrical Stimulation with Robotically Controlled Treadmill Training to Rehabilitate Stepping after Spinal Cord Injury," IEEE Transactions on Neural Systems and Rehabilitation Engineering (2012), 20 (5):730-737.
Chen et al., "A 12v-500µA Neuron Stimulator with Current Calibration Mechanism in 0.18µm Standard CMOS Process", IEEE (2011), pp. 57-60.
Chen et al., "An Integrated 256-Channel Epiretinal Prosthesis," IEEE Journal of Solid-State Circuits (2010), 45 (9):1946-1956.
Chen et al., "Development and Application of a Versatile FES System," Journal of Medical and Biological Engineering (2004), 24(1)37-43.
Cheng et al., "Development of a Circuit for Functional Electrical Stimulation," IEEE Transactions on Neural Systems and Rehabilitation Engineering (2004), 12(1):43-47.
Cho et al., "A SU-8-Based Fully Integrated Biocompatible Inductively Powered Wireless Neurostimulator," Journal of Microelectromechanical System (2013), 22(1):170-176.
Cilingiroglu et al., "A Zero-Voltage Switching Technique for Minimizing the Current-Source Power of Implanted Stimulators," IEEE Transactions on Biomedical Circuits and Systems (2013), 7(4):469-479.
Clements et al., "An Implantable Neuro-Stimulator Device for a Retinal Prosthesis," IEEE International Solid-State Circuits Conference (Feb. 1999), pp. 216, 217, and 462.
Clements et al., "An Implantable Power and Data Receiver and Neuro-Stimulus Chip for a Retinal Prosthesis System", IEEE (1999), pp. I-194-I-197.
Constandinou et al., "A Partial-Current-Steering Biphasic Stimulation Driver for Vestibular Prosthesis," IEEE Transactions on Biomedical Circuits and Systems (2008), 2(2):106-113.
Coulombe et al., "A Highly Flexible System for Microstimulation of the Visual Cortex: Design and Implementation," IEEE Transactions on Biomedical Circuits and Systems (2007), 1(4):258-269.
Coulombe et al., "A Power Efficient Electronic Implant for a Visual Cortical Neuroprosthesis," International Center for Artificial Organs and Transplantation (2005), 29(3):233-238.
Demarco et al., "An Arbitrary Waveform Stimulus Circuit for Visual Prostheses Using a Low-Area Multibias DAC," IEEE Journal of Solid-State Circuits (2003), 38(10):1679-1690.
Doherty et al., "Transcutaneous Powering of Implantable Micro-Stimulators for Functional Restoration of Impaired Gastrointestinal Motility," Proceedings of the 35th Annual International Conference of the IEEE EMBS (Sep. 2003), pp. 1575-1578.
Dommel et al., "The Design and Testing of an Epi-Retinal Vision Prosthesis Neurostimulator Capable of Concurrent Parallel Stimulation," Proceedings of the 28th Annual International Conference of the IEEE EMBS (Aug. 2006), pp. 4700-4709.
Dong et al., "A Wideband Wireless Micro-Stimulating AISC for Cochlear Implant," IEEE (2005), pp. 274-278.

(56) References Cited

OTHER PUBLICATIONS

Dou et al., "Stimulator for Real Time Control of Paralyzed Muscles During Functional Electrical Stimulation," ICECS (1996), pp. 1096-1099.

Dura et al., "High-Frequency Electrical Stimulation of Cardiac Cells and Application to Artifact Reduction," IEEE Transactions on Biomedical Circuits and Systems (2012), 59(5):1381-1390.

Ethier et al., "Exponential Current Pule Generation for Efficient Very High-Impedance Multisite Stimulation," IEEE Transactions on Biomedical Circuits and Systems (2011), 5(1):30-38.

Ewing et al- "SaBer DBS: A Fully Programmable, Rechargeable, Bilateral, Charge-Balanced Preclinical Microstimulator for Long-Term Neural Stimulation," Journal of Neuroscience Methods (2013), 2213:228-235.

Fisekovic et al., "New Controller for Functional Electrical Stimulation Systems," Medical Engineering & Physics (2001), 23:391-399.

Forni et al., "Portable Microstimulator for Chronic Deep Brain Stimulation in Freely Moving Rats," Journal of Neuroscience Methods (2012), 209:50-57.

Forster et al., "Theoretical Design and Implementation of a Transcutaneous, Multichannel Stimulator for Neural Prosthesis Applications," J. Biomed, Engng. (1981), 3:107-120.

Fridman et al., "Safe Direct Current Stimulation to Expand Capabilities of Neural Prostheses," IEEE Transactions on Neural Systems and Rehabilitation Engineering (2013), 21(2):319-328.

Furumiya et al., "Optimization of Electrical Stimulus Pulse Parameter for Low-Power Operation of Retinal Prosthetic Device," Japanese Journal of Applied Physics (2006), 45(19)L505-L507.

Furumiya et al., "Pulse-Frequency-Modulation Vision Chip with Frequency Range Control as a Retinal Prosthesis Device," Proc. of SPIE (2003), 4829:1002-1003.

Gaddam et al., "Remote Power Delivery for Hybrid Integrated Bio-Implantable Electrical Simulation System," Proc. of SPIE (2005), 5763:20-31.

Gheewala et al., "A CMOS Implantable Multielectrode Auditory Stimulator for the Deaf," IEEE Journal of Solid-State Circuits (1975), SC-10(6):472-479.

Ghovanloo et al., "A Modular 32-Site Wireless Neural Stimulation Microsystem," IEEE Journal of Solid-State Circuits (2004), 39(12):2457-2466.

Ghovanloo et al., "A Tri-State FSK Demodulator for Asynchronous Timing of High-Rate Stimulation Pulses in Wireless Implantable Microstimulators," Proceedings of the 2nd International IEEE EMBS (Mar. 2005), pp. v-viii.

Ghovanloo et al., "A Wideband Frequency-Shift Keying Wireless Link for Inductively Powered Biomedical Implants," IEEE Transactions on Circuits and Systems (2004), 51(12):2374-2383.

Matei et al., "A Biomedical Implantable FES Battery-Powered Micro-Stimulator," IEEE Custom Integrated Circuits Conference (CICC), (2008), pp. 317-324.

Mavoori et al., "A Miniature Implantable Computer for Functional Electrical Stimulation and Recording of Neuromuscular Activity," IEEE International Workshop on Biomedical Circuits & System, (2004), pp. 13-16.

McDermott, "An Advanced Multiple Channel Cochlear Implant," IEEE Transactions on Biomedical Engineering (1989), 36(7)789-797.

McNeal, "Analysis of a Model for Excitation of Myelinated Nerve," IEEE Transactions on Biomedical Engineering (1976), BME-23(4):329-337.

McNulty et al., "Design of a Highly Efficient Circuit for Electrical Muscle Stimulation," Presented at the Biomedical Circuits and Systems Conference (2006), pp. 202-205.

Millard et al., "A Fully Implantable Stimulator for Use in Small Laboratory Animals," Journal of Neuroscience Methods (2007), 166:168-177.

Minzly et al., "Computer-Controlled Portable Stimulator for Paraplegic Patients," J. Biomed. Eng. (1993), 15:333-338.

Moradi et al., "New Charge Balancing Method Based on Imbalanced Biphasic Current Pulses for Functional Electrical Stimulation," 20th Iranian Conference on Electrical Engineering, (ICEE), (May 2012), pp. 270-274.

Nadeau et al., "A Flexible High Voltage Biphasic Current-Controlled Stimulator," IEEE (2006), pp. 206-209.

Nam et al., "A Retrofitted Neural Recording System with a Novel Stimulation IC to Monitor Early Neural Responses from a Stimulating Electrode," Journal of Neuroscience Methods (2009), 178:99-102.

Ng et al., "Pulse Frequency Modulation Based on CMOS Image Sensor for Subretinal Stimulation," IEEE Transactions on Circuits and Systems (2006), 53(6):487-491.

Nguyen et al., "Mixed-Signal Template-Based Reduction Scheme for Stimulus Artifact Removal in Electrical Stimulation," Med. Biol. Eng. Comput. (2013), 51:449-458.

Nohama et al., "A Solution for Linearity, Stability and Frequency Bandwidth in PAM Electrocutaneous Stimulators' Isolation Interface," Med. Eng. Phys. (1996), 18(8):692-695.

Noorsal et al., "A Neural Stimulator Fronted with High-Voltage Compliance and Programmable Pulse Shape for Epiretinal Implants," IEEE Journal of Solid-State Circuits (2012), 47(1):244-256.

Novo et al., "A Sub-Micron CMOS Programmable Charge Pump for Implantable Pacemaker," Analog Integrated Circuits and Signal Processing (2001), 27:211-217.

Novo et al., "Programmable Voltage Multiplier for Pacemaker Output Pulse Generation," Electronics Letters (1999), 35(7):560-561.

Ocadiz, "Programmable Eight Channel Surface Stimulator," IEEE, (1994), pp. 990-991.

Ohlsson et al., "Miniaturised Device for Long-Term Intravaginal Electrical Stimulation for the Treatment of Urinary Incontinence," Med. & Biol. Eng. & Comput. (1988), 26:509-516.

Ohta et al., "Retinal prosthesis Device Based on Pulse-Frequency-Modulation Vision Chip," IEEE (2005), pp. 2923-2926.

Ohta et al., "Silicon LSI-Based Smart Simulators for Retinal Prosthesis," IEEE Engineering in Medicine and Biology Magazine (2006), pp. 47-59.

Ortmanns et al., "A 232-Channel Epiretinal Stimulator ASIC," IEEE Journal of Solid-State Circuits (2007), 42 (12):2946-2959.

Pancrazio et al., "Description and Demonstration of a CMOS Amplifier-Based-System with Measurement and Stimulation Capability for Bioelectrical Signal Transduction," Biosensors & Bioelectronics (1998), 13:971-979.

Passama et al., "Computer-Based Remote Programming and Control of Stimulation Units," Proceedings of the 5th International IEEE EMBS Conference on Neural Engineering, (2011), pp. 538-541.

Peckham et al., "Multichannel Implantable Stimulator for Control of Paralyzed Muscle," IEEE Transactions on Biomedical Engineering (1981), BME-28(7):530-536.

Peng et al., "A Combined Wireless Neural Stimulating and Recording System for Study of Pain Processing," Journal of Neuroscience Methods (2008), 170:25-34.

Peng et al., "High Frequency Block of Selected Axons Using an Implantable Microstimulator," Journal of Neuroscience Methods (2004), 134:81-90.

Poletto et al., "A High Voltage Stimulator for Small Electrode Electrocutaneous Stimulation," IEEE (1997), pp. 2415-2418.

Poletto et al., "A high voltage, constant current stimulator for electrocutaneous stimulation through small electrodes", IEEE Trans Biomed Eng (1999), 46(8):929-936.

Pourmehdi et al., "A Custom Designed Chip to Control an Implantable Stimulator and Telemetry System for Control of Paralyzed Muscles," Artificial Organs (1999), 23(5):396-398.

Sabut et al., "Design of a Programmable Multi-Pattern FES System for Restoring Foot Drop in Stroke Rehabilitation," Journal of Medical Engineering & Technology (2010), 34(3):217-223.

Santina et al., "A Multichannel Semicircular Canal Neural Prosthesis Using Electrical Stimulation to Restore 3-D Vestibular Sensation," IEEE Transactions on Biomedical Engineering (2007), 54(6):1016-1030.

(56) References Cited

OTHER PUBLICATIONS

Sardarzadeh et al., "An Implantable Electrical Stimulator for Phrenic Nerve Stimulation," J. Biomedical Science and Engineering (2012), 5:141-145.

Sawan et al., "A New Multichannel Bladder Stimulator," Dept. of Electrical Engineering, (1990), pp. 190-196.

Sawan et al., "Wireless Smart Implants Dedicated to Multichannel Monitoring and Microstimulation," IEEE Circuits and Systems Magazine (2005), pp. 21-39.

Schaning et al., "A High-Voltage Bipolar Transconductance Amplifier for Electrotactile Stimulation," IEEE Transactions on Biomedical Engineering (2008), 55(10):2433-2443.

Schwartz et al., "Single Chip CMOS Image Sensors for a Retina Implant System," IEEE Transactions on Circuits and Systems (1999), 46(7):870-877.

Schwartz et al., "Single Chip CMOS Imagers and Flexible Microelectronic Stimulators for a Retina Implant System," Sensors and Actuators (2000), 83:40-46.

Shahrokhi et al., "The 128-Channel Fully Differential Digital Integrated Neural Recording and Stimulation Interface," IEEE Transactions on Biomedical Circuits and Systems (2010), 4(3):149-161.

Shen et al., "A Linearized Current Stimulator for Deep Brain Stimulation," 32nd Annual International Conference of the IEEE EMBS, (2010), pp. 6485-6488.

Shen et al., "Microelectronic Neural Bridge for Signal Regeneration and Function Rebuilding Over Two Separate Nerves," Journal of Semiconductors (2011), 32(6):1-5.

Shire et al., "Development and Implantation of a Minimally Invasive Wireless Subretinal Neurostimulator," IEEE Transactions on Biomedical Engineering (2009), 56(10):2502-2511.

Shkel et al., "An Electronic Prosthesis Mimicking the Dynamic Vestibular Function," Audiol Neurotol (2006), 11:113-122.

Simcox et al., "A Portable, 8-Channel Transcutaneous Stimulator for Paraplegic Muscle Training and Mobility—A Technical Note," Journal of Rehabilitation Research & Development (2004), 41(1):41-51.

Singh et al., "A Matched Biphasic Microstimulator for an Implantable Retinal Prosthetic Device," IEEE (2004), pp. IV-1-IV-4.

Sit et al., "A Low-Power Blocking-Capacitor-Free Charge-Balanced Electrode-Stimulator Chip with Less Than 6 nA DC Error for 1-mA Full-Scale Stimulation", IEEE Transactions on Biomedical Circuits and Systems (2007), 1 (3):172-183.

Sivaprakasam et al., "A Variable Range Bi-Phasic Current Stimulus Driver Circuitry for an Implantable Retinal Prosthetic Device," IEEE Journal of Solid-State Circuits (1998), 40(3):763-771.

Sivaprakasam et al., "Architecture Tradeoffs in High-Density Microstimulators for Retinal Prosthesis," IEEE Transactions on Biomedical Circuits and Systems (2005), 52(12):2629-2641.

Smith et al., "An Externally Powered, Multichannel, Implantable Stimulator for Versatile Control of Paralyzed Muscle," IEEE Transactions on Biomedical Engineering (1987), BME-34(7):499-508.

Smith et al., "An Externally Powered, Multichannel, Implantable Stimulator-Telemeter for Control of Paralyzed Muscle," IEEE Transactions on Biomedical Engineering (1998), 45(4):463-475.

Song et al., "A Sub-10 nA DC-Balanced Adaptive Stimulator IC with Multi-Modulal Sensor for Compact Electro-Acupuncture Stimulation," IEEE Transactions on Biomedical Circuits and Systems (2012), 6(6):533-541.

\* cited by examiner (a)

(b)

(c)

(a)

(b)

(a)

(b)

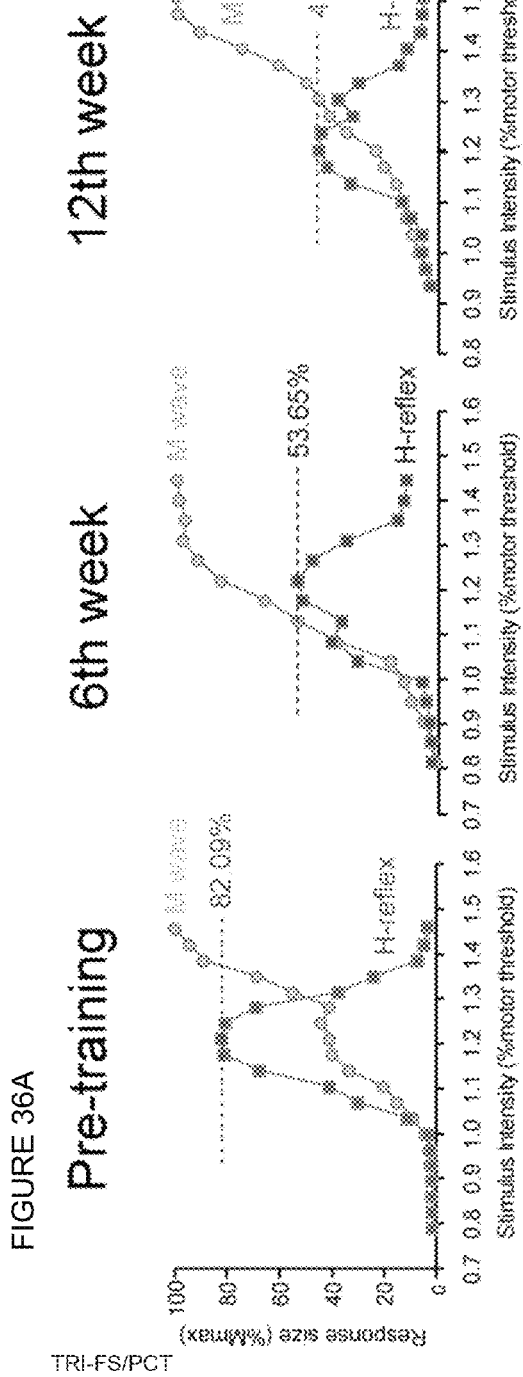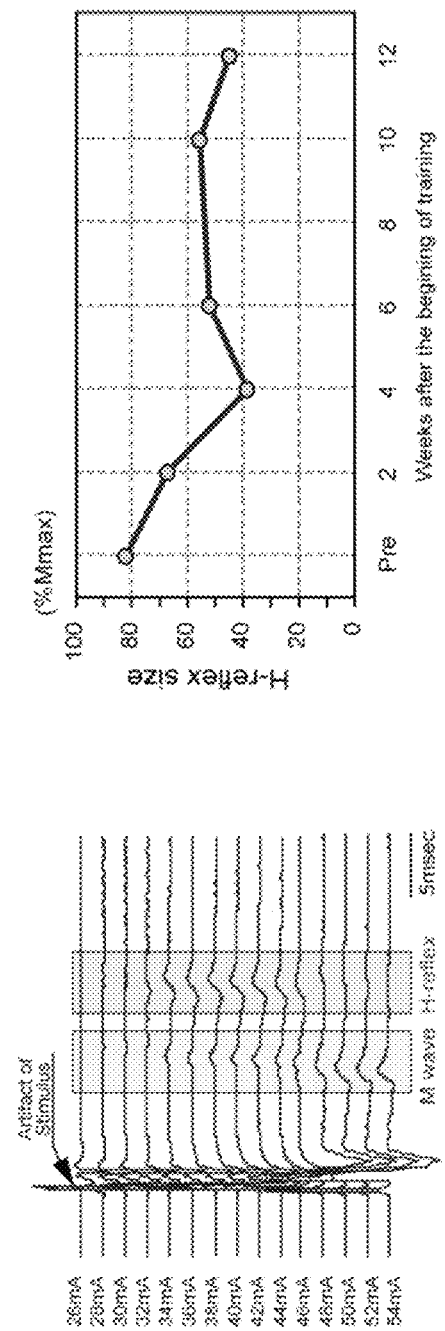
FIGURE 36A
FIGURE 36B
FIGURE 36C

Trajectory in horizontal space

Normalized by Shoulder position

FUNCTIONAL ELECTRICAL STIMULATION DEVICE AND SYSTEM, AND USE THEREOF

CROSS REFERENCE TO RELATED APPLICATIONS

This patent application is a continuation application of U.S. application Ser. No. 13/701,722, filed Dec. 3, 2012, which is U.S. nationalization under 35 U.S.C. §371 of International Application No. PCT/CA2011/000637, filed Jun. 2, 2011, which claims the benefit of priority under 35 U.S.C. §119(e) to U.S. Provisional Application Ser. No. 61/351,715, filed Jun. 4, 2010. The disclosures set forth in the referenced applications are incorporated herein by reference in their entireties into the Detailed Description below, including all information as originally submitted to the United States Patent and Trademark Office.

FIELD OF THE DISCLOSURE

The present disclosure relates to electrical stimulation, and in particular, to a functional electrical stimulation device and system.

BACKGROUND

The general principles of functional electrical stimulation (FES) are rooted in the physiological process of nerve and muscle excitation. These excitations are a result of action potentials (APs) that occur in the body at the neuronal level. APs are the messenger signals for the nervous system. They occur in nervous system tissue in response to stimuli, which can be natural or artificial. In the case of FES, these stimuli are charge pulses. Depending on the amplitude, duration and frequency of these stimuli they can cause excitation in different tissues. FES therapies use these excitation pulses to treat patients with impairments in different areas of the body. Owing to the complexity of generating APs, the artificial electrical stimulation pulses which can generate these APs may require particular pulse types and stimulation schemes for FES applications.

All body cells display a membrane potential, which is a separation of positive and negative charges across the membrane. This potential is related to the uneven distribution of potassium ions (K+ ions), sodium ions (Na+ ions) and large intracellular protein anions between the intracellular and extracellular fluid and to the differential permeability of the plasma membrane to these ions.

Two types of cells, muscle cells and nerve cells, have developed specialized use for this membrane potential. Nerve and muscle are excitable tissues that by changing their resting potential are able to produce electrical signals—or action potentials (APs)—to communicate. FES uses artificial stimuli in the form of electrical pulses to elicit excitation in different tissues.

Neuromuscular electrical stimulation (NMES) is one of the useful therapeutic methods to improve motor function. Studies examining the use of NMES have demonstrated improvements in joint range of motion, force and torque production, magnitude of electromyographic (EMG) muscular activity, and reduction of muscle tone. While the above studies used NMES for single-segment exercise and muscle strengthening, more recently, some studies have been focused on the effect of electrical stimulation on improving and/or restoring voluntary functions such as grasping, walking, reaching, breathing, swallowing and so on in severely disabled individuals. Functional electrical stimulation (FES) is a device-mediated therapy that integrates electrical stimulation of sensory-motor systems and repetitive functional movement of the paretic limb or a body part or a body function in patients with different forms of neuromuscular disorder, such as stroke, spinal cord injury, multiple sclerosis, cerebral palsy, and traumatic brain injury, to name a few.

Known FES devices, although useful, have had limited success at reaching their full potential. For example, previous devices have not been able to ensure charge balance over time because of partial control over temporal characteristics and amplitude. They also provide a limited number of pulses and require complicated and costly adjustments for use in different FES applications. The inflexibility of these designs, in some cases, translates to underutilization of FES therapy.

Nonetheless, various functional electrical stimulators have been used over time to improve the lives of patients with various neurological and musculoskeletal disorders and muscular atrophies as well as in therapy for sport injuries. Known FES devices provide electrical pulses activating a single or a group of muscles, to create a movement (neuroprsthetic applications) and/or build up the muscle mass (neuromuscular stimulation applications). FES devices have also been used in treating bladder problems, easing the symptoms of Parkinson's disease and numerous other applications. Generally, for each application a specific FES system is used.

In emerging sophisticated applications, such as FES therapy, brain machine interface controlled neuroprostheses for grasping and close-loop controlled neuroprotheses for sitting and standing balance, the FES systems would generally have to provide a much wider range and variety of pulses compared to conventional application-specific systems. For example, sophisticated FES applications may generally require the output power stage to produce pulses for which amplitudes, durations, shapes and/or frequencies can be changed in real-time from one pulse to the other, for example. FIG. 1 shows common classifications of pulse shapes that can be used in FES applications. Systems allowing for the seamless transition from one pulse shape to another could allow for greater treatment flexibility. Furthermore, systems demonstrating greater power efficiency and having a relatively small volume may promote greater sustainability as battery powered portable systems, for example.

Known stimulators typically produce either voltage or current regulated electrical pulses. In recent years, the latter have been more widely accepted, because the current regulated pulses generally deliver the same amount of charge to the tissue regardless of tissue resistance. However, the current mode solutions suffer from potential problems related to partially detached electrodes that can suddenly increase the resistance path and, consequently, result in an overly large voltage. The excessive voltage may cause discomfort and burns in the patient with reduced or loss of sensation. On the other hand, an equivalent scenario can be envisioned with voltage mode controlled stimulators. A sudden reduction in the tissue resistance, due to the voltage breakdown of the tissue, may cause an abrupt increase in the stimulation current. Hence, it could be desirable to regulate both voltage and current. From the practical implementation point of view, most current source solutions have a disadvantage of operating output transistors in linear mode, which results in undesirable heat dissipation. Consequently, the battery life is significantly reduced and the overall size of the power stage is often significantly increased due to additional cooling requirements.

Another parameter of interest in these applications is the rise time, i.e. the slew rate of the electrical pulses, which, in general, should be as fast as possible. Namely, the relevance of providing a fast rise time in these pulses stems from the physiology of excitable tissues, namely nerve and muscle cells, and the generation of action potentials. These tissues have ion pumps that work against the delivered charge of an electrical pulse to maintain the nominal potential difference on the cell membrane. Pulses with a higher slew rate may give less time to the ion pumps to compensate for the delivered charge, allowing stimulation with lower amplitude signal. The advantages of stimulating with lower amplitude pulses may include more comfortable (i.e. less painful) therapy and a longer battery life of the device, for example.

Another parameter of interest in these applications, particularly where bipolar pulses (see FIG. 1) are used, is that the net electric charge brought by each pulse be as close to zero as possible, which parameter generally applies in the application of symmetric and asymmetric bipolar pulses. This feature is generally considered relevant in preventing or at least reducing charge accumulation in the tissue, which may cause a galvanic process that may lead to tissue breakdown, for example. To address this problem, auxiliary discharging circuits are frequently used in known devices, where after each bipolar pulse, the accumulated charge due to unbalanced operation is released on a resistor, for example. While this solution may result in zero accumulation, it generally increases heat dissipation and reduces maximum pulse frequency, i.e., due to the extra time needed for the discharge.

Based on the above and other drawbacks, most of the conventional application-specific FES systems cannot be directly used in emerging FES applications. For example, they generally cannot offer a sufficiently wide range and variety of pulses for such applications, they are generally unsuitable for sustainable battery-operated solutions given overly large power consumption significantly limiting their operational time, and/or are generally unable to simultaneously provide signals for multiple channels, for example, which may be of particular relevance in systems such as neuroprostheses for standing and walking. These limitations mostly come from the output power stage that, in the current designs, operates as a lossy linear mode current source causing heat dissipation. Another drawback to predominantly used current source based devices is their signal slew rate, which is significantly smaller than that of the voltage mode systems, thus further contributing to power losses and resulting in a less comfortable therapy.

Accordingly, there is a need for a functional electrical stimulation (FES) device and system, that overcome some of the drawbacks of known technologies, or at least, that provide the public with a useful alternative.

The above background information is provided to reveal information believed by the applicant to be of possible relevance to the present invention. No admission is necessarily intended, nor should be construed, that any of the preceding information constitutes prior art against the present invention.

SUMMARY

An object of the invention is to provide a functional electrical stimulation device and system, and use thereof. In accordance with an aspect of the invention, there is provided an electrical stimulation device for providing sequential bipolar pulse stimulation to an area of a living body via one or more electrode leads applied to the area, comprising a current pulse generating circuit comprising output nodes for operative coupling to the one or more electrode leads, and configured for operative coupling to a substantially constant voltage supply, said current pulse generating circuit comprising positive and negative stimulation paths drawing from said substantially constant voltage supply to respectively apply positive and negative currents through the area via the one or more electrode leads, said stimulation paths comprising respective capacitive elements, a capacitance ratio of which dictating, at least in part, an amplitude ratio of said positive and negative currents, wherein periodic alternative activation of said stimulation paths provides the sequential bipolar pulse stimulation.

In accordance with another embodiment of the invention, there is provided a functional electrical stimulation (FES) system for providing current pulse stimulation to an area of a living body via one or more electrodes applied to the area, comprising: a control platform having one or more inputs for receiving FES parameters representative of selected current pulse characteristics to be applied to the area; an output stage operatively coupled to said control platform for generating current pulses in accordance with said characteristics via said one or more electrodes, said output stage comprising: a power supply; a pulse generating circuit operatively coupled to said power supply to draw a current therefrom; and one or more controllers operatively coupled to said power supply and pulse generating circuit, said one or more controllers configured to control operation of said pulse generating circuit to generate said current pulses in accordance with said characteristics, and monitor at least one of a supply voltage and supply current provided via said power supply in regulating said characteristics.

In accordance with another embodiment of the invention, there is provided a electrical stimulation device for providing current pulse stimulation to an area of a living body via one or more electrode leads applied to the area, the device comprising a current pulse generating circuit comprising output nodes for operative coupling to the one or more electrode leads, and configured for operative coupling to a voltage supply, said current pulse generating circuit comprising a positive and a negative stimulation path, each said path comprising a respective charging element and a respective activation switch, wherein each said respective charging element is charged by said voltage supply and discharged upon activation of said respective activation switch to generate positive and negative current pulses respectively, such that a pulse rise time of said positive and negative current pulses is predominantly dictated by a switching speed of each said respective switch.

In accordance with another embodiment of the invention, embodiments of the herein described devices and systems are used in providing functional electrical stimulation for improving one or more of muscle, associated nerve, brain and spinal cord function in individuals suffering from a neuromuscular deficit, stroke, multiple sclerosis, spinal cord injury, central nervous system injury or a muscular injury.

In accordance with another embodiment of the invention, embodiments of the herein described devices and systems are used for providing functional electrical stimulation to a plurality of associated nerves capable of communicating therebetween, so as to encourage communication amongst said nerves. For example, in one embodiment, the functional electrical stimulation is applied at an intensity of from about a multiple of the motor unit activation threshold to about three times the motor unit activation threshold. In a further embodiment, the functional electrical stimulation is applied at an intensity of about two times the motor unit activation threshold. In a further embodiment, a communicative interconnectivity between the nerves improves over time.

In accordance with another embodiment of the invention, functional electrical stimulation is used for promoting communication therebetween a plurality of associated nerves comprising applying functional electrical stimulation to the plurality of associated nerves at an intensity of about a multiple of about one of a motor unit activation threshold to about three times the motor unit activation threshold whereby over time communicative interconnectivity therebetween said nerves is improved. In a further embodiment, the electrical stimulation is applied as symmetrical bipolar pulses. In a further embodiment, the electrical stimulation is provided at a frequency of about 40 Hz. In a further embodiment, the pulses are applied for about 250 μsec.

In accordance with another embodiment of the invention, embodiments of the herein described devices and systems are used in providing functional electrical stimulation to a plurality of associated nerves capable of communicating therebetween, so as to promote neuroplasticity, and improve communication amongst said nerves.

Other aims, objects, advantages and features of the invention will become more apparent upon reading of the following non-restrictive description of specific embodiments thereof, given by way of example only with reference to the accompanying drawings.

BRIEF DESCRIPTION OF THE FIGURES

Several embodiments of the present disclosure will be provided, by way of examples only, with reference to the appended drawings, wherein:

FIG. 36A is a graph of recruitment curves of H-reflex and M wave obtained in pre-training and at various time points;

FIG. 36B is a graph of exemplary elicited M wave and H-reflex curves;

FIG. 36C is a graph of changes of H-reflex and M response curves with time course of training;

DETAILED DESCRIPTION

Figure 1:
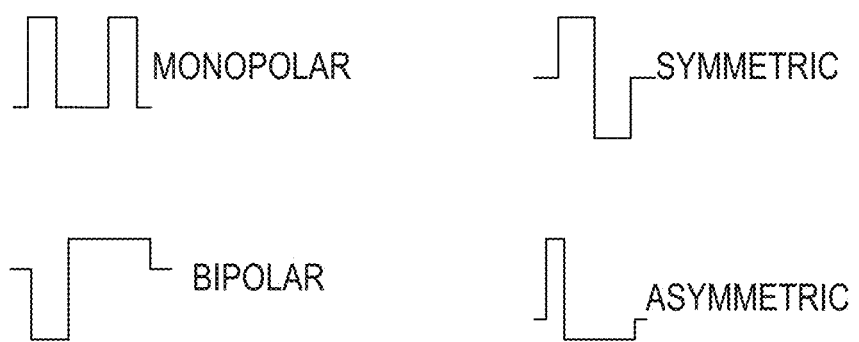
FIG. 1 is schematic representation of various pulse characteristics applicable in different FES applications, a selection of one or more of which being available through implementation of different embodiments of the invention.

It should be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical or electrical connections or couplings. Furthermore, and as described in subsequent paragraphs, the specific mechanical or electrical configurations illustrated in the drawings are intended to exemplify embodiments of the disclosure. However, other alternative mechanical or electrical configurations are possible which are considered to be within the teachings of the instant disclosure. Furthermore, unless otherwise indicated, the term "or" is to be considered inclusive.

With reference to the disclosure herein and the appended figures, a functional electrical stimulation (FES) device and system, and use thereof will now be described, in accordance with different embodiments of the invention.

Figure 2:
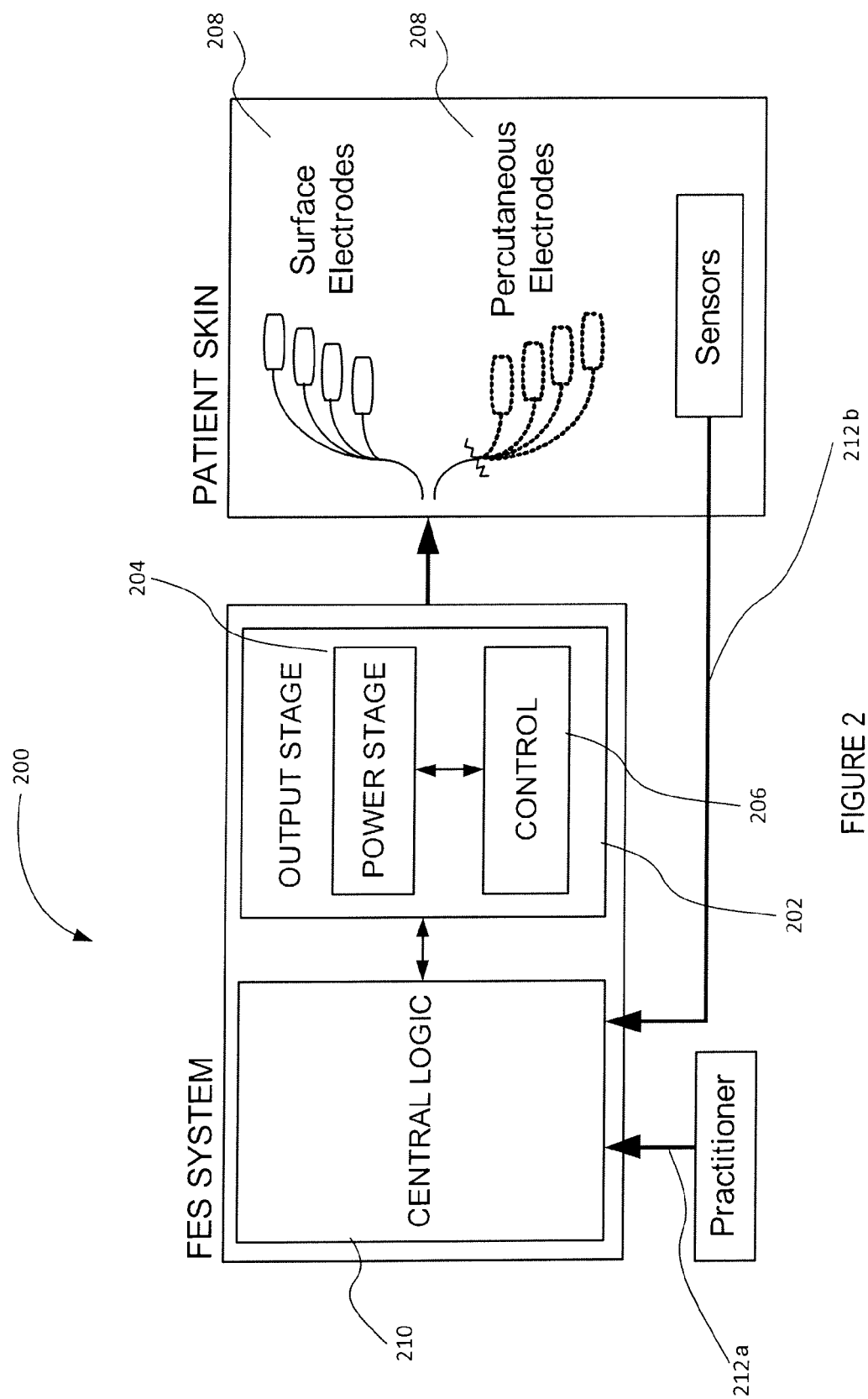
FIG. 2 is a high level diagram of a FES system, in accordance with one embodiment of the invention.

In particular, FIG. 2 provides a high level diagram of an FES system 200, in accordance with one embodiment of the invention. In this particular embodiment, the FES system consists of an external system, however, as will be discussed further below, a similar system may be designed and implemented for internal implementation (e.g. an implantable system), without departing from the general scope and nature of the present disclosure. The system 200 generally comprises an output stage 202 comprising a power stage 204 for creating electrical pulses and a controller 206 that regulates operation of the power stage 204. The system 200 may further include, or be configured for operative coupling with one or more stimulation electrodes 208 to deliver the pulses generated by the power stage 204 to the targeted tissues, for example, through the skin (e.g. surface/transcutaneous electrodes), directly by penetrating the body (e.g. percutaneous electrodes), and the like. A central processing platform or central logic 210 is also illustratively provided to communicate intended pulse characteristics to the output stage 202, for example, based on external inputs 212a from a practitioner or operator (e.g. via one or more activation switches, dials and/or other such user operable interfaces, and/or via one or more user-selectable preprogrammed stimulation sequences stored or otherwise accessed by the system for implementation) or from another device, such as one or more physiological sensors 212b configured to regulate or influence operation of the FES system 200 based on one or more sensed physiological parameters associated with or indicative as to an effectiveness of the FES treatment in question, for example.

The structure of FES pulses for stimulation may be determined by several characteristics, for example: pulse type (current or voltage), amplitude, duration, rise time, frequency, polarity, number of phases and symmetry, which characteristics will be further described below. Accordingly, the provision of a flexible FES system may allow for greater versatility in providing different FES treatments wherein variation in one or more of these pulse stimulation characteristics may be advantageously adjusted for improved treatment effectiveness. The examples described below, in accordance with different embodiments of the invention, are generally adapted for the generation of current stimulation pulses based on one or more adjustable and/or selectable pulse characteristics such as pulse amplitude, duration, rise time, frequency, polarity and symmetry, which characteristics will be described in greater detail below. Furthermore, given the nature of these treatments, patient safety is also of particular concern, and the provision of safety features is also particularly desirable, in accordance with different embodiments of the invention.

Pulse Type:

As noted above, the provision of current pulses, as opposed to voltage pulses, are generally considered herein in the provision of FES. Inter-variable and intra-variable differences in tissue resistance that may affect such pulses may include, but are not limited to, perspiration, skin movement and increased circulation that typically result from FES, for example. In order to maintain a desired pulse amplitude, for example, current and/or voltage regulation may be desirable. In some exemplary embodiments of FES therapy, current regulation may be preferred since a desired charge is delivered to the tissue, regardless of the tissue resistance.

Pulse Amplitude and Duration:

In general, an action potential is only generated if the membrane potential reaches a threshold membrane potential. From patient to patient, there is a range of different tissue impedances. Also, within each patient, each type of tissue may have distinct impedance. Therefore, different current amplitudes of FES generated pulses may be necessary to address these impedance variations. Also, the type of tissue being stimulated may thus become a parameter for determining the amplitude level and the pulse duration of a given FES treatment. For example, localized stimulation of small muscles generally requires shorter less intense pulses, whereas deeper muscle stimulation requires higher amplitude and longer pulse duration.

Pulse Rise Time:

The rise time of current pulses may be relevant in providing enhanced FES treatments. For example, if the pulse rise time is too slow, the membrane potential may accommodate or adjust to the stimulus. Accordingly, despite otherwise adequate stimulation pulses, a threshold membrane potential may not be achieved and the desired neuro-muscular excitation may not occur. Similarly, an improved (i.e. decreased) pulse rise-time may translate in lower requirements for pulse amplitude to achieve a similar stimulation. Such reductions in pulse amplitude may translate in a reduction in power consumption and a reduction in the total absolute charge being applied to the tissue, which may be of particular interest in certain applications.

Pulse Frequency:

The frequency of pulse delivery determines the rate of action potential generation in the tissue. If the stimulation frequency is at or greater than 40 Hz, the generated action potentials create continuous muscle (tetanic) contractions. If the stimulation frequency is between 16 and 40 Hz, many individuals may feel discontinuous muscle contraction (non-tetanic contraction); however, the muscles are still able to generate a functional task. For stimulation frequencies below 16 Hz continuous, (tetanic) muscle contraction is very unlikely. The higher the stimulation frequency, the faster the muscles fatigue and the lesser the discomfort experienced by the patient.

Pulse Polarity and Symmetry:

Pulses may be monopolar (positive or negative) or bipolar (positive and negative). Bipolar pulses can be symmetric or asymmetric. The different permutations of these characteristics are illustrated, for example, in FIG. 1.

The abovementioned characteristics define the type and shape of pulses used in FES applications. For external stimulation, for example, the charge balance on the tissue is preferably maintained as excess charge build up in the tissue over time can result in galvanic processes and cause significant tissue damage and pain. For this reason, bipolar pulses that apply the same amount of charge in each direction are used most often in clinical practice. An asymmetric pulse with one negative phase at a given amplitude and duration and one second positive phase at one quarter the amplitude for 4 times the duration are believed to produce improved results for external FES applications, however, other pulse duration and amplitude ratios may also be considered in the present context without departing from the general context of the present disclosure. Depending on the application at hand, improved accuracy and control on pulse stimulation parameters may allow for a more accurate and effective treatment, not to mention improved patient safety and comfort levels. For example, the provision of reduced pulse rise times (which may effectively contribute to a reduction in pulse amplitudes (energy) utilized to generate desired muscle contractions), tight control over pulse temporal characteristics and pulse amplitude, may all contribute to a reduction in the likelihood of charge build up, and thus represent a constant opportunity for FES system improvements.

In Table 1 below, various pulse characteristics and their effect on FES are summarized, along with respective criteria applicable in the context of FES applications in providing improved FES treatment opportunities, at least some of which generally achieved in the implementation of the various embodiments of the invention herein described, and their equivalents.

TABLE 1

Exemplary pulse characteristics

| Pulse Characteristic/Effect | Criteria for FES Applications |
|---|---|
| Pulse type: regulated current pulses can provide predictable levels of excitation in response to changing tissue impedance over the course of stimulation. | Regulating the current level accurately may provide reliable pulses for stimulation and repeatable responses for FES therapies. |
| Amplitude and duration: different tissue types may benefit from different pulse amplitude ranges and/or durations. | Adjusting/controlling current pulse amplitude and/or duration based on intended FES application may enhance results. |
| Pulse rise time: faster rise times may generally reduce the likelihood of or otherwise advantageously affect occurrence of tissue membrane accommodation. | Producing faster pulse rise times may lead to the more reliable generation of APs. Therefore, square shaped pulses may be more effective in initiating APs, for example in neuronal or muscle tissues. Secondary effects may include a reduction in required pulse amplitude to induce similar effect, which may translate in reduced power consumption and secondary effects in tissue (e.g. discomfort/damage). |

TABLE 1-continued

Exemplary pulse characteristics

| Pulse Characteristic/Effect | Criteria for FES Applications |
| --- | --- |
| Pulse frequency: within pulse frequencies of about 0 to 100 Hz, the stimulation frequency generally determines the rate of APs. Beyond 100 Hz, the rate of APs in not necessarily coincident stimulation frequency. Stimulation frequencies above 1,000 Hz may incapacitate excitable tissues and thus not generate APs. | A range of pulse frequencies may allow for different FES applications. |
| Pulse polarity and symmetry: symmetric or asymmetric; monopolar or bipolar. | Added flexibility in the generation of different pulse shapes and/or sequences may advantageously affect results of different FES applications. |

Figure 3:
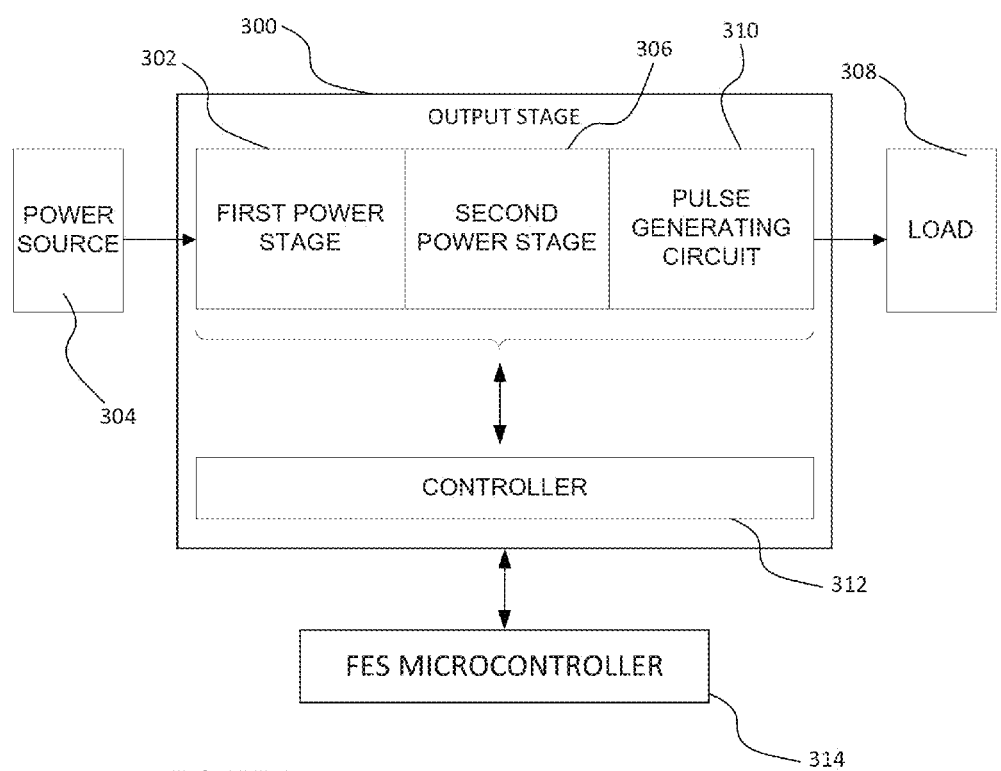
FIG. 3 is a schematic diagram of an output stage of an FES system, in accordance with one embodiment of the invention.

With reference to FIG. 3, and in accordance with one embodiment of the invention, an exemplary output stage 300 is generally depicted. In this example, the output stage 300 generally comprises a first power stage 302 operatively coupled to a power source 304, such as a battery or the like, to increase the voltage supply available to a second power stage 306 in providing sufficient current to implement various FES pulse sequences/parameters to a load 308 via a pulse generating circuit 310. A controller 312 is also provided to control various operational aspects of the output stage 300, such as voltage and/or current regulation and control to regulate FES parameter values and/or implement various safety procedures, as well as control operation of the pulse generating circuit in accordance with one or more selectable FES treatment sequences/parameters. A general FES microcontroller 314 may also be provided in providing overall control features, for example in the context of an overall FES system incorporating output stage 300.

In one embodiment, the output stage consists of a two-stage digitally controlled switch-mode power supply (SMPS). For example, and with reference to the illustrative embodiments of FIGS. 4 and 5, the output stage (400, 500) may use two switched mode power supplies (SMPS) arranged in series. The first SMPS, a flyback converter (402, 502) in these examples, steps up the supply voltage or a battery voltage (404, 504) such that the second SMPS, a buck converter (406, 506) in these examples, can generate the required current pulse amplitudes at the output to stimulate the load (408), i.e. via a distinct or integrated (i.e. merged) pulse generating circuit, which in these examples, consist of a switched capacitor circuit (410, 510) described in greater detail below in accordance with different embodiments of the invention.

In the implementation of a battery operated FES system or device, to the use of a low power high frequency SMPS with digital control can lead to significant increases in battery life as compared to other available power supply architectures. Furthermore, by using switching power converters such as those exemplified above, it is possible to efficiently perform a DC-DC conversion while providing for potential galvanic isolation between the power source and output. This stems from the fact that the magnetic devices used in such systems consume essentially no power. Also, the switching elements of these devices are generally either off, or in saturation, which can also contribute to energy savings.

Figure 4:
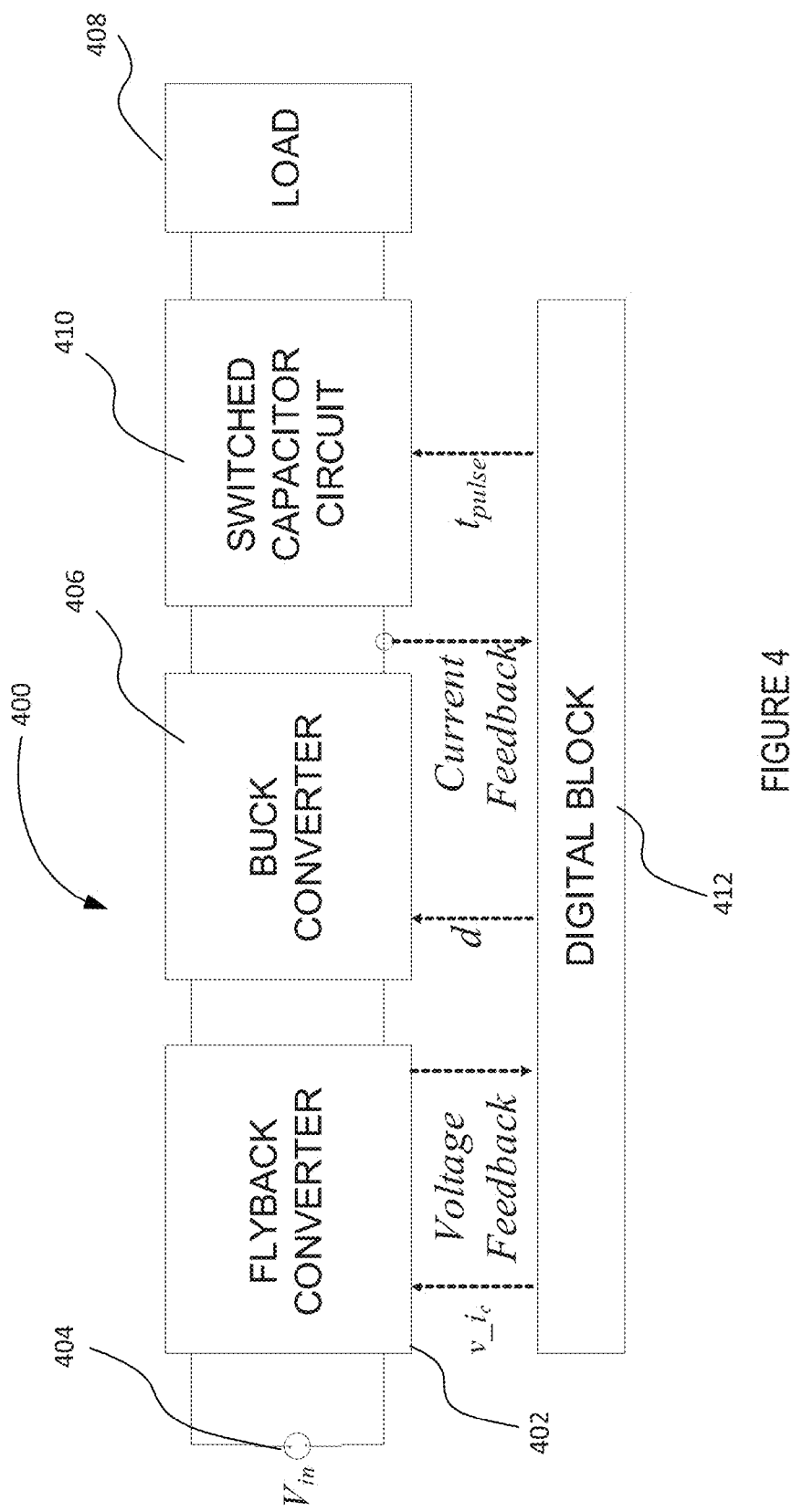
FIG. 4 is a schematic diagram of an output stage of an FES system having a digitally controlled two-stage switched mode power supply (SMPS), in accordance with one embodiment of the invention.
Figure 5:
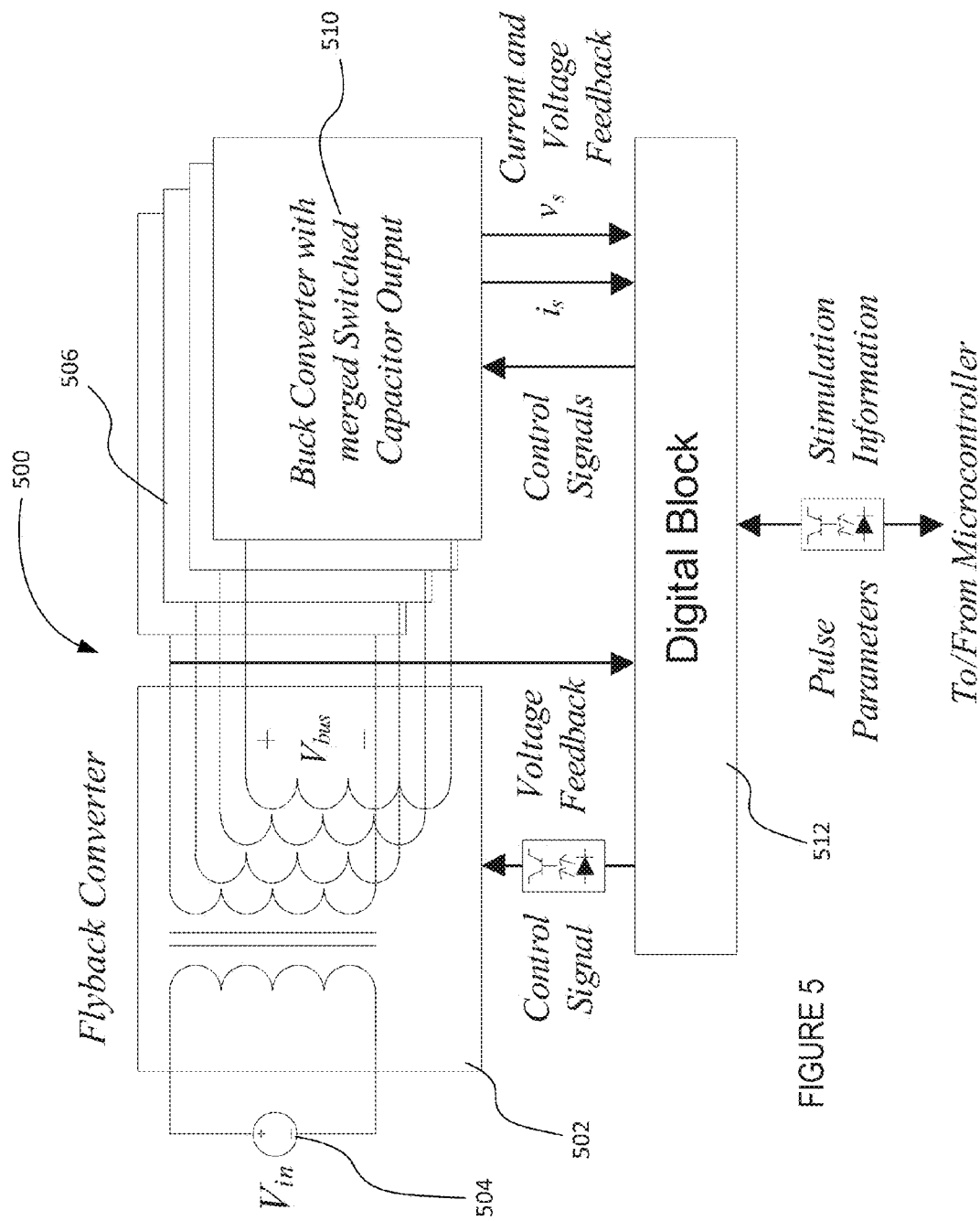
FIG. 5 is a schematic diagram of an output stage of multiple-channel FES system having a digitally controlled two-stage switched mode power supply (SMPS), in accordance with one embodiment of the invention.

Still referring to FIGS. 4 and 5, the pulse generating circuit (410, 510), in accordance with some embodiments, comprises a switched capacitor circuit that is a part of the second power stage (406, 506) to generate different pulse patterns consistent with input control parameters communicated thereto via, in this example, a common digital block/controller (412, 512).

As will be described in greater detail below with reference to detailed illustrative embodiments, the pulse generating circuit (410, 510) may comprise a switched-capacitor circuit that allows the formation of various pulse profiles with relatively fast rise time, clean pulse characteristics and substantial charge balancing in bipolar operation (i.e. to reduce or avoid charge build up in the stimulated tissue which can lead to tissue damage), for example. For example, in one embodiment, the switch capacitor portion of the second, i.e. downstream, power stage may inherently provide zero (or effectively zero) accumulated charge when bipolar pulse patterns are applied. Such pulse profiles may include in different combinations, but are not limited to, monopolar, bipolar, monophasic, biphasic symmetric and/or asymmetric pulse sequences, which may vary in time, amplitude and/or frequency depending on external and/or internal input to the system, as shown for example in FIG. 1.

In one embodiment (e.g. see FIG. 5), the switched-capacitor circuit 510 is integrated within the buck converter topology 506. Such output power stage, a step-down DC-DC converter, generally respects the basic principle of capacitor charge balance when operating at equilibrium. For instance, in regulated power stages, the average value on the output capacitors used in the converter may be configured to be zero, as dictated by the following relationship.

$$0 = \frac{1}{T_s} \int_0^{T_s} i_c(t)dt = \langle i_c \rangle$$

From this relationship, the switched capacitor output may be incorporated into the output of the step-down switched converter to deliver the pulses to the load.

Still referring to FIGS. 4 and 5, the digital block/controller 410, 510 may be provided for controlling various aspects of the output stage, be it voltage and/or current feedback control of the first and/or second power stages, and/or for the provision of various control signals to the first or second power stage and/or pulse generating circuit. This controller may also provide for enhanced system flexibility and/or different layers of protection for the patient. For example, in one embodiment, a digital current mode control may provide current overload protection. Furthermore, digital control and logic may enable the adjustment of various system and pulse parameters to adapt the system to different FES treatment protocols, sequences and therapies, and/or different tissue types, patients and/or patient conditions, to name a few. For example, in one embodiment, the controller may be configured to regulate output current levels as a function of various parameters such as tissue type, patient-to-patient variations and/or variations for a same patient over time. Namely, a relatively fast controller may be used to regulate the output current levels during each pulse phase to provide accurate current amplitude. Since the resistance of skin can vary between 400Ω and 3 kΩ, it may be desirable in an exemplary embodiment to step up the battery voltage to several hundred volts to create current pulses ranging from 0 to 125 mA, for example.

To simplify the following examples, description will be limited to the demonstration of single channel implementation, however, and as shown schematically in FIG. 5, the various aspects of the invention herein described may be readily extended to multiple channels, as will be discussed in greater detail in the following examples.

First Output Power Stage

As shown generally in the examples of FIGS. 4 and 5, an output stage of an FES system, in accordance with different embodiments of the invention, may comprise a flyback converter or the like to step up the voltage of an associated power source, such as a battery. The flyback topology can provide an isolated transformer, which generally lends itself well to biomedical applications by providing galvanic isolation from high voltage components, as well as having the potential to transmit power wirelessly for implantable FES applications. Furthermore, and with particular reference to FIG. 5, the flyback topology can be readily extended to multiple channels with the addition of extra secondary windings.

Figure 6:
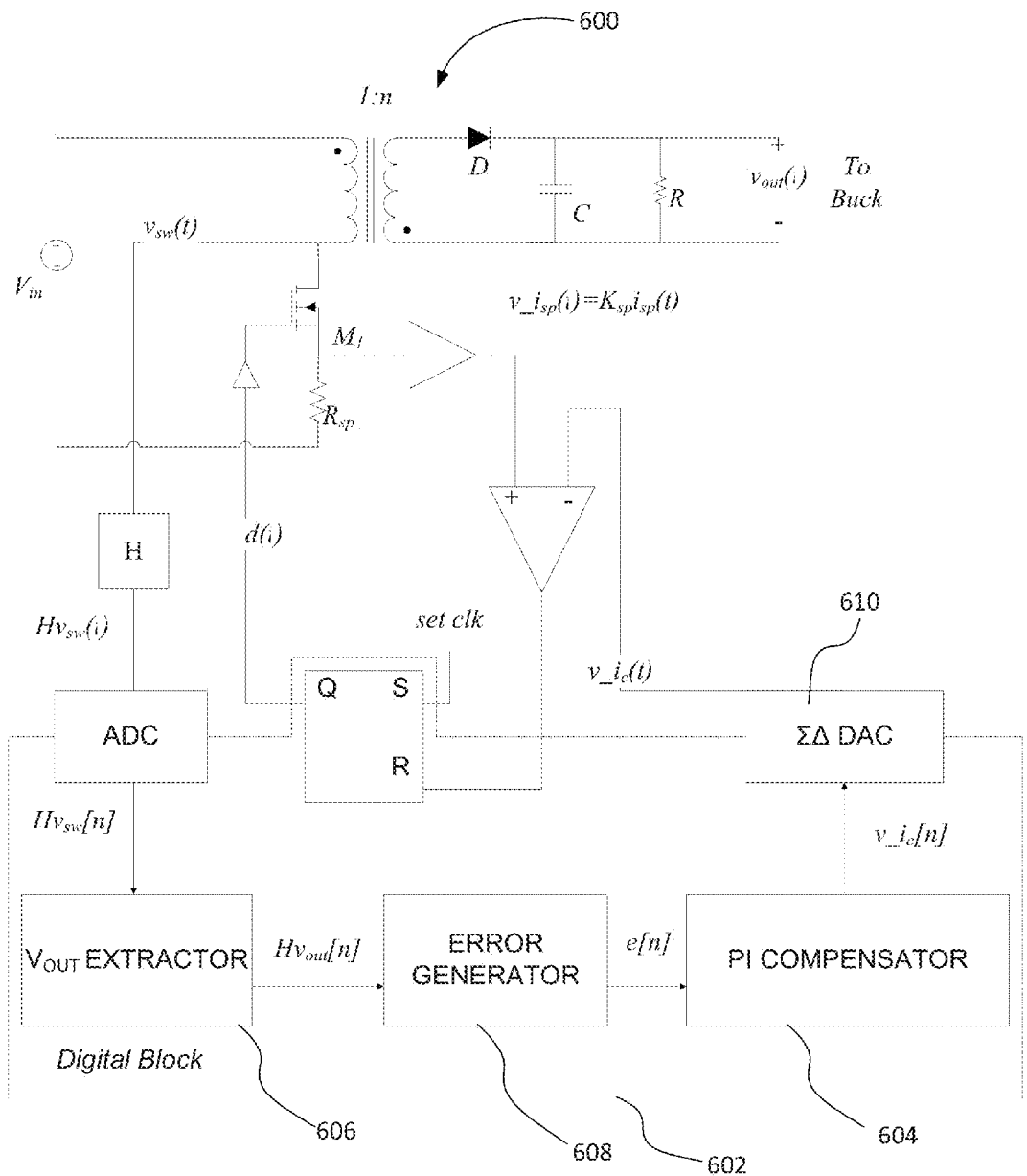
FIG. 6 is a detailed schematic diagram of a first output power stage of an FES device, in accordance with one embodiment of the invention.

With reference to FIG. 6, and in accordance with one embodiment, a first example of a flyback converter topology will now be described. In this embodiment, the flyback converter 600 uses a 1:n turns ratio transformer, such as 1:10 or other appropriate ratio depending on the application at hand, in order to provide a second power stage (e.g. see FIG. 12 associated with this example) with a substantially constant high supply voltage $V_{out}$. In general, the flyback converter is designed to operate substantially independently of the second power stage, wherein the output voltage of the flyback is connected in series with the second power stage and pulse generating circuit to provide desired current pulses to the load.

In this example, the output of the flyback converter 600 is digitally controlled by digital block 602, which in this embodiment, consists of a primary side current programmed mode (CPM) controller. In particular, the flyback converter 600 is configured to run in discontinuous conduction mode (DCM)—where the secondary side diode becomes reverse biased—and uses digital CPM primary side control. In this regard, the DCM allows the controller 602 to be positioned fully on the primary side of the flyback 600. Accordingly, the output voltage can be calculated from the primary side switch voltage values without the need for sampling on the secondary side, thus reducing the amount of circuitry on the secondary side, which may be of interest for implantable implementations, for example. Furthermore, CPM generally involves the control of the primary side switch current in peak current mode, which limits the current applied to the secondary side, providing another layer of safety. Additionally, CPM reduces the order of the system; in fact through small signal analysis, the control current to output voltage transfer function can be reduced to one dominant pole and can therefore be controlled using a simple proportional-integral (PI) compensator 604, as shown in this example.

Figure 7:
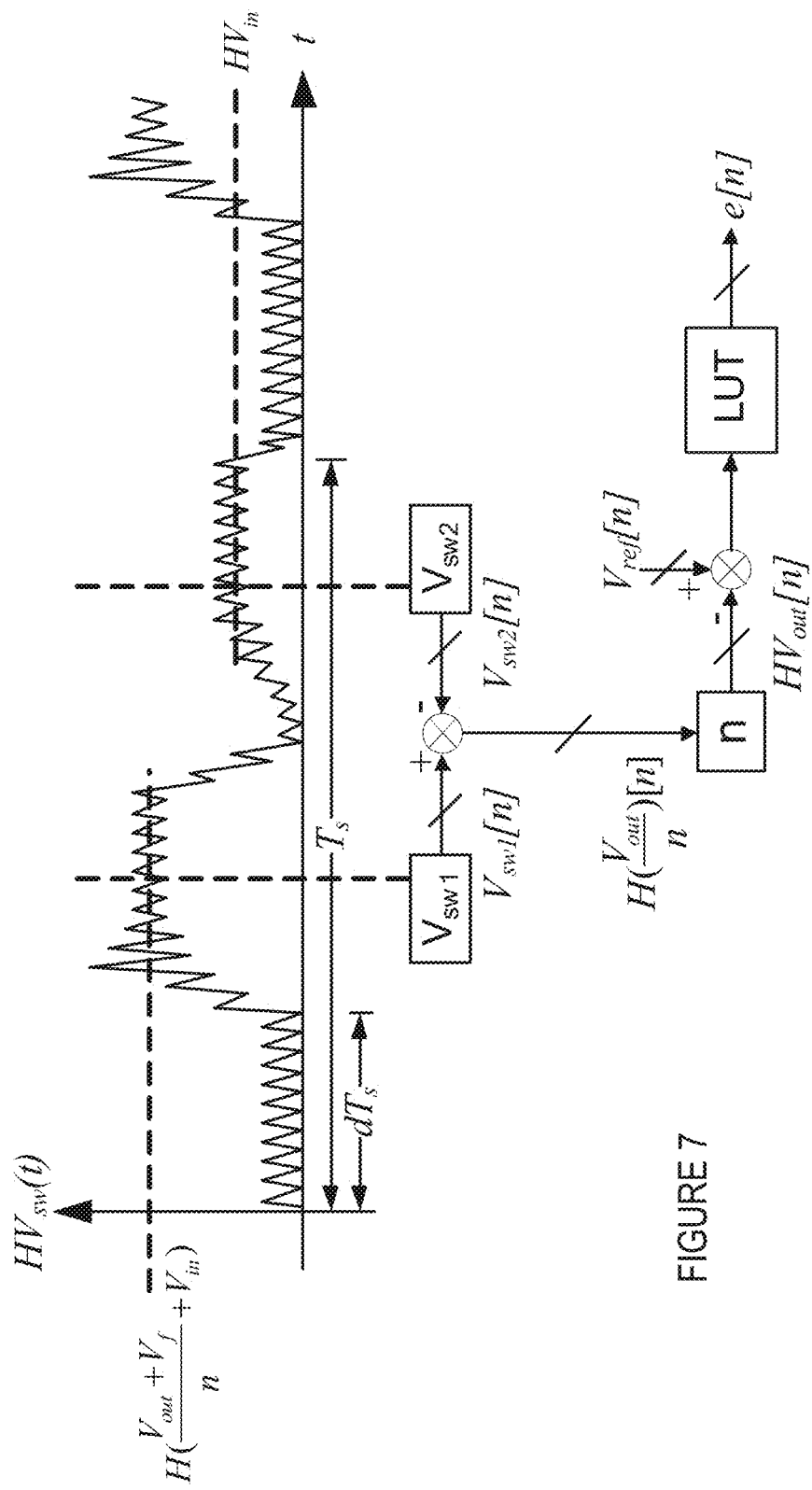
FIG. 7 is a plot and schematic diagram of an output voltage extracted via switch voltage sampling in the output power stage of FIG. 6, in accordance with one embodiment of the invention.

Accordingly, the output voltage of the flyback converter 600 may be regulated in the following sequence, in accordance with one embodiment of the invention. First, the output voltage is extracted on the primary side by sampling the switch voltage twice each switching cycle while in DCM. The switch voltage takes on three values during each switching cycle, as follows:

$$v_{sw1} = i_{sw} R_{on}$$
$$v_{sw2} = \frac{V_{out} + V_f}{n} + V_{in}$$
$$v_{sw3} = V_{in}$$

where $i_{sw}$ is the switch current, $R_{on}$ is the on-resistance of the switch, $V_f$ is the forward voltage of the diode module, and n is the turns ratio. The equations above describe the switch voltage during main switch on phase ($v_{sw1}$), switch off phase ($v_{sw2}$) and when the converter enters DCM ($v_{sw3}$). The voltage is sampled during the switch off and DCM phases using an ADC and stored in two registers. The output voltage is calculated by subtracting these values and multiplying by the turns ratio. The forward voltage of the diode is known from the datasheet and since $V_{out} \gg V_f$ it can be disregarded in the calculations. The extracted output voltage (e.g. via Extractor 606) is fed forward and a digital error value is generated (e.g. via error generator 608) as shown in FIG. 7.

Figure 8:
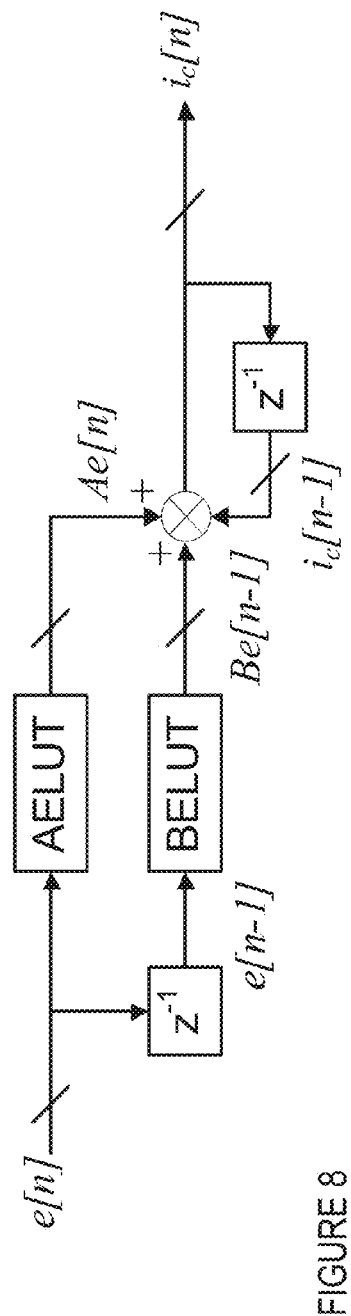
FIG. 8 is a schematic diagram of an exemplary PI compensator architecture of a controller of the output power stage of FIG. 6, in accordance with one embodiment of the invention.

The error value is resolved from subtracting $HV_{out}$ from $V_{ref}$. The error value is mapped in the error look-up-table (LUT). This LUT takes the raw error value and assigns an error value. This error value is fed to the PI compensator 604, which uses the following difference equation to resolve the new control current for the next switching cycle. An exemplary PI architecture is shown in FIG. 8.

$$i_c[n] = ae[n] - be[n-1] + i_c[n-1]$$

Figure 9:
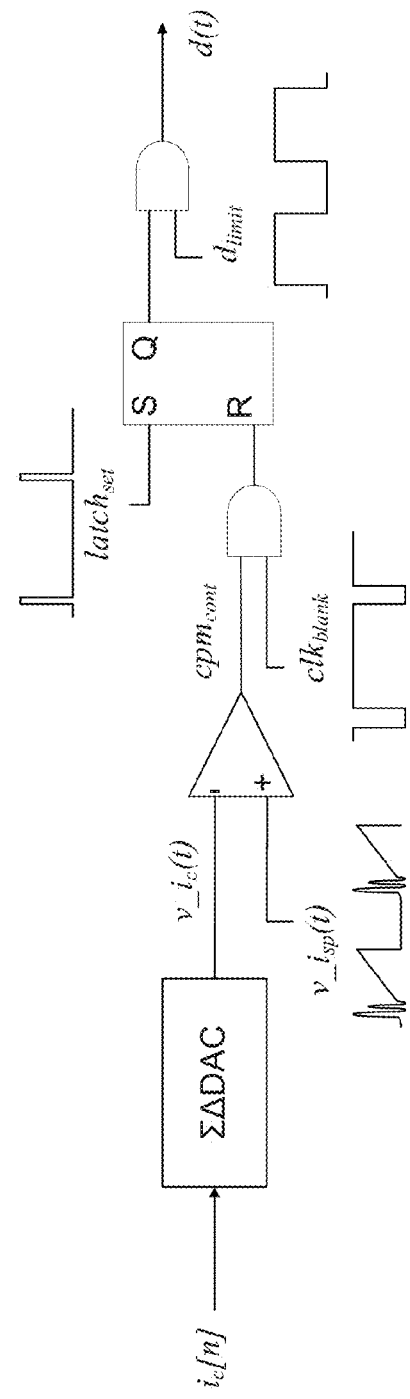
FIG. 9 is a schematic diagram of a peak current duty cycle resolution process implemented by a controller of the output power stage of FIG. 6, in accordance with one embodiment of the invention.

The error value and the delayed error value are multiplied by PI coefficients A and B respectively in AELUT and BELUT. The new control current is calculated through the adder/subtractor, converted to an analog voltage using a sigma-delta digital to analog converter or ΣΔ DAC (610) and fed to the comparator 604 to set the peak current value and thus switch on-time for the next switching cycle. This process is shown in FIG. 9. To achieve an accurate duty cycle, a clean switch current ramp is generally required. However, practical switches suffer from ringing immediately after turn-on. The magnitude of this ringing may exceed the control current, which would cause a false premature comparator high signal resulting in an early reset of the set-reset (SR) latch and a diminished duty cycle. This problem can be alleviated by a blanking clock that ignores the initial period in the switch current, preventing the false reset signal. In order to provide that the converter 600 is not susceptible to oscillation due to perturbation, the duty cycle can be limited to less than 50 percent by a duty limit signal.

Figure 10:
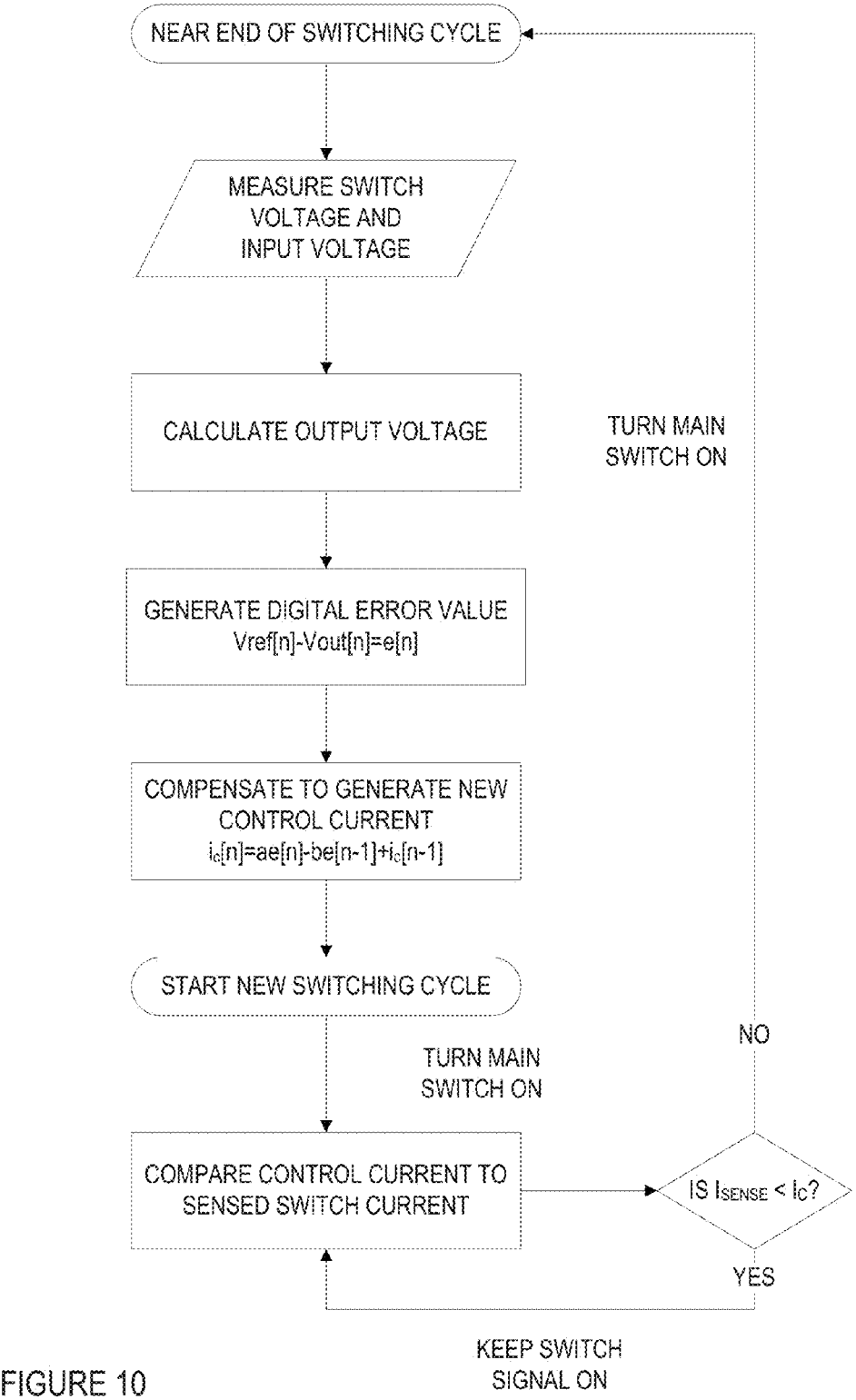
FIG. 10 is a flow diagram of an exemplary control sequence implemented for controlling an output voltage of the output power stage of FIG. 6, in accordance with one embodiment of the invention.

FIG. 10 provides a flowchart of the above-described control sequence, in accordance with one embodiment of the invention.

Figure 11:
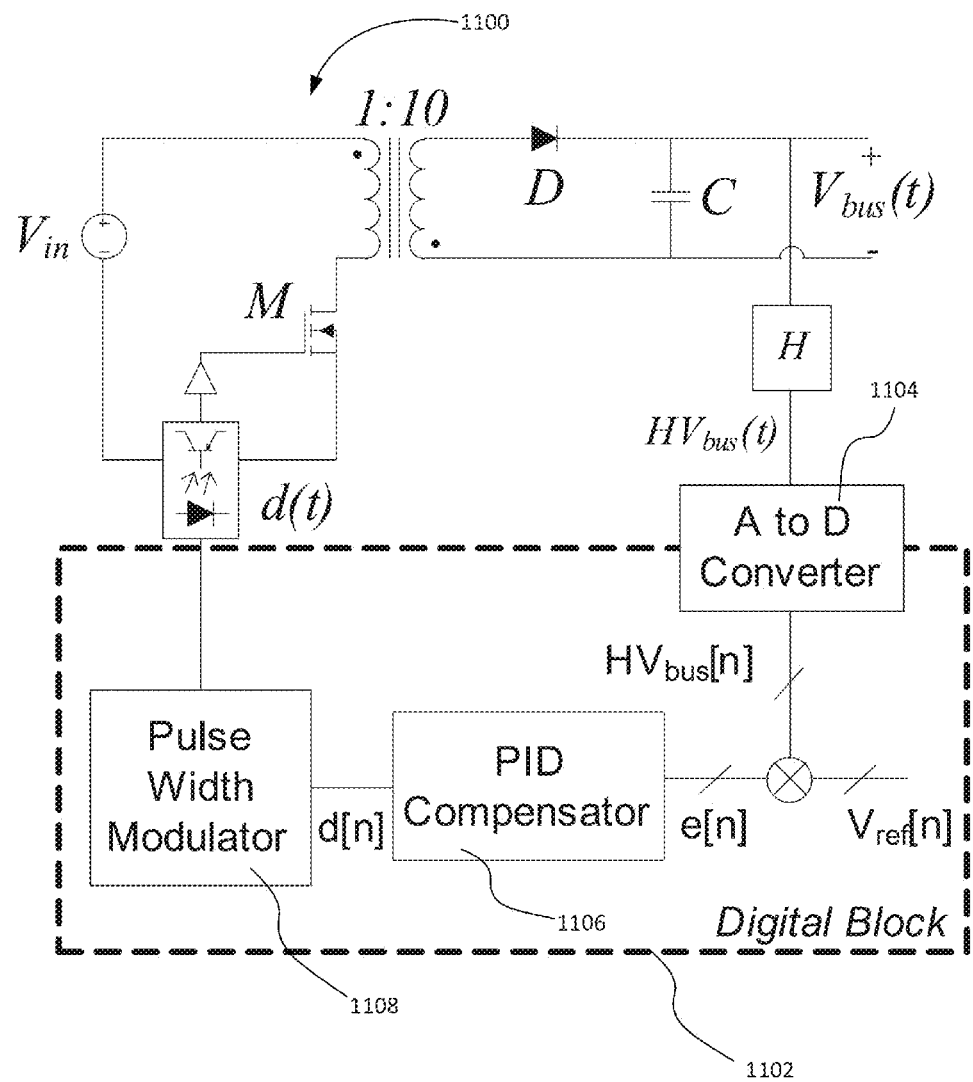
FIG. 11 is a detailed schematic diagram of a first power stage of an FES device, in accordance with another embodiment of the invention.

With reference to FIG. 11, and in accordance with one embodiment, a second example of a flyback converter topology will now be described. In this embodiment, the flyback converter 1100 uses a 1:10 turns ratio transformer in order to provide a second power stage (e.g. see FIG. 13 associated with this example) with a substantially constant high supply voltage $V_{bus}$. In general, the flyback converter is designed to operate substantially independently of the second power stage, wherein the output voltage of the flyback is connected in series with the second power stage and pulse generating circuit to provide desired current pulses to the load.

In this example, the output of the flyback converter 1100 is digitally controlled by digital block 1102, which in this embodiment, consists of a secondary side controller to provide output voltage feedback control. For example, an analog to digital converter (ADC) can sample the flyback output voltage $V_{bus}$ for each switching cycle, which sampled voltage ($HV_{bus}[n]$) may then be compared to a digital reference ($V_{ref}[n]$) to generate an error value (e[n]). In this example, the error value is fed to a PID compensator 1106, which establishes the duty cycle (d[n]) or on-time (fraction of total switch period that main switch M will be active) for the next switching cycle, to be implemented via pulse width modulator (PWM) 1108. Changes in the duty cycle will adjust $V_{bus}$ accordingly until it reaches the desired reference. Again, the output voltage of the flyback 1100 is connected in series with the second power stage and pulse generating circuit to provide desired current pulses to the load.

It will be appreciated by the skilled artisan that other flyback control techniques and methods may be applied in the present context without departing from the general scope and nature of the present disclosure. Furthermore, while the above contemplates different flyback converter configurations for the provision of a first output power stage, it will be appreciated that other types of step-up converters such as boost, buck-boost, cuk, SEPIC, and modifications thereof, as well as other isolated and non-isolated step-up voltage topologies may be considered herein in performing the functions of the first power stage, shown exemplarily herein as a Flyback converter, without departing from the scope and nature of the present disclosure.

Second Output Power Stage

As noted above, and in accordance with one embodiment of the invention, a second output power stage may be provided for operative coupling with a first output power stage, for example as illustratively described above, to draw from a substantially constant voltage supply provided thereby and provide, via a pulse generating circuit operatively coupled thereto, current pulses having and/or selected characteristics.

Figure 12:
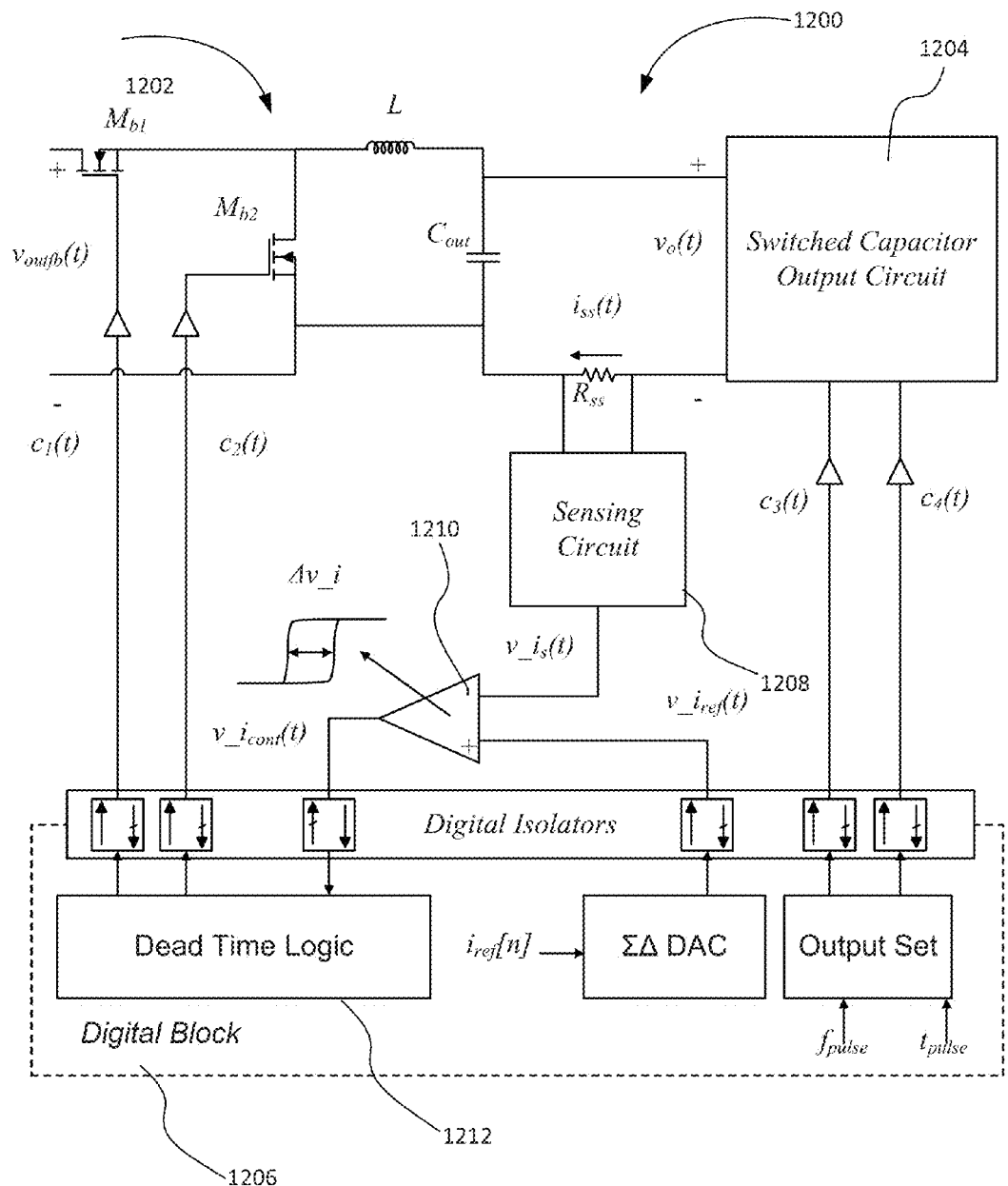
FIG. 12 is a detailed schematic diagram of a second output power stage illustratively drawing from an output voltage of the first output power stage of FIG. 6, in accordance with one embodiment of the invention.

With reference to FIG. 12, and in accordance with one embodiment of the invention, a first example of a second output power stage is provided. In this example, the second power stage 1200 comprises a buck converter 1202 and an integrated pulse generating circuit consisting of switched capacitor output circuit 1204, to be discussed further below in accordance with different embodiments of the invention. A digital block or controller 1206 is also provided, which for example, provides control signals ($c_3$, $c_4$) to the pulse generating circuit 1204 in controlling various pulse characteristics generated thereby (e.g. pulse frequency, duration, type, etc.), as well as control operation of the buck converter 1202 in response to sensed current values monitored via sensing circuit 1208, so to effectively regulate current pulse amplitudes generated thereby.

Figure 13:
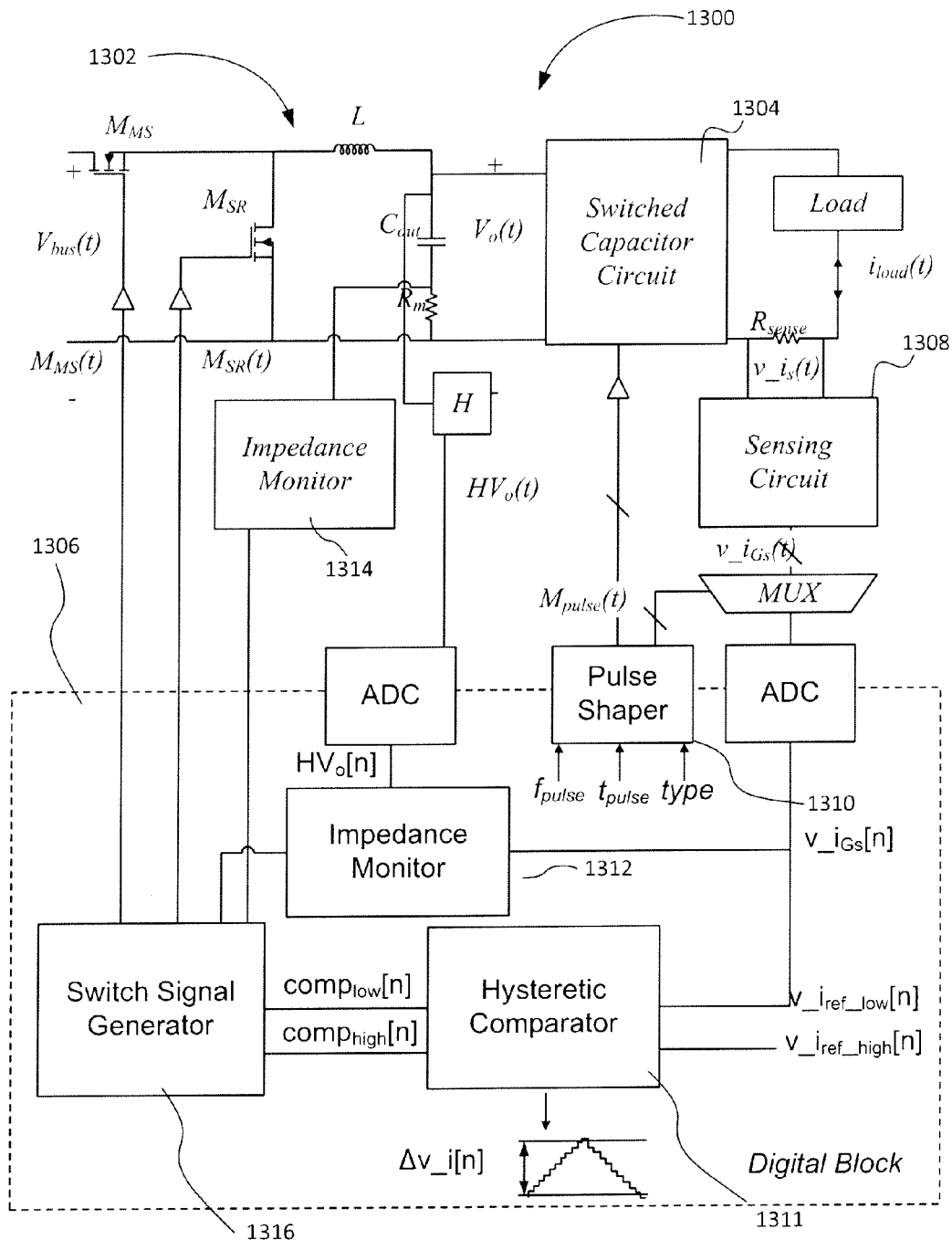
FIG. 13 is a detailed schematic diagram of a second output power stage illustratively drawing from an output voltage of the first output power stage of FIG. 11, in accordance with one embodiment of the invention.

FIG. 13 provides another example of a second output power stage 1300, which again comprises a buck converter 1302 with integrated pulse generating block consisting of a switched capacitor circuit 1304. A digital block or controller 1306 is also provided, which for example, can provide various control signals via pulse shaper 1310 to the pulse generating circuit 1304 in controlling various pulse characteristics generated thereby (e.g. pulse frequency, duration, type, etc.), as well as control operation of the buck converter 1302 in response to sensed current values monitored via sensing circuit 1308, so to effectively regulate current pulse amplitudes generated thereby.

In this embodiment, an additional safety mechanism is also provided, wherein two different methods may be employed to monitor tissue impedance. In the first method, the output voltage and load current are digitally monitored by an impedance monitor 1312 of the digital block 1306; these values can provide an accurate estimation of the load as well as provide overvoltage and overcurrent protection. The second method, an analog alternative, continuously monitors the slope of the inductor current ripple using a differentiator circuit (i.e. impedance monitor 1314). The extracted slope depends on the tissue resistance. The slope is fed to two comparators whose references are set based on the acceptable tissue resistance range. If the tissue resistance falls too low or rises too high, the system shuts down immediately.

With reference to the embodiments of FIGS. 12 and 13, the load may be assumed in some cases to be practically constant for an individual during a single current pulse, however it may change from individual to individual and within each individual over several pulses as skin resistance may change due to perspiration, skin movement and increased circulation that typically results from FES, for example. Therefore, and in accordance with some embodiments, the controller 1206, 1306 may be configured to monitor an output current and adjust accordingly such that second power stage (e.g. buck converter 1202, 1302 in these examples) reaches a sufficient level to provide appropriate or desirable current pulse amplitudes. In these particular embodiments, hysteretic control is provided, which can manifest a relatively fast response with minimal hardware, for example. While hardware minimization may not be of particular relevance to all embodiments, it may be so when implemented, as in the embodiments of FIGS. 12 and 13, on the second power stage of a dual power stage system where the second power stage may be multiplied for a number of parallel stimulation channels (e.g. see FIG. 5) each powered from a same first power stage. In any case, where device size reduction is of interest, the provision of a reduced hardware implementation may be of particular relevance.

Figure 14:
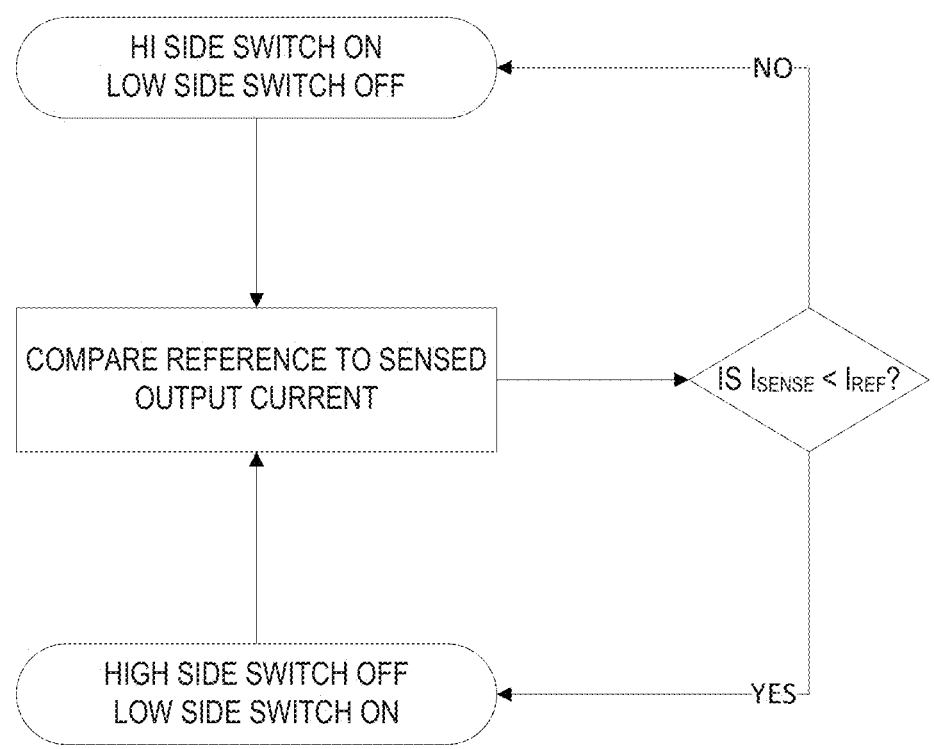
FIG. 14 is a flow diagram of an exemplary hysteretic control sequence for a second output power stage of an FES device, in accordance with one embodiment of the invention.

In implementing hysteretic control, in the context of the embodiments of FIGS. 12 and 13 for example, the main switch ($M_{b1}$, $M_{MS}$) of the buck converter (1202, 1302) remains active until a sensed value (e.g. sensed current over sensing resistor ($R_{ss}$, $R_{sense}$) reaches a reference value plus some voltage margin (i.e. added hysteresis) above it. At this point the main switch turns off and the secondary switch ($M_{b2}$, $M_{SR}$) is turned on until the sensed current falls below the reference value less the same voltage margin. Setting the hysteretic margin at the maximum acceptable voltage variation—in the case of the buck converter, the voltage margin that gives the maximum acceptable current ripple in the output current pulses—is generally sufficient in regulating the output load. FIG. 14 provides a flowchart of the above-described control sequence, in accordance with one embodiment of the invention.

Figure 15:
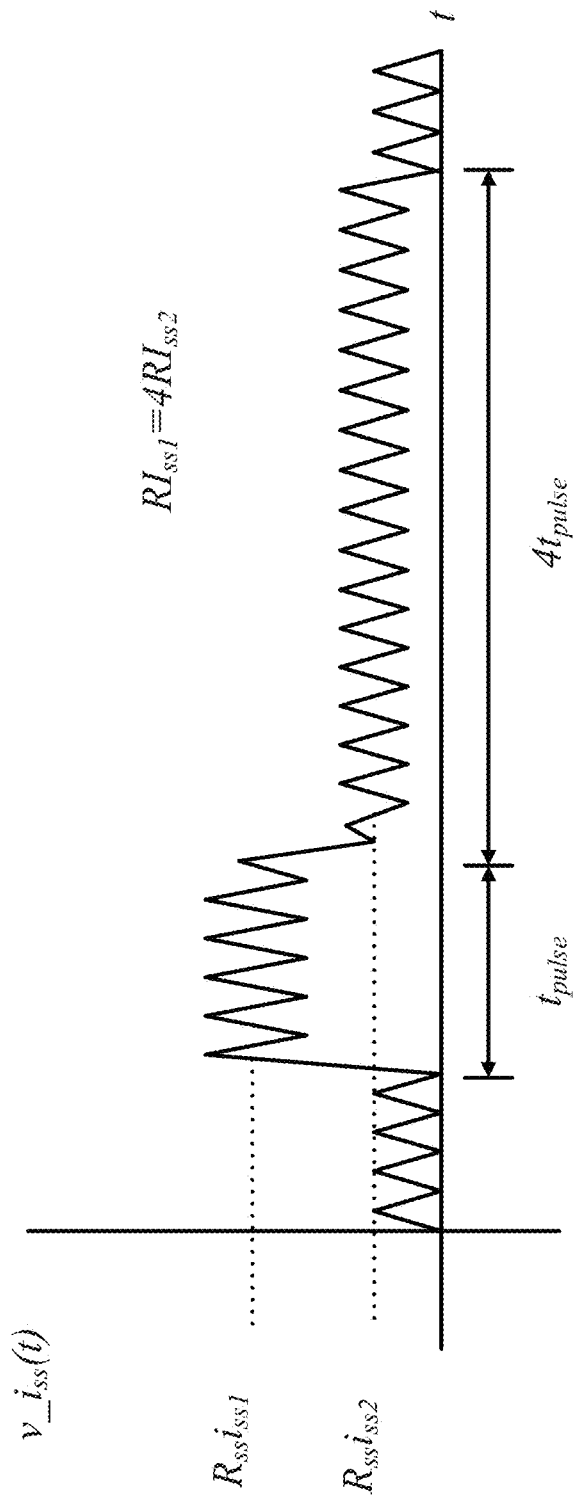
FIG. 15 is a plot of a current sensed from the second output power stage of FIG. 12, in accordance with one embodiment of the invention.

In the examples of FIGS. 12 and 13, the switched capacitor circuit 1204, 1304 (discussed in greater detail below) changes the polarity of the load current, which can result in a sensed current as shown in FIG. 15 (signal references from the embodiment of FIG. 12 used for simplicity) and which may inhibit effective control of the system's output. Namely, in practice, operation of the sensing circuit 1208, 1308 may be affected by the ripple from the output capacitor ($C_{out}$) and the switched capacitors 1204, 1304, as well as the sensed value changing over the course of the current pulse. For instance, the switched capacitor circuit 1204, 1304 may change the polarity of the load current practically instantaneously. With hysteretic control, to keep the load current regulated at the right level, the reference value may change just as quickly throughout the pulse, which may be difficult to do without a very fast DAC.

Figure 16:
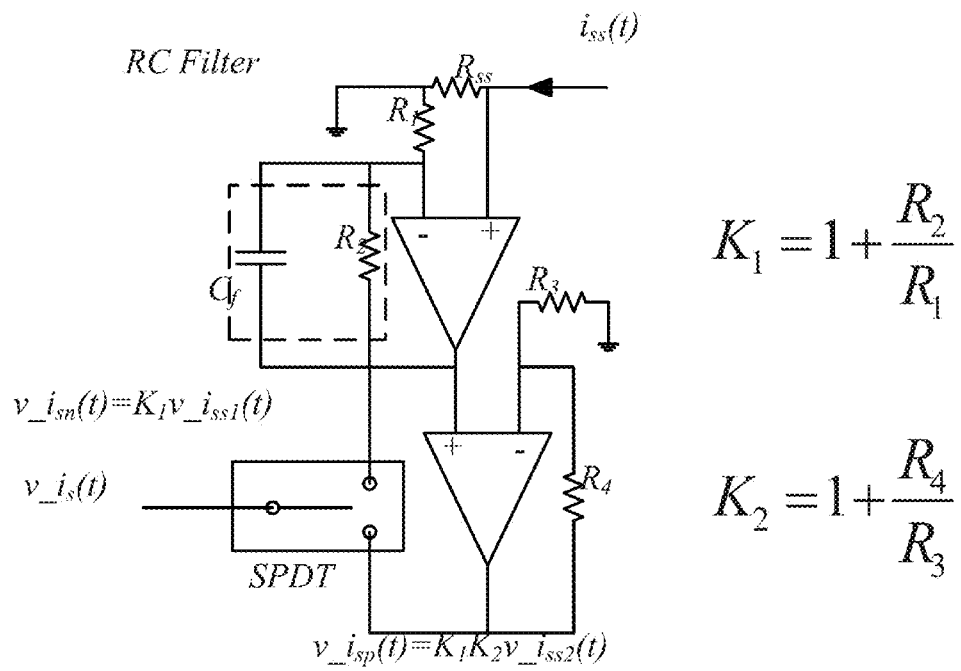
FIG. 16 is a schematic diagram of an exemplary sensing circuit for use in controlling an output of the second output power stage of FIG. 12, in accordance with one embodiment of the invention.

In one embodiment, both of these issues may be resolved via the sensing circuit shown in FIG. 16, which references circuit components and signals consistent with those depicted in FIG. 12 for the sake of simplicity, but which may be readily implemented in the context of the embodiment of FIG. 13, as will be readily appreciated by the person of ordinary skill in the art. In this example, excessive ripple may be resolved by placing an RC filter across the first gain stage of the amplifier in this circuit, wherein the corner frequency may be chosen such that the ripple frequencies are diminished. The RC time constant may be kept sufficiently small such that the waveform is not attenuated too much and the settling time between each stage is minimal.

Figure 17:
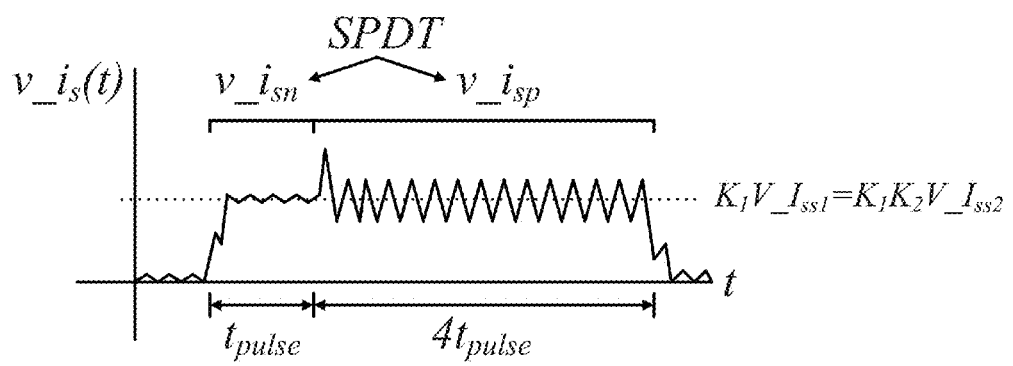
FIG. 17 is a plot of a sensed current obtained using the exemplary sensing circuit of FIG. 16.

To address potential issues associated with the quick changes in the sensed current value, a second gain stage can be introduced. The gain in these stages may be chosen to normalize the average sensed current over the two phases in order to be able to keep the reference current substantially constant throughout the entire pulse. This may be accomplished by choosing a suitable gain $K_1$ for the first amplification stage for the negative going current phase ($i_{sn}$) and adjusting $K_2$ such that during the positive going current phase the output of the second stage ($i_{sp}$) is on the same level as the first stage negative current phase. In the above examples, where $I_{ss1}=4I_{ss2}$, $K_2$ can be set to 4. Using a single pole double throw (SPDT) analog switch, $i_{sn}$ may be chosen as the sensed current during the negative pulse phase and switched to $i_{pn}$ during the positive phase. Sample results are shown in FIG. 17.

Based on the above, using the sensing circuit as shown in FIG. 16 in the context of the embodiments of FIG. 12 (or 13), the reference current may be held constant during the pulse sequence, thus allowing for a slower DAC to be used and increasing the effectiveness of the hysteretic controller.

Figure 18:
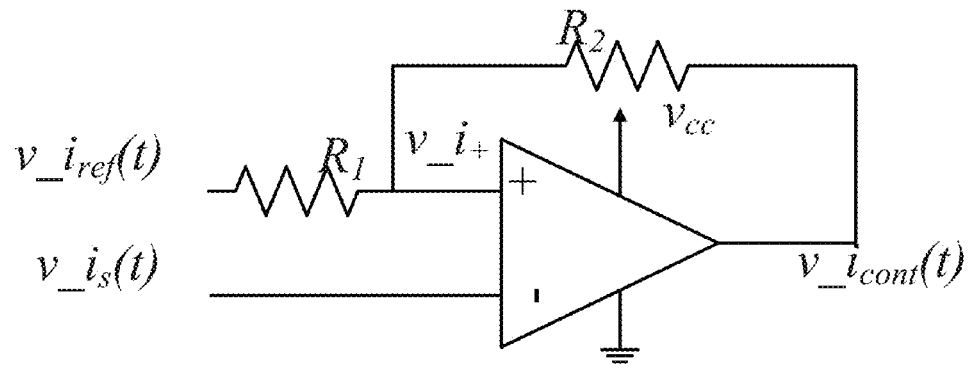
FIG. 18 is schematic diagram of an exemplary hysteretic comparator circuit for use in controlling operation of the second output power stage of FIG. 12.

With reference to FIG. 18, and in accordance with one embodiment, the hysteresis may be added by positive feedback to a comparator. This may be accomplished by adding two resistors: one at the positive input ($R_1$) and one between the positive terminal and the output ($R_2$), for example.

Figure 19:
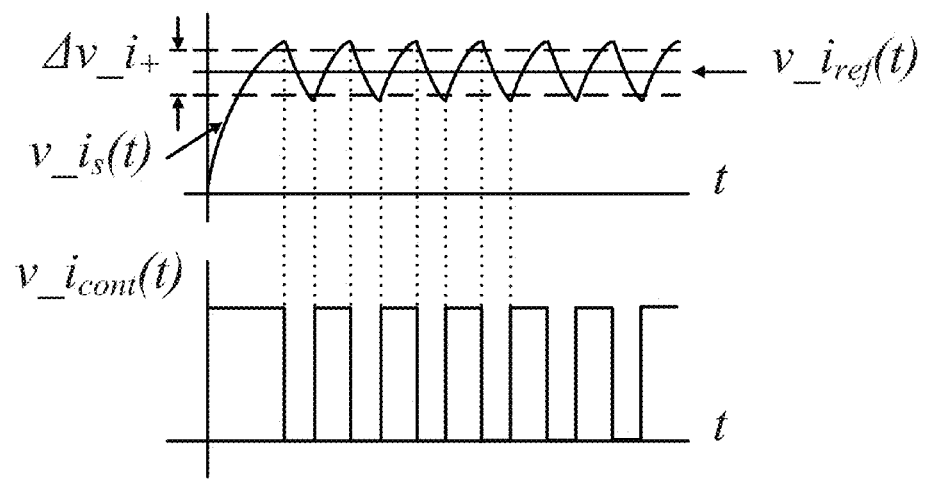
FIG. 19 is a plot of a waveform and subsequent control output of a comparator used in controlling an output of the second output power stage of FIG. 12.

The amount of hysteresis may be described by the following simplified relationship:

$$\Delta v_+ \cong v_{cc} \frac{R_1}{R_2}$$

which hysteresis may generate a suitable margin that defines the operating output current variation. The resulting comparator waveform and subsequent control output are illustrated in FIG. 19.

With particular reference to FIG. 12, the control signal (Vcont) from the comparator 1210 may be fed to the dead time logic 1212 to generate the two control signals (c1, c2) for the buck switches. In one embodiment, dead time may be added between the signals to prevent shoot through of the two buck switches. A similar system is more generically depicted in the embodiment of FIG. 13, wherein a hysteretic comparator 1311 is adapted to compare a value representative of a sensed current value (VGs[n]) with high and low reference values (Vref_low[n], Vref_high[n]) and output control signals (complow[n], comphigh[n]) to a switch signal generator 1316 configured to control activation of the buck converter's main and secondary switches, discussed above.

It will be appreciated that other types of controllers, control sequences and techniques may be readily applied in the present context, without departing from the general scope and nature of the present disclosure. Examples may include, but are not limited to, average current program mode control and other two-feedback loop based implementations where the current and the output voltage of a power stage are regulated simultaneously.

Pulse Generating Circuit

As discussed above, tight and fast regulation of the load (or pulse) current may be achieved, in accordance with some embodiments, via hysteretic control of the second output power stage. However, to produce bipolar asymmetric pulses, for example, stimulation must generally be switched from a positive/negative current at a given amplitude, followed by a current of the opposite polarity at a fraction of this amplitude (e.g. from I to −¼I in one example). To achieve this change within a relatively limited time frame (e.g. within 3 µs or less in some embodiments), while hysteretic control may be applied to regulate the load current within the desired rise time, voltage regulation may not be so readily achieved. For example, since the load is considered constant within an individual current pulse, the voltage would have to change at the same rate (e.g. from V to ¼V in less than 3 µs), which is not readily achievable using conventional control techniques. Accordingly, in order to achieve the desired pulse response time while changing the direction of the current, a fast-switching pulse generating circuit is used, such as the switched capacitor circuits shown generically in FIGS. 12 and 13, to change the voltage and current direction of the load quickly. For example, in one embodiment, the pulse generating circuit should quickly change the amplitude of the voltage V to ¼V as well as the direction of the current flow to the load.

In one embodiment, the pulse generating circuit comprises a positive and a negative stimulation path, each path comprising a respective charging element and activation switch serially encompassing output nodes to electrode leads for stimulating a given tissue area of interest. In such embodiments, each respective charging element, which may consist of one or more capacitive elements or the like, is charged by the device's voltage supply and, upon activating a respective switch, is discharged to generate positive and negative current pulses, respectively. Using this approach, the polarity of the stimulation pulses may be switched rapidly to achieve desired bipolar stimulation characteristics. For example, in one embodiment, the corresponding pulse rise time may be predominantly dictated by a switching speed of the switches, which may be significantly faster than what may be otherwise available via conventional systems.

In the provision of asymmetrical stimulation, and as will be described in greater detail below, characteristics of the respective charging elements (i.e. a ratio of respective capacitor ratios, for example), may dictate, at least in part, an amplitude ratio of the applied pulses, whereby sequential activation of the respective activation switches alternates pulse polarity in accordance with a preset current pulse amplitude ratio. By applying appropriate control timing to switch activation, a pulse duration ratio inversely proportional to the pulse amplitude ratio can be achieved thus resulting in substantially balanced bipolar current pulse stimulation (i.e. with substantially zero net charge accumulation in the tissue) as an inherent feature of the circuit design. These and other advantages of the herein described pulse generating circuits will be described in greater detail below.

FIGS. 20 to 23 provide different examples of a switched capacitor circuit usable in the present context to achieve intended results. It will be appreciated that these circuits provides examples only, and that variations thereto (e.g. including additional capacitors, switches and the like) may be considered herein without departing from the general scope and nature of the present disclosure.

Figure 20:
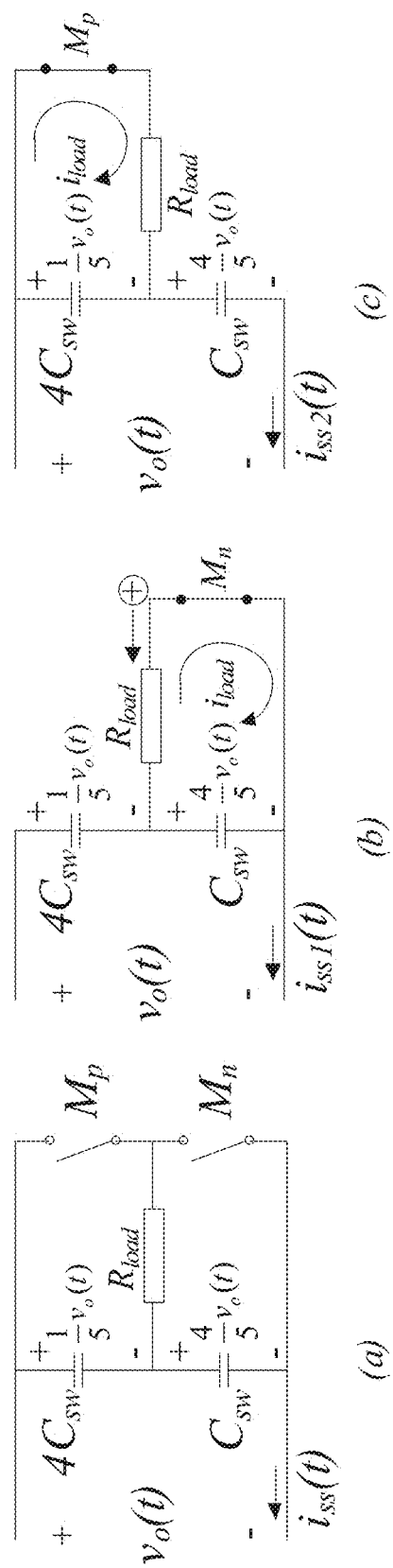
FIG. 20 is a schematic diagram of a switched capacitor pulse generating circuit, in accordance with one embodiment of the invention, showing in (a) a general configuration of the circuit, (b) an effective configuration of the circuit in generating a negative current pulse, and (c) an effective configuration of the circuit in generating a positive current pulse.

Referring now to the exemplary embodiment of FIG. 20, the switched capacitor circuit, in this implementation consists of a two switch, two capacitor circuit, wherein FIGS. 20b and 20c depict the possible modes of the switched capacitor circuit shown in FIG. 20a.

The circuit generally works on the basic capacitor charge equation Q=CV. The charge on both capacitors must generally be the same by capacitor charge balance. Therefore, by adjusting the capacitance ratio of the two switched capacitors, the voltage levels on each capacitor are inversely affected. Using a 4:1 ratio for the capacitors in this example, the switched capacitor circuit effectively quarters the voltage across the load from one phase to the next. In FIG. 20b, the first negative current phase (i.e. negative stimulation path or loop) is illustrated where 4/5 of the buck output voltage is connected across the load. In order to achieve this, the low side switch Mn is active for the desired pulse time, tpulse. After this phase, some dead time is generated to prevent shoot-through current in the switches, followed by the positive current phase in FIG. 20c (positive stimulation path or loop), where 1/5 of the buck output voltage is connected across the load. In this manner, the voltage across the load is quartered practically instantly while changing the direction of the current through the load.

One further advantage of the switched capacitor circuit discussed above is that in either arrangement—positive or negative current—there is always a blocking capacitor in series with the load, which may prevent charge from accumulating on the skin. Therefore, the risk of having charge develop on the individual/patient if the pulse durations and/or phase amplitudes are not completely cancelled during the two phases is reduced. This arrangement, while particularly simple, is quite effective and has safety features built into it, which makes it particularly suitable for FES systems.

Figure 21:
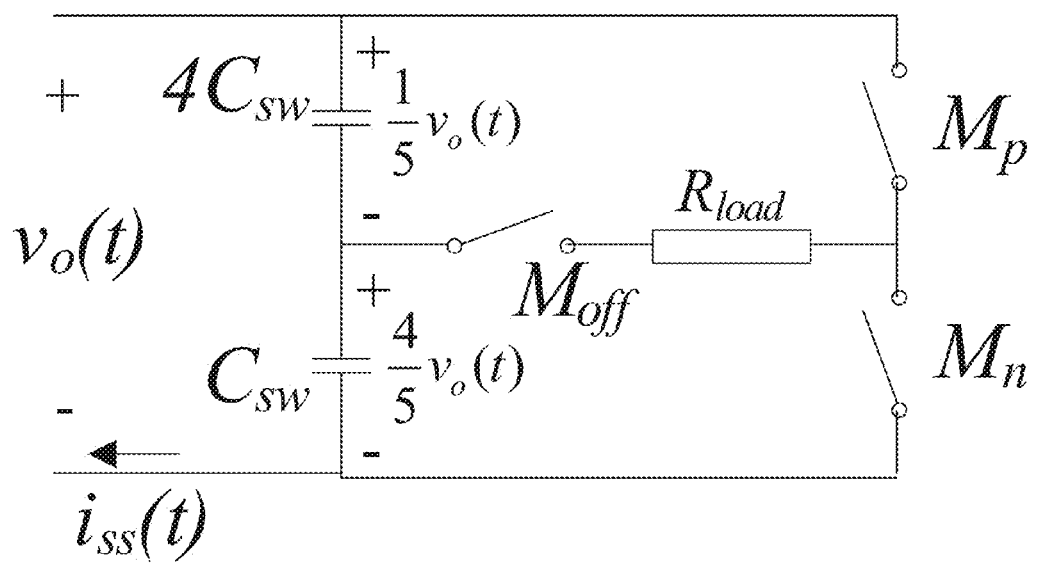
FIG. 21 is a schematic diagram of a switched capacitor pulse generating circuit, in accordance with another embodiment of the invention.

With reference to FIG. 21, and in accordance with another embodiment of the invention, an alternative switched capacitor circuit is shown for use in the present context, for example, to be implemented distinctly from or integrally with a second power stage of an FES system, such as a buck converter as shown for example in FIGS. 12 and 13. In this example, and in order to increase patient safety, the switched capacitor circuit is modified relative to that depicted in FIG. 20 by including an extra switch $M_{off}$ between the load and the two switched capacitors. In the embodiment shown in FIG. 20, when both $M_n$ and $M_p$ are off between pulses, there may be a floating voltage on the load which could find a way to ground through the patient. The extra switch $M_{off}$, as shown in FIG. 21, could thus be active during the pulse sequence and be shut off at all other times in order inhibit a floating voltage at the node between the switched capacitors. Namely, the embodiment shown in FIG. 21 may provide that current only flows to the patient during pulses, and not otherwise, which may present an additional safety advantage.

Figure 22:
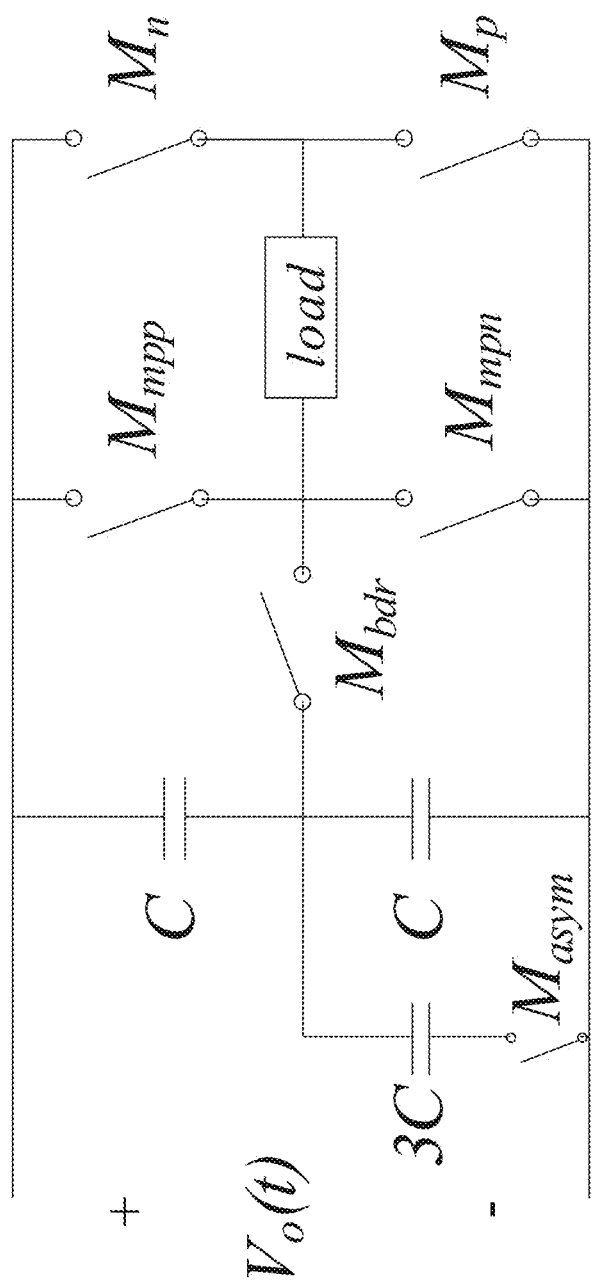
FIG. 22 is a schematic diagram of a switched capacitor pulse generating circuit, in accordance with another embodiment of the invention, selectively configured for monopolar, bipolar symmetric and bipolar asymmetric operation.
Figure 23:
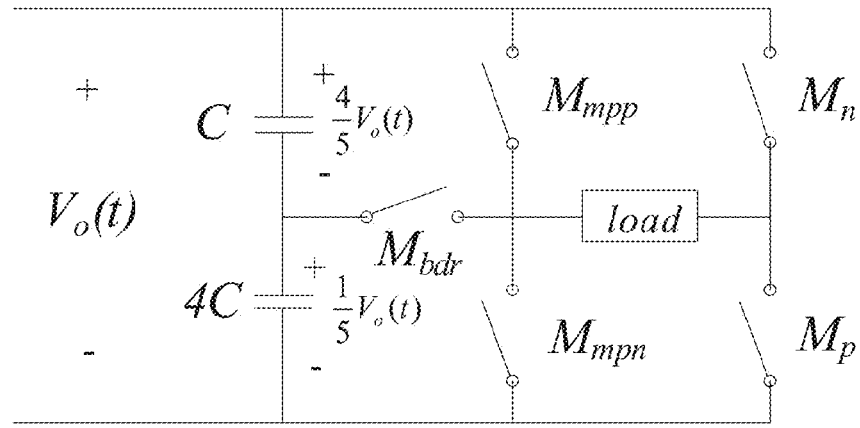
FIG. 23 is a schematic diagram of the switched capacitor pulse generating circuit of FIG. 22, showing in (a) a general effective configuration of the circuit for bipolar asymmetric operation, (b) an effective configuration of the circuit in generating a negative current pulse, and (c) an effective configuration of the circuit in generating a positive current pulse.
Figure 23:
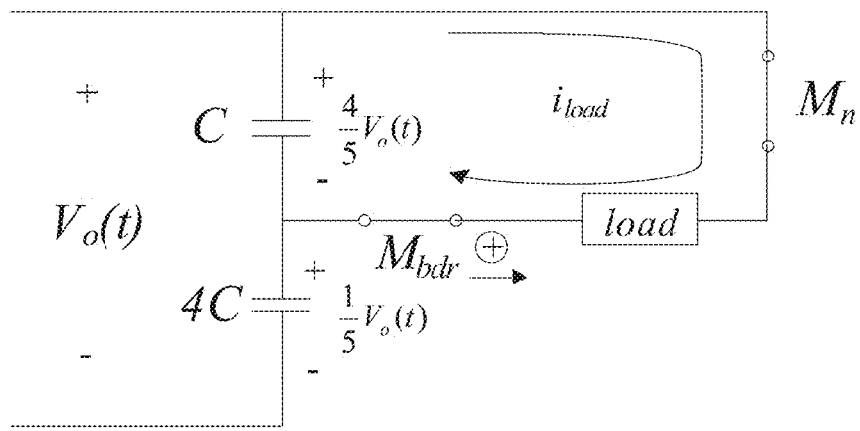
Figure 23:
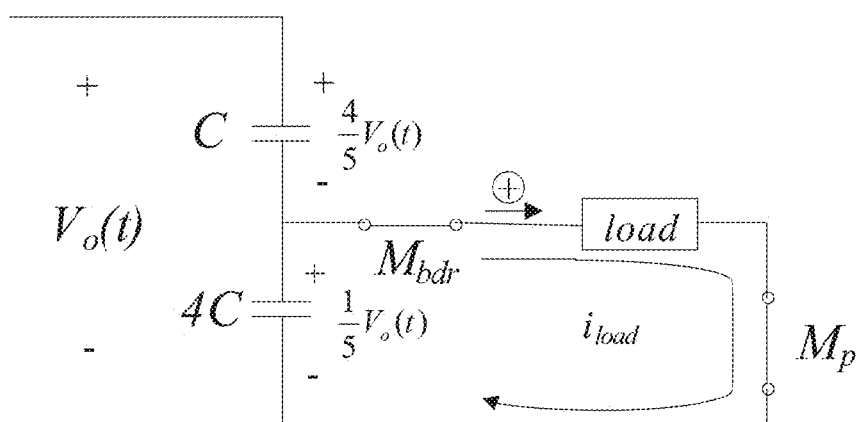

With reference to FIG. 22, and in accordance with another embodiment of the invention, an alternative switched capacitor circuit is shown, again for use in the present context as outlined above. In this embodiment, the circuit is extended to allow for greater operational flexibility, namely in allowing for use in both symmetric and asymmetric bipolar activation, as well as monopolar activation. For instance, upon selectively activating the additional switch $M_{asym}$, the circuit may be selectively activated to implement a 4:1 pulse amplitude ratio for bipolar asymmetric stimulation (as discussed above and as shown schematically in FIG. 23), or a 1:1 pulse amplitude ratio for bipolar symmetric stimulation. On the other hand, upon selective activation of the additional switches $M_{mpp}$ and $M_{mpn}$, monopolar stimulation may be implemented, as may be desired in certain FES applications.

As will be appreciated by the skilled artisan, other switch and/or capacitor configurations may be considered herein to provide similar effects and/or pulse stimulation diversity, without departing from the general scope and nature of the present disclosure. For example, additional capacitors may be included to further diversify the availability of asymmetric stimulation ratios, and/or additional switches included to further diversify activation of such diverse stimulation ratios and/or different stimulation sequences and the like Furthermore, it should be noted that other implementations effectively resulting in a serial connection of a capacitor and the stimulated tissue can be used in a similar manner, and resulting, in some embodiments, in the substantial elimination of the DC component from the generated pulses thus effectively achieving zero accumulated charge for bipolar pulses, and/or other related advantages. Such alternatives are considered to fall within the scope of the present disclosure.

The above-described embodiments provide various advantages not only in operation flexibility and efficiency, but also patient safety. For example, in either arrangement (positive or negative current), a blocking capacitor is always disposed in series with the load, which may prevent charges from accumulating on the skin during bipolar stimulation without the use of specific discharging circuits. Accordingly, the risk of having charge develop on or in the tissue if the pulse durations and/or phase amplitudes are not completely balanced during the two phases can be mitigated. Furthermore, with reference to the embodiments of FIGS. 21 and 22, the load can be fully disconnected from the output capacitors when pulses are not being administered, namely by deactivating the bidirectional switch $M_{off}/M_{bdr}$. Also, the two ends of the load can be discharged fully after the pulse is administered, e.g. via $M_{mpn}$ and $M_p$ in FIG. 22). These arrangements, while particularly simple, are quite effective and have different safety features built into them, which makes them particularly suitable for FES systems.

With added reference to FIGS. 12 and 13, an output capacitor, which may range up to several hundred μF, may also be provided in addition to the switched capacitors of the pulse generating circuit, which may be several μF. Using this additional capacitor may allow, in some embodiments, to address potential issues with respect to switched capacitor sizing, ripple and/or safety, for example. For instance, in an embodiment that does not include an output capacitor, as shown for example in FIGS. 12 and 13, much larger switched capacitors may be required to achieve desired results. For example, a 200 μF low side switched capacitor would result in an 800 μF high side capacitor, which is much larger than would otherwise be required upon using a relatively large output capacitor. Therefore the size of these two capacitors is much larger than the three capacitor setup. Similarly, if the output capacitor is removed, the series switched capacitors may result in a capacitance that is less than the original output capacitor, which may increase voltage ripple. Finally, if large capacitors are used for the switched capacitors, they would store more charge than otherwise when using an output capacitor, which may present some safety concerns in the event of a device malfunction; accordingly, by reducing the energy storage in the switched capacitors, as provided by the three capacitor configuration, patient safety may be increased.

Overall, the system presented here produces all the pulse types needed for sophisticated FES applications. It uses SMPS arranged in series with merged switched capacitor circuitry to shape the pulses. Further, it monitors both current and voltage in several ways to ensure tight regulation of pulse characteristics and safe stimulation for patients.

It will be appreciated that alternative measures may be implemented in adapting control sequences and circuitry to the different embodiments, and that, without departing from the general scope and nature of the present disclosure.

As shown above, and as further demonstrated by the examples below, different embodiments of the invention herein described may, for example, promote sustainable implementation and wider adoption of emerging FES applications that are presently only available as research tools given the deficiencies and drawbacks of know devices, as described above. For instance, when compared to the current solutions, the systems considered herein in accordance with different embodiments of the invention can provide significantly lower power consumption and a wider range of pulse patterns. Furthermore, pulses can be produced with reduced heat dissipation, which may thus allow for system miniaturization and a longer battery life, thus improving the portability of the FES system and, in some embodiments, allowing for on-chip implementation of a complete system, for example. Also, some embodiments may provide simultaneous pulses over multiple channels.

Furthermore, the device described herein in exemplary embodiments may provide improved pulse rise times and more accurate amplitude and duration control. These faster rise times may allow the potential to achieve the same tissue stimulation results with less current. This may in turn reduce the stress on the individual (i.e., perception of pain or discomfort) as well as drastically increase the operating time of the stimulator (i.e., decreases the energy consumption of the stimulator). The rise time, in combination with the accurate amplitude and duration control also may provide that over time no charge will be built up in stimulated tissues, which can be an important aspect for FES applications, especially for applications involving implanted FES systems.

In some embodiments, the slew rate of the pulses produced by the herein described systems and designs are significantly faster than the 1 μs slew rates common to existing devices and systems. For example, in one embodiment, a pulse slew rate of no more than 500 ns is achieved. In accordance with another embodiment, a pulse slew rate of no more than 100 ns is achieved. In accordance with yet another embodiment, a pulse slew rate of no more than 80 ns is achieved. In accordance with yet another embodiment, a pulse slew rate of no more than 50 ns is achieved. In accordance with yet another embodiment, a pulse slew rate of no more than 20 ns is achieved. In accordance with yet another embodiment, a pulse slew rate of no more than 10 ns is achieved. Accordingly, the pulse slew rates may, in some embodiments, be as much as two orders of magnitude faster than conventional systems.

In one embodiment, the fast rise time is a result of the output circuit changing the connection of electrodes, which are in one instant connected to one capacitor and in the following to the other. Since the capacitors in these embodiments can have different voltage levels (i.e. asymmetric implementation) and polarities (bipolar implementation), the pulsed signal can be changed practically instantaneously, thus effectively limiting pulse rise times to the speed of the switches. Accordingly, by implementing the above-described circuits using faster switches, faster pulse rise times may also be achieved.

In one embodiment, such rise times allow for a significant improvement over conventional devices commonly providing pulse rise times upwards of 1 μs. In doing so, increased responsiveness may be triggered in the stimulated tissue, thus allowing, in some embodiments, for a reduction in pulse amplitudes than would otherwise be necessary. In one example, improved responsiveness in the application of bipolar pulses may allow for up to a five-fold reduction in applied current pulse amplitudes. For example, where 30 mA pulses may have otherwise been applied for 250 μs, 7.5 mA pulses may applied using an embodiment of the invention herein described. These values provide an example only of applicable pulse durations and/or amplitudes; it will be appreciated that various pulse parameters may be considered herein without departing from the general scope and nature of the present disclosure.

In one embodiment, the provision of such improved pulse rise times may also or alternatively allow for a reduction or minimization of physical discomfort experienced by a patient as a result of the pulse stimulation. For example, by applying a reduced charge to the stimulated tissue, or again by achieving greater tissue responsiveness, treatments implemented using the herein described device may reduce, if not completely avoid patient discomfort.

Also, in accordance with some embodiments, the output stage of the herein described systems and designs can operate with substantially zero charge accumulation in bipolar mode, thus substantially eliminating the need for the additional discharging circuits commonly found in existing solution. In some embodiments, the output stage of the herein described systems and designs may offer one or more layers of safety features such as tissue overvoltage and overcurrent protection, as well as tissue impedance monitoring, to name a few.

As will be appreciated by the skilled artisan, the highly flexible architecture of the above-described embodiments and below-provided examples may be particularly suitable for the implantation of battery-powered external functional electrical stimulators (FES) and neuroprostheses, and readily amenable to emerging sophisticated FES applications, such as closed-loop controlled and brain machine interfaced neuroprostheses, for example, as well as various other applications.

Example 1

Figure 24:
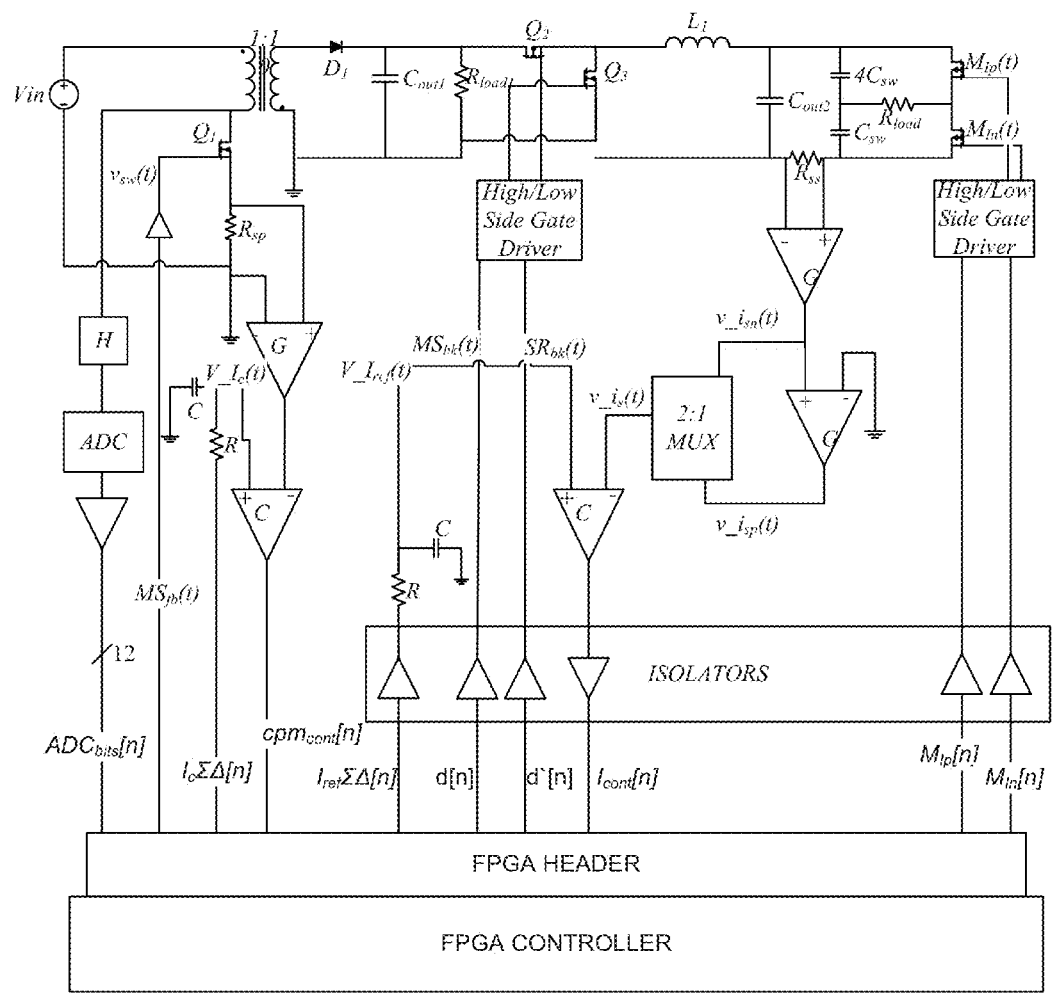
FIG. 24 is a detailed schematic diagram of an exemplary output stage of a FES device, in accordance with one embodiment of the invention.

This example provides experimental results for an exemplary embodiment of the device. In this exemplary embodiment, an SMPS FES system is provided as a single channel stimulator comprising two power stages, a switched capacitor output circuit and a digital block including a controller for the flyback convertor, and circuitry for the buck and switched capacitor output. The flyback is generally configured to operate using current programmed mode (CPM). The flyback generally establishes a high voltage output that feeds into the buck converter which in turn scales it down to the necessary level. Finally, to construct the output current pulses, the switched capacitor circuit quickly changes the voltage level and current direction. A hysteretic control is used to control the buck duty cycle. The converter and output blocks were designed and implemented on printed circuit board (PCB), a schematic of which is depicted in FIG. 24, and the digital portion was implemented using an Altera DE2 FPGA development board.

The operability of this exemplary embodiment was first simulated for each part of the design, starting with an open loop simulation of the flyback followed by simulation of the switched capacitor circuit, and finally the entire system was simulated in open loop to verify pulse waveforms. The simulation tools used were Matlab simulink with PLECS and SIMetrix.

Figure 25:
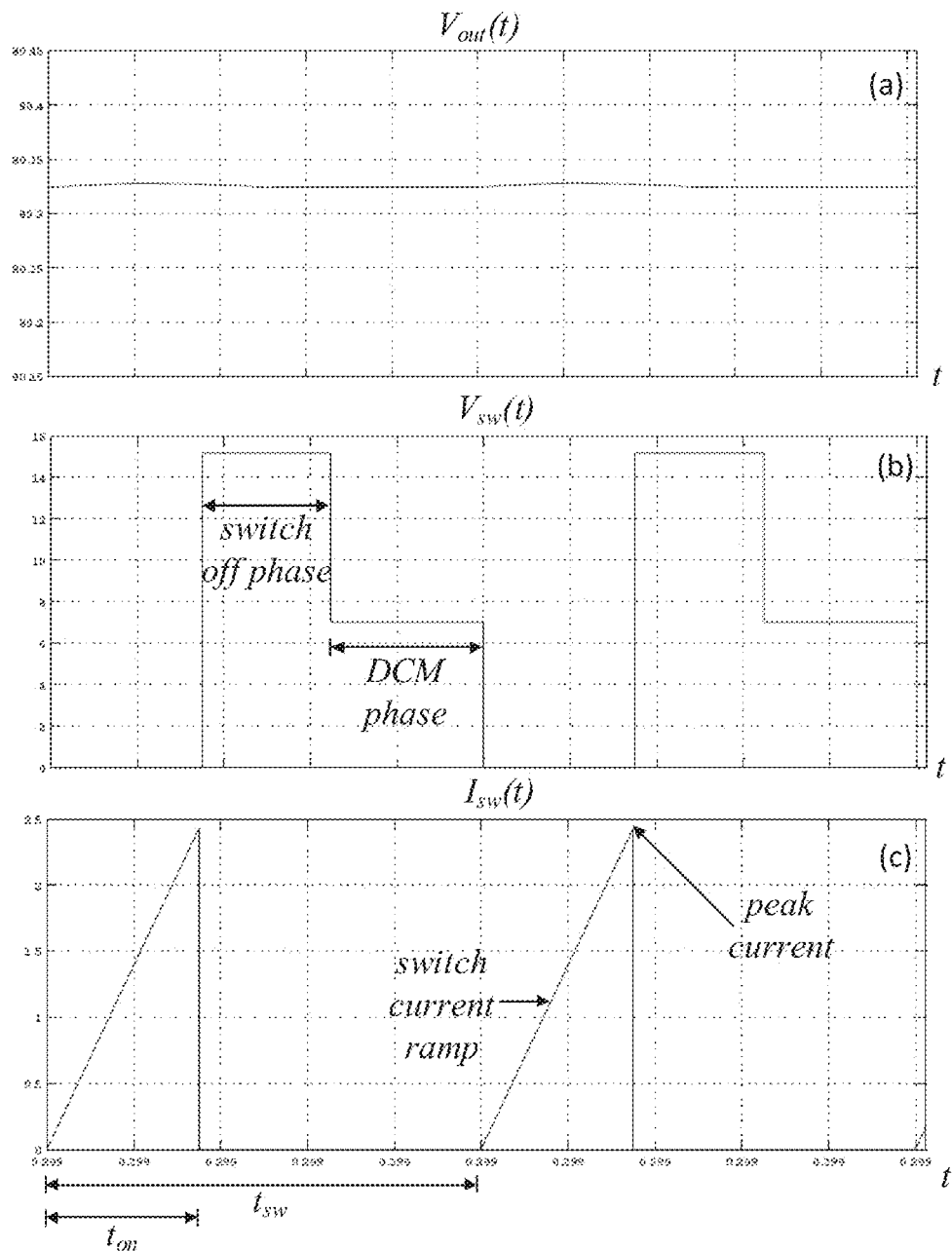
FIG. 25 is a plot of a simulated waveform for an open loop flyback converter, in accordance with the embodiment of FIG. 24.

The flyback was simulated using a transformer base with added magnetic inductance and some parasitic components in Matlab using PLECS. FIG. 25 shows the results of the 1:10 turns flyback converter with a 26% duty ratio in open loop. The waveforms used in controlling the circuit are the switch voltage and current. FIG. 25a shows the output voltage, which is kept substantially constant within a 15 mV margin. The switching frequency is 100 kHz, with an on-time of 2.6 μs. From the switch voltage in FIG. 25b, three distinct phases can be seen. An 'on' phase when the switch is active, an 'off' phase when the switch voltage ramps up to the value from Equation 3, and finally a DCM phase when the switch voltage takes on the value of the input voltage, in this case 7V. The current in the switch (FIG. 25c) takes the form of a ramp during the on time. This ramp is used in peak current control, when it is compared to the reference to establish the duty cycle.

Figure 26:
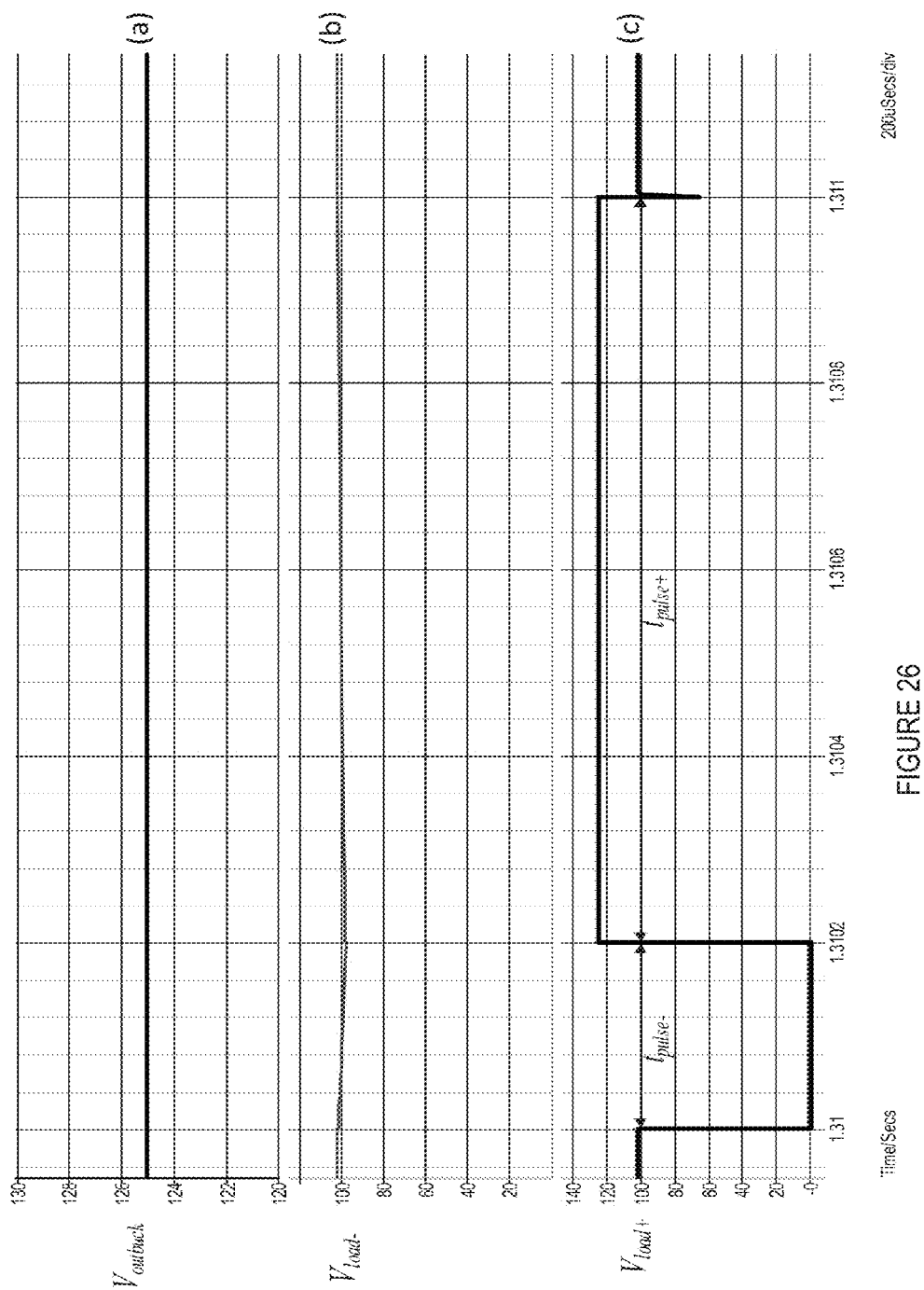
FIG. 26 is a plot of simulated waveforms for a switched capacitor circuit, in accordance with the embodiment of FIG. 24.

The switched capacitor circuit was simulated independently, using a constant supply voltage to simulate the buck output. The waveforms of FIG. 26 taken from SIMetrix show a 200 μs negative current pulse, followed by an 800 μs positive current pulse of one quarter the magnitude. In particular, plot (a) shows the Buck voltage, 2V/div., plot (b) shows the negative terminal of load voltage, 20V/div. and plot (c) shows the positive terminal load voltage, 20V/div. As discussed above, the output load current can be calculated by subtracting $V_{load+} - V_{load-}$ and dividing by the load resistance. In this case, the input voltage is 125V, so there is a 25V drop over the first switched capacitor and the remaining 100V is across the second switched capacitor. The output load resistance is 1 kΩ so the output current is found to be –100 mA for the first current phase followed by 25 mA during the second current phase. The amplitude proportions and pulse durations appear as expected. Also note that these waveforms are extracted without any kind of control. Therefore variations seen in the current levels can be regulated, as shown in the results below for the combined system.

Figure 27:
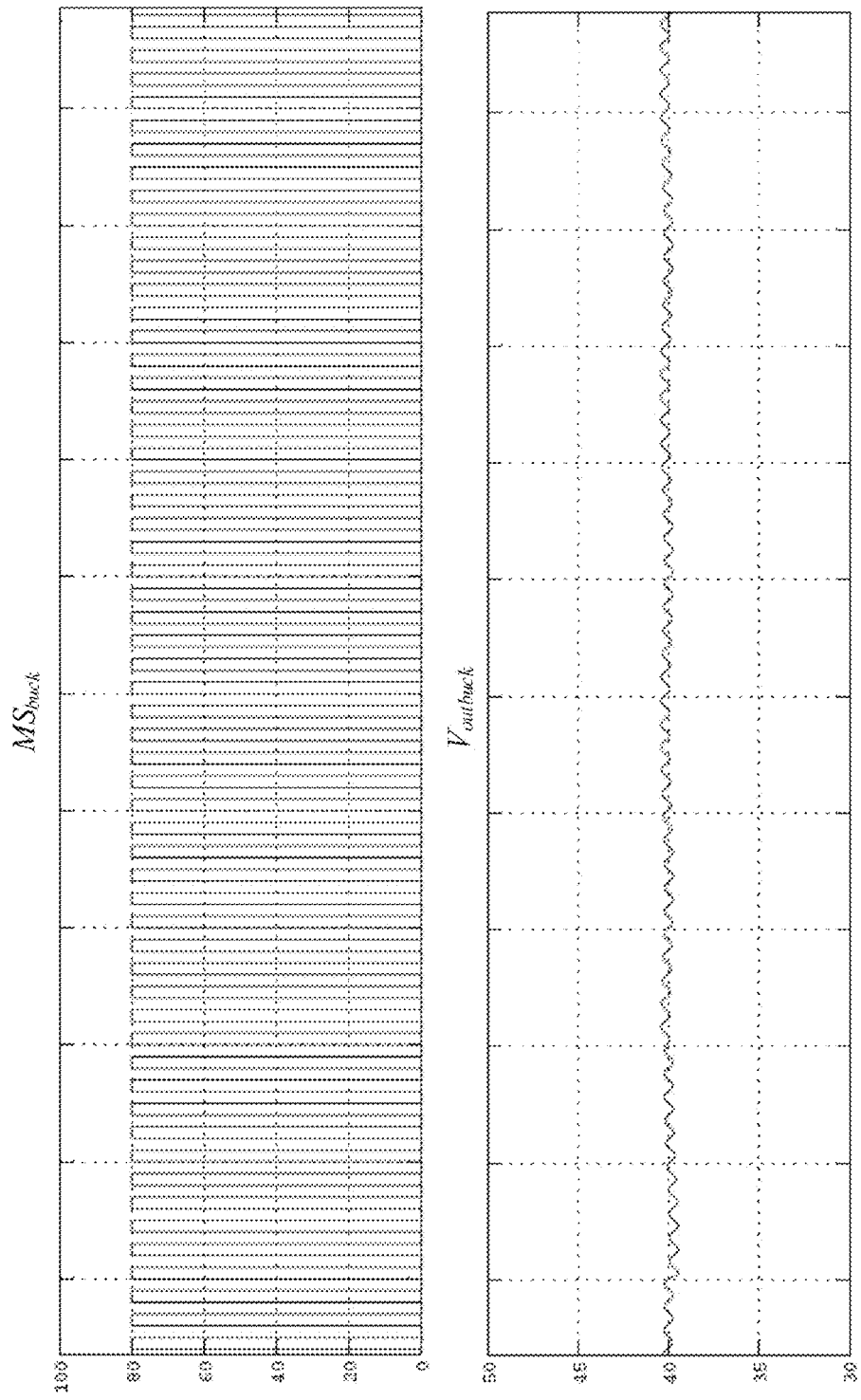
FIGS. 27 and 28 are plots of simulated waveforms for the output stage of FIG. 24.
Figure 28:
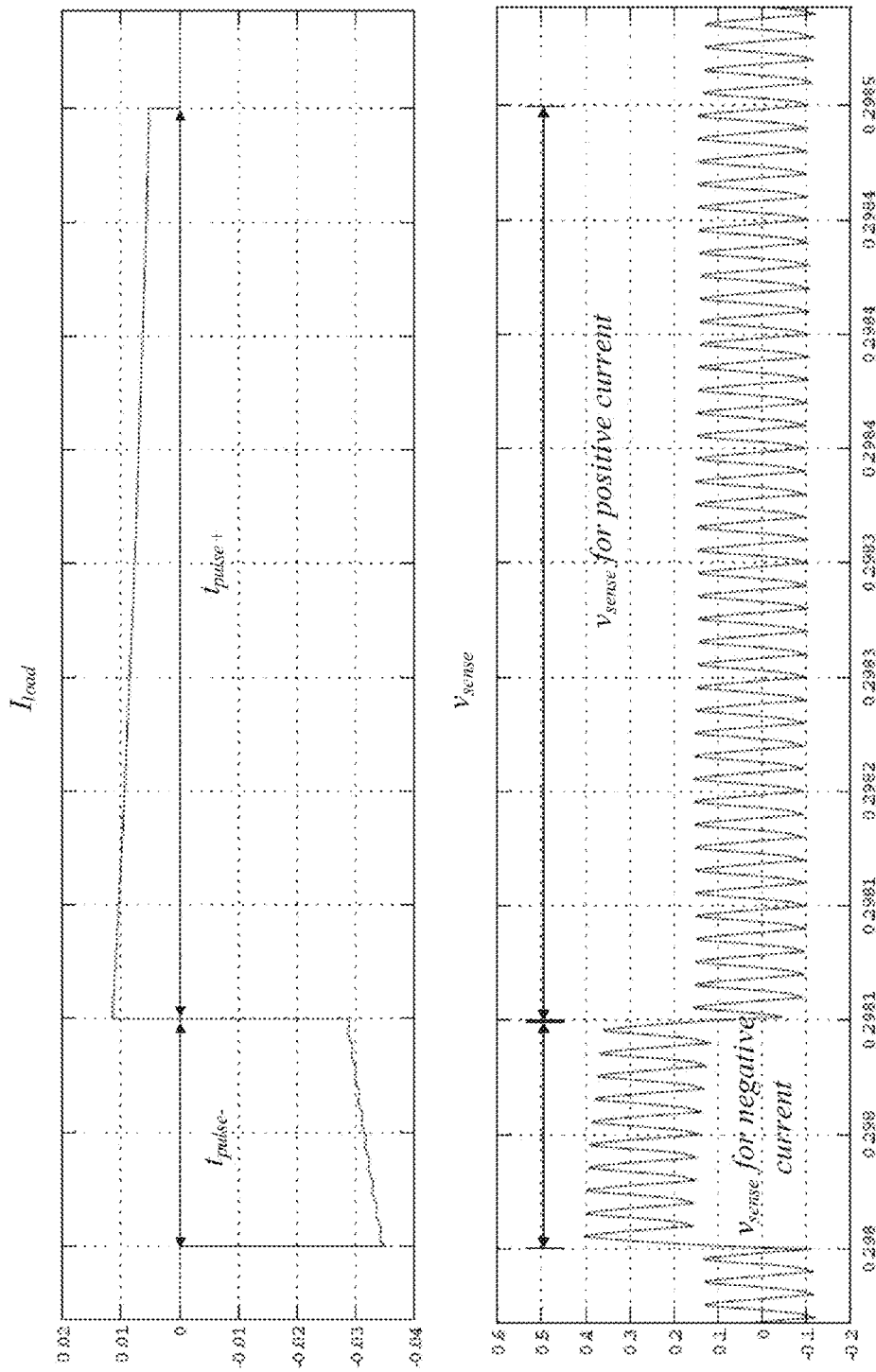

The entire system, including the flyback, buck and switched capacitor output was simulated in Matlab using PLECS. The results of this simulation are shown in FIGS. 27 and 28. With reference to FIG. 27, the top plot (a) shows the Buck main switch signal, 20V/div., whereas the second plot down (b) shows the Buck output voltage, 5V/div. With reference to FIG. 28, the top plot (a) shows the Load current, 10 mA/div., and the bottom plot (b) shows Sense resistor voltage, 100 mV/div.

The input to the buck is the 80.3V output from the flyback from FIG. 27. The buck is given a constant duty cycle of 50%, so the output of the buck to the switched capacitor circuit is approximately 40V. The load current shows the desired pulse shape. The negative current phase duration is 100 μs, followed by the positive phase of 400 μs. The pulse shape is close to the theoretical form and the sensed current waveform takes on two different levels as expected. The output current however shows a drop in each phase, which drop can be addressed, in accordance with one embodiment, via hysteretic control of the buck to regulate the output level. As discussed below, a controller used for closed loop system operation can remedy at least some of the issues raised by open loop simulation.

To validate this design, the complete system was fabricated using discrete components and a DE-2, FPGA Altera Evaluation Board as the digital controller. FIG. 24 provides a schematic of the fabricated prototype, in accordance with one embodiment of the invention.

Figure 29:
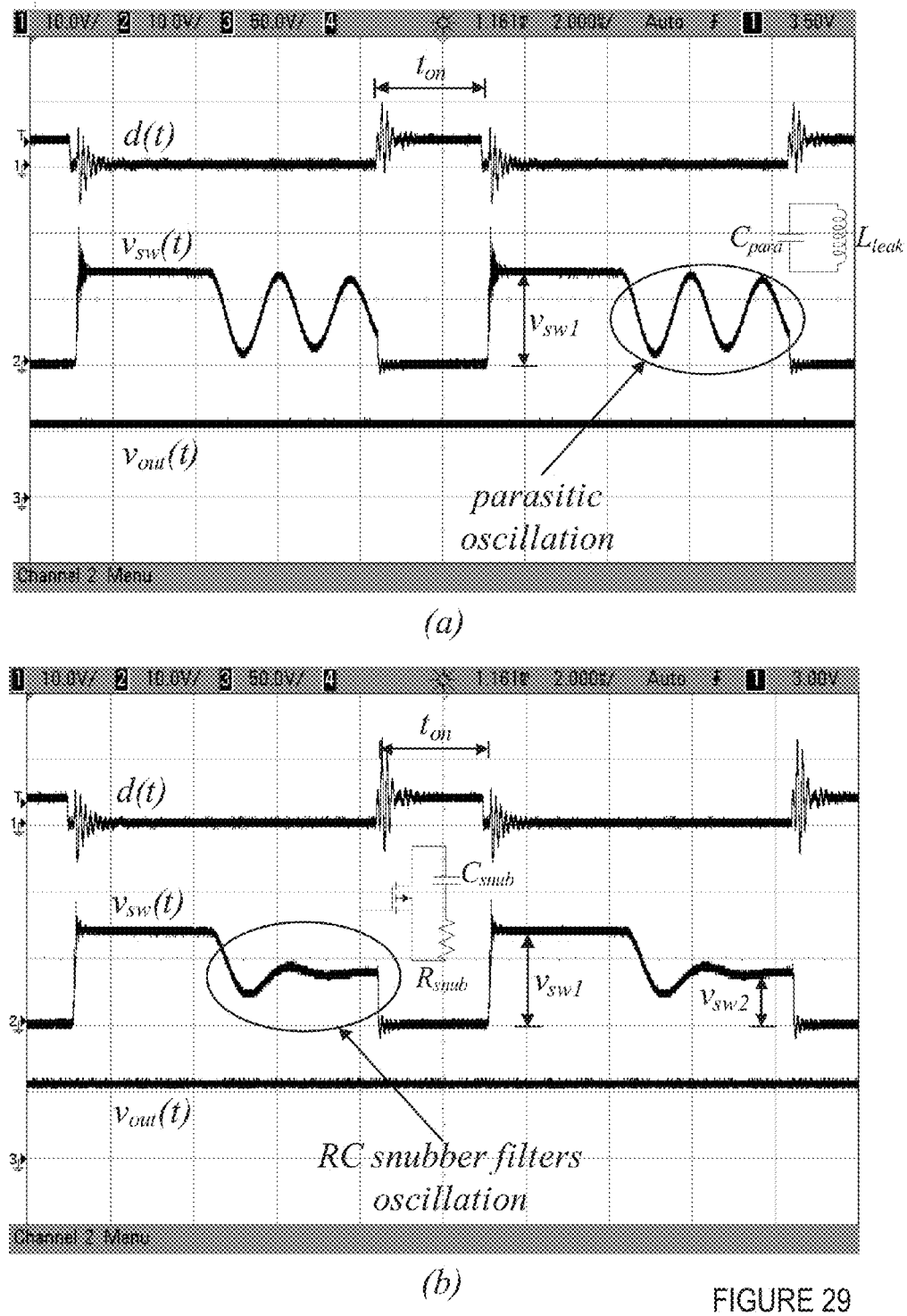
FIG. 29 is a plot of experimental waveforms for a flyback converter of the output stage of FIG. 24, showing ringing oscillations in (a), and the ringing being filtered by snubbers in (b)

With reference to FIG. 29, it is first observed that the fabricated flyback converter shows waveforms that vary from the simulated ones. In this example, the flyback is operated in open loop with 20% duty cycle. In FIG. 29a it is shown that the switch voltage exhibits ringing during the DCM phase due to the leakage inductance and parasitic capacitance of the transformer. This oscillation makes it impossible to discern the second switch voltage value, or $V_{in}$, properly. By adding a snubber circuit, a series RC in parallel with the switch, as shown in FIG. 29b, the oscillation is greatly diminished. This makes it possible to identify both the first switch voltage of 13.32V and the second switch voltage of 7V. Using Equation 3, these values produce the expected output voltage of 54V. FIG. 29 shows the Flyback switching voltage as follows: Ch1: duty cycle signal, 10V/div. Ch2: switch voltage, 10V/div. Ch3: output voltage, 50V/div. wherein in FIG. 29a the switch without snubber illustrates the ringing oscillation during DCM, which inhibits sensing input voltage ($v_{sw2}$), and wherein in FIG. 29b an RC snubber filters the ringing, enabling sensing of the second switch voltage.

With the correct switch voltage waveforms, the next step was to implement the CPM DCM peak current controller, which uses the switch voltage values to extract the output voltage and adjust for the difference between the desired reference value.

Figure 30:
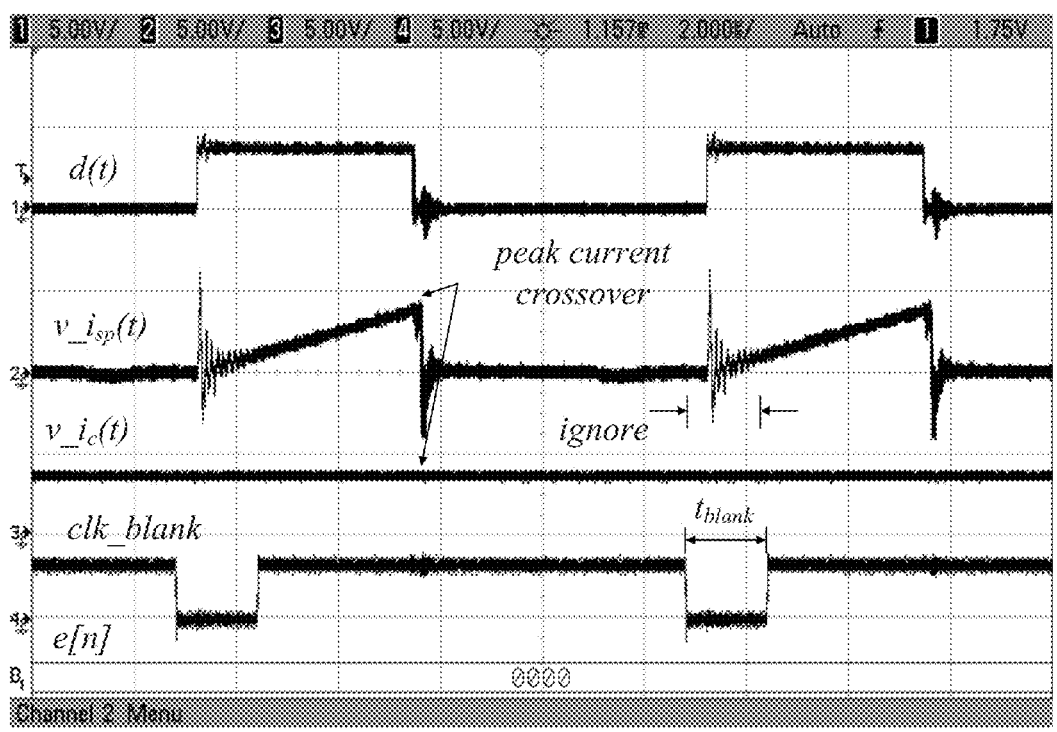
FIG. 30 is a plot of experimental waveforms for a flyback primary side CPM DCM control in steady state, in accordance with the embodiment of FIG. 24.

FIG. 30 shows various waveforms of the flyback controller in steady state under primary side CPM DCM control (Ch1: duty cycle signal, 5V/div. Ch2: primary side sensed current, 5V/div. Ch3: control reference, 5V/div. Ch4: blanking clock signal, 5V/div. Bottom: 4-bit error value).

The main switch is kept on until the sensed current $v\_i_{sp}$ reaches the reference level $v\_i_c$. At that point the main switch returns to zero until the next switching cycle. The blanking clock ignores initial ringing spikes in switch current seen at the turn on point. The digital error value is shown on the bottom, which indicates zero error, implying stable steady state conditions.

Figure 31:
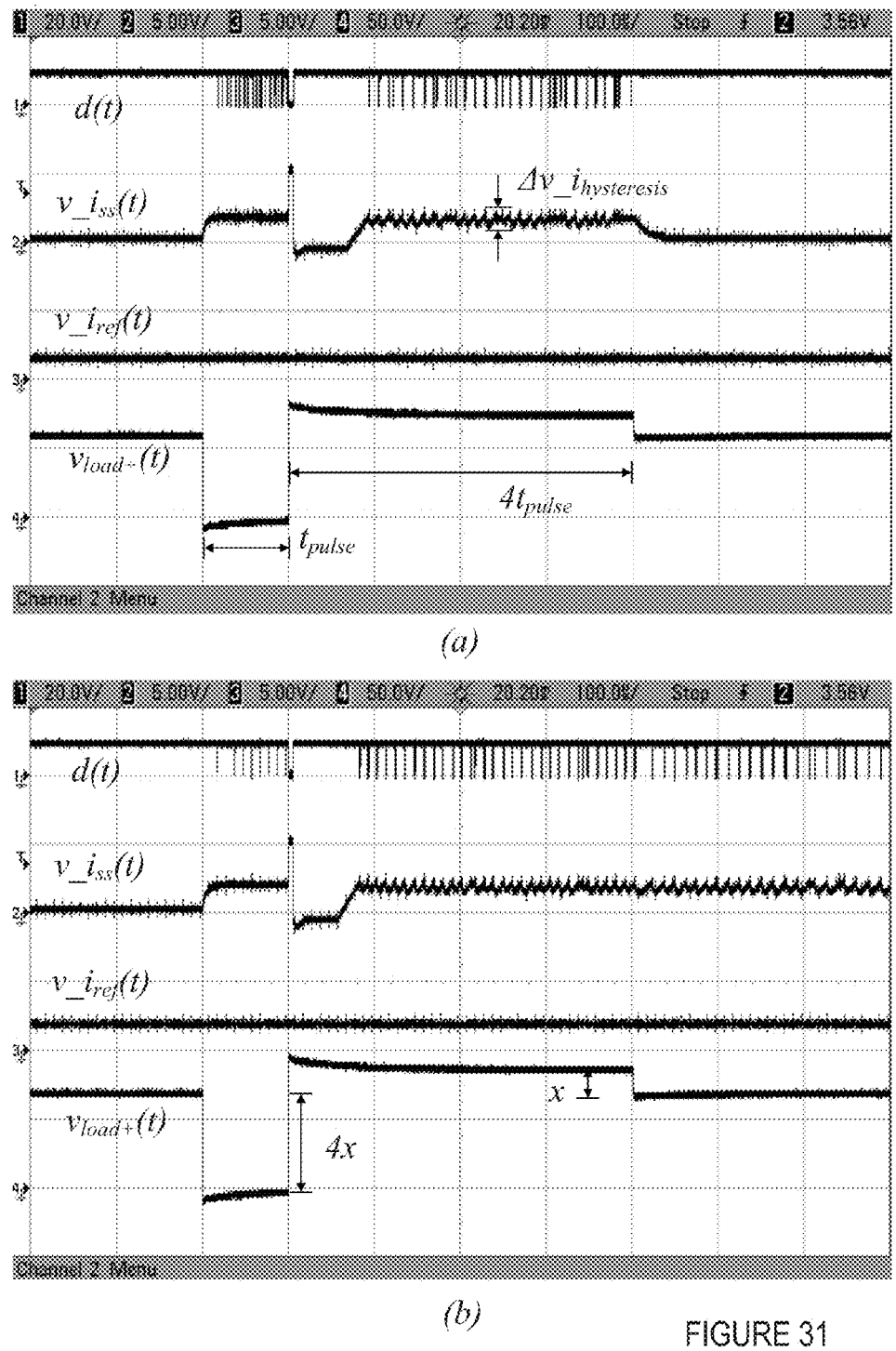
FIG. 31 is a plot of experimental current pulse waveforms generated by the output stage of FIG. 24, wherein (a) shows a negative current pulse at 58.8 mA followed by a 400 μs recovery pulse at 14.8 mA, and (b) shows an increased current reference value to generate larger amplitudes.

With the flyback working properly, the buck was added to the setup and the switched capacitor circuit assembled. Waveforms in FIG. 31 show two current pulses generated by the prototype stimulator. The edges of the pulses are sharp and reach the proper proportions in less than 300 ns. The hysteretic control establishes the current level during each phase. The sensed current is on the same level during the whole pulse and is kept tightly regulated within the hysteretic margin $\Delta v\_i_{hysteresis}$. FIG. 31 shows the current pulse waveform with the following parameters: $R_{load}$=1 kΩ, $t_{pulse}$=100 μs, $f_{pulse}$=100 Hz. Ch1: duty cycle signal, 20V/div. Ch2: load sensed current, 5V/div. Ch3: control reference, 5V/div. Ch4: positive terminal of load voltage, 50V/div. wherein FIG. 31a shows the negative current pulse at 58.8 mA followed by 400 µs recovery pulse at 14.8 mA and (b) shows the current reference value increased to generate larger amplitude.

Figure 32:
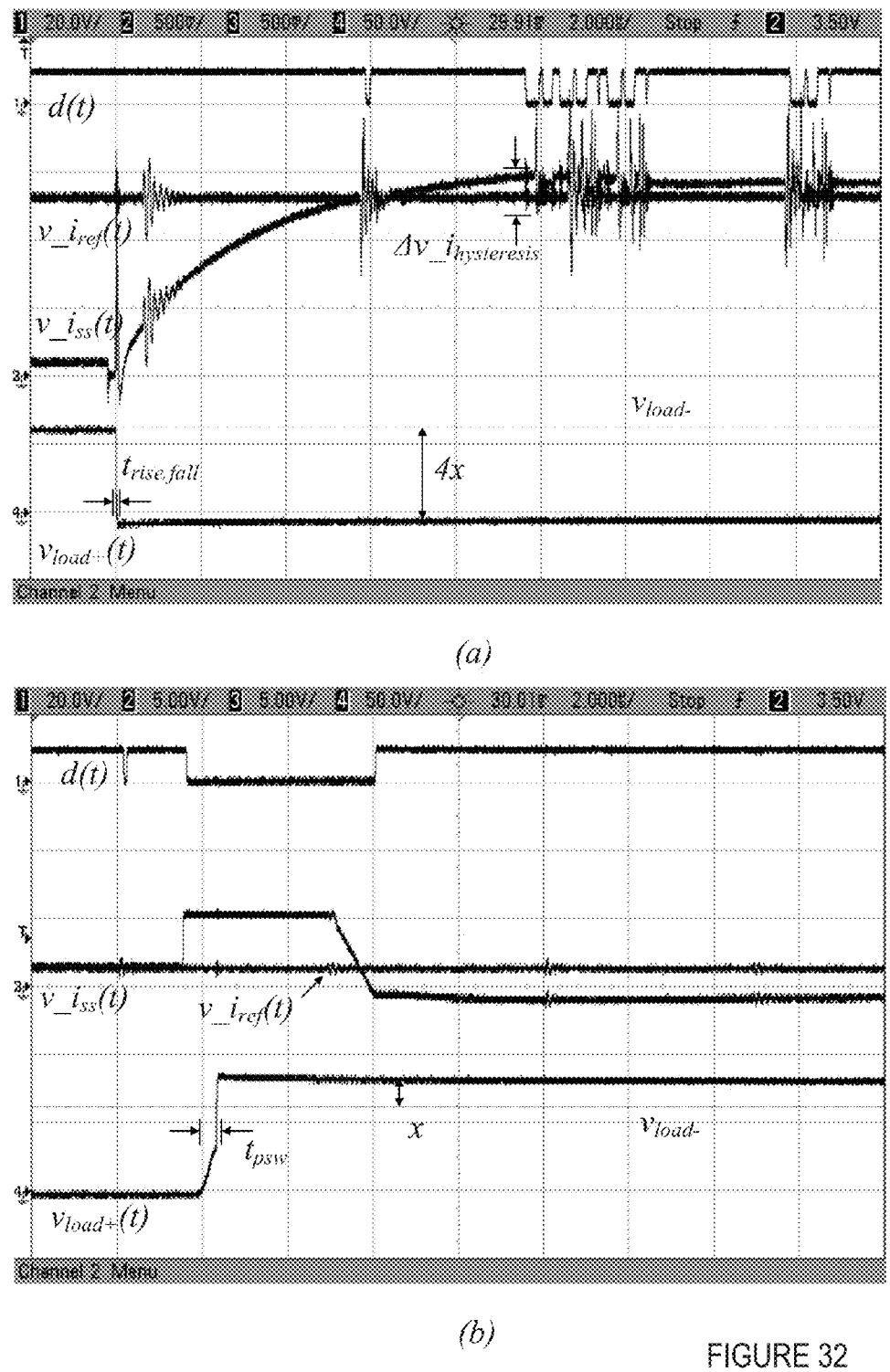
FIG. 32 is a plot of experimental waveforms showing a pulse rise time and pulse direction switching time, in accordance with the embodiment of FIG. 24.

To further validate the experimental design, the current pulse waveform is analyzed for rise time and switch time between phases. FIG. 32 shows the rise time and pulse direction switching time where $R_{load}$=1 kΩ, $t_{pulse}$=100 µs, $f_{pulse}$=100 Hz. Ch1: duty cycle signal, 20V/div. Ch2: load sensed current, 500 mV/div in (a) 5V/div in (b) superimposed on Ch3: control reference, 500 mV/div in (a) 5V/div in (b), Ch4: positive terminal of load voltage, 50V/div., wherein FIG. 32a shows the initial rise/fall time to reach the desired pulse amplitude and wherein FIG. 32b shows the direction and amplitude of current pulse changes from negative to positive.

The load negative terminal voltage is labeled in FIG. 32 as a reference point. The rise time in FIG. 31a is well below the specification at less than 80 ns for a −70 mA pulse. The hysteretic margin, $\Delta v_{hysteresis}$, is clearly shown in the figure and the sensed current takes only 6 µs to reach the reference from zero. The switching time between phases in FIG. 31b is approximately 250 ns for a 90 mA swing to an 18 mA pulse. However, the time between phases can be adjusted by the user for different applications.

The experimental conditions from FIG. 31 are used to assess the power consumption of the prototype and how it relates to prospective operating time as a portable FES unit. The setup uses a 6V source with 650 mA of current. This equates to 3.9 W of power. Commercially available lithium ion batteries are rated at approximately 3.3 Ah. The energy supplied by this battery at 6V can be found in the following.

$$E_{sup} = \text{capacity} \times v_{battery} \times 1\frac{J}{s} \times 3600\frac{s}{h}$$

$$E_{sup} = 3.3 \text{ Ah} \times 6 \text{ V} \times 3600\frac{J}{h}$$

$$E_{sup} = 71.28 \text{ kJ}$$

Now, to find the number of hours of operation, the supplied energy from the battery is divided by the power in J/s needed by the device as shown in the following.

$$T_{operating} = \frac{E_{sup}}{P_{device}} \times \frac{1}{3600}\frac{h}{s}$$

$$T_{operating} = \frac{71.28 \text{ kJ}}{3.9\frac{J}{s}} \times \frac{1}{3600}\frac{h}{s}$$

$$T_{operating} \cong 5.1 \text{ h}$$

It will be appreciated that the use of an external FPGA and discrete components may in fact reduce the efficiency of the system design, which efficiency, when considered in the context of other similar embodiments having dedicated component design and integration, may in fact be higher, thus further increasing the usability of such designs as portable devices.

As shown above, the tested prototype clearly demonstrates the usability of this design, and its equivalents, for various FES applications. Furthermore, experimental waveforms show relatively clean and accurate current pulses with very fast rise time, which attribute may be particularly significant in effectively eliciting action potentials in stimulated tissues, and thus potentially resulting in the use of less current to cause similar contractions as compared to other slower devices, a benefit both in power management and patient safety.

Example 2

This example provides experimental results achieved using a prototype constructed in accordance with the embodiments of FIGS. 5, 11 and 13. Namely, a four channel stimulator was designed to include a) a flyback power stage; b) four (4) stimulation channels each including a buck converter, switched capacitor output circuit and sensing circuitry; and c) a digital block including a controller for the flyback and stimulation channels. The first power stage established a high voltage output that fed into each channel. There the buck converter scaled down the supply voltage to the necessary level. Finally, to construct the output current pulses, the switched capacitor circuit quickly changed the voltage level and current direction. A hysteretic control was used to control the buck duty cycle. The prototype was fabricated using discrete components and a programmable DE-2, FPGA Altera Evaluation Board as a digital block. The converter and output blocks were designed and implemented on a custom PCB. It was determined that the prototype is capable of producing up to 125 mA current with 10 ns rise time for pulses. The duration of the pulses can be varied between 10 µs and 8,000 µs, within a 1 Hz to 10 KHz frequency range.

As will be described in greater detail below, the effectiveness of the herein described output stage architecture, and its various components, was demonstrated with an FPGA-controlled 4-channel system capable of producing up to a 125 mA current with a 10 ns rise time. The duration of the pulses can be varied between 10 µs and 8,000 µs, within a 1 Hz to 10 KHz frequency range.

Figure 33:
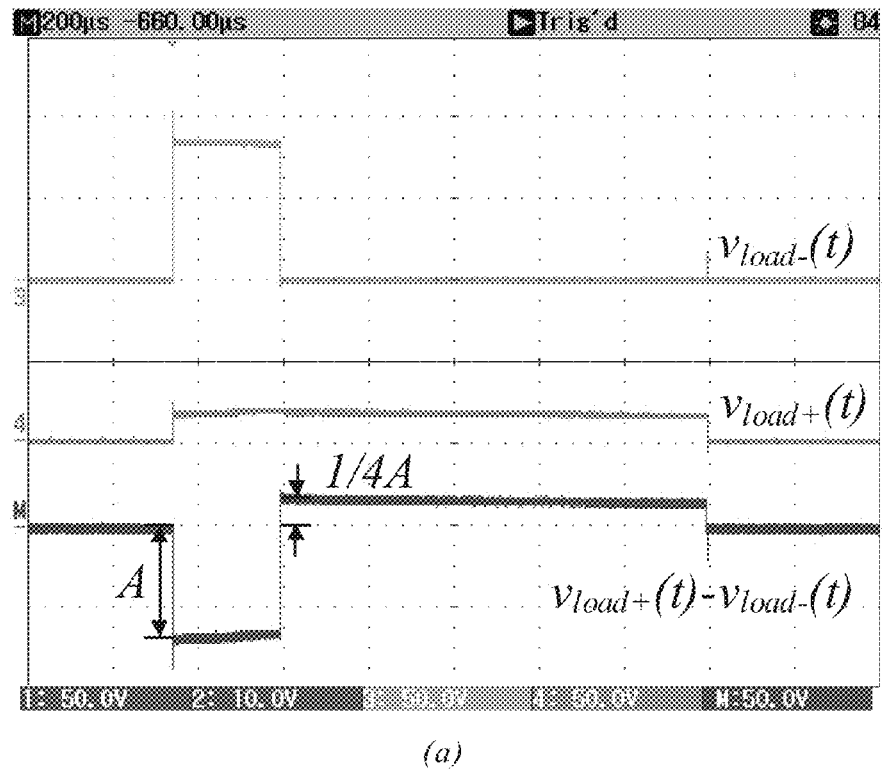
FIG. 33 is a plot of asymmetric bipolar current pulse waveforms where $R_{load}$=1 kΩ, $t_{pulse}$=250 μs (4$t_{pulse}$=1 ms), $f_{pulse}$=40 Hz, and in which plots in (a) represent a −60 mA pulse followed by a +15 mA pulse, and in which plots in (b) represent two stimulation channels firing simultaneously to provide a −30 mA pulse followed by +7.5 mA pulse, in accordance with one embodiment of the invention.
Figure 33:
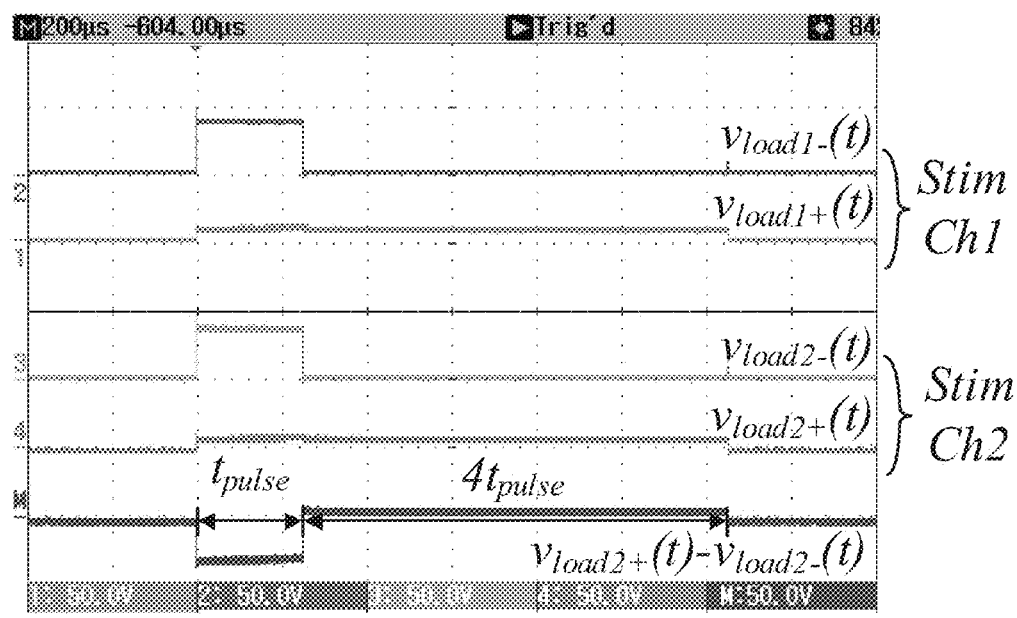

FIG. 33 shows two different current pulses generated by the prototype stimulator. In (a) the amplitude levels of the negative and positive current phases are shown explicitly to show tight regulation over current levels, whereas (b) shows two stimulation channels producing the same regulated current pulse simultaneously. The pulse durations are shown to verify tight control over temporal characteristics.

Figure 34:
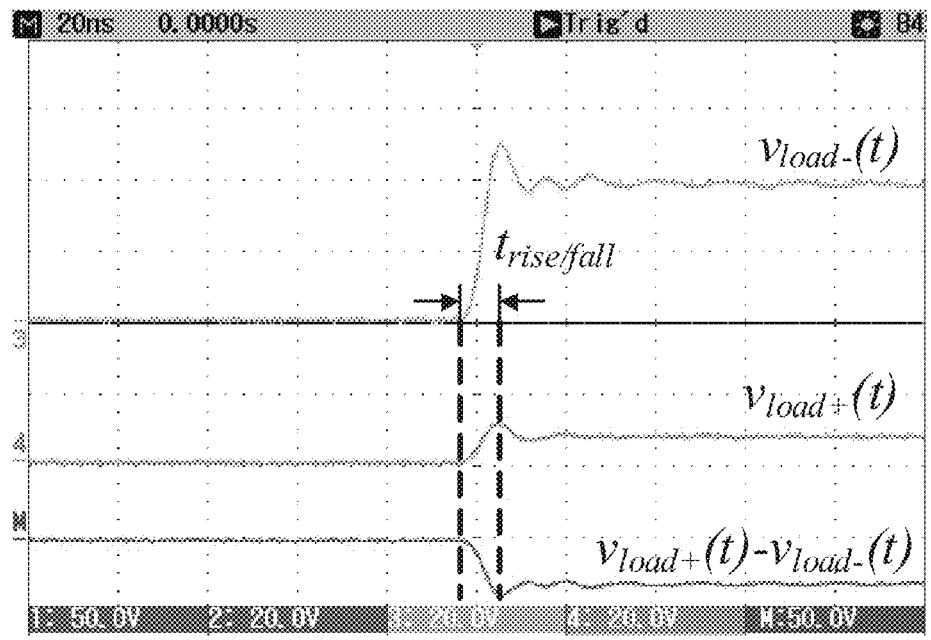
FIG. 34 is a plot of rise time detail where $R_{load}$=1 kΩ, $t_{pulse}$=250 μs, $f_{pulse}$=40 Hz in which (a) an initial rise/fall time to reach a desired pulse amplitude for a −60 mA pulse is shown to be below 10 ns, and in which (b) an initial rise/fall time to reach a desired pulse amplitude for a −30 mA pulse is shown to be below 10 ns, in accordance with the embodiment of FIG. 33.
Figure 34:
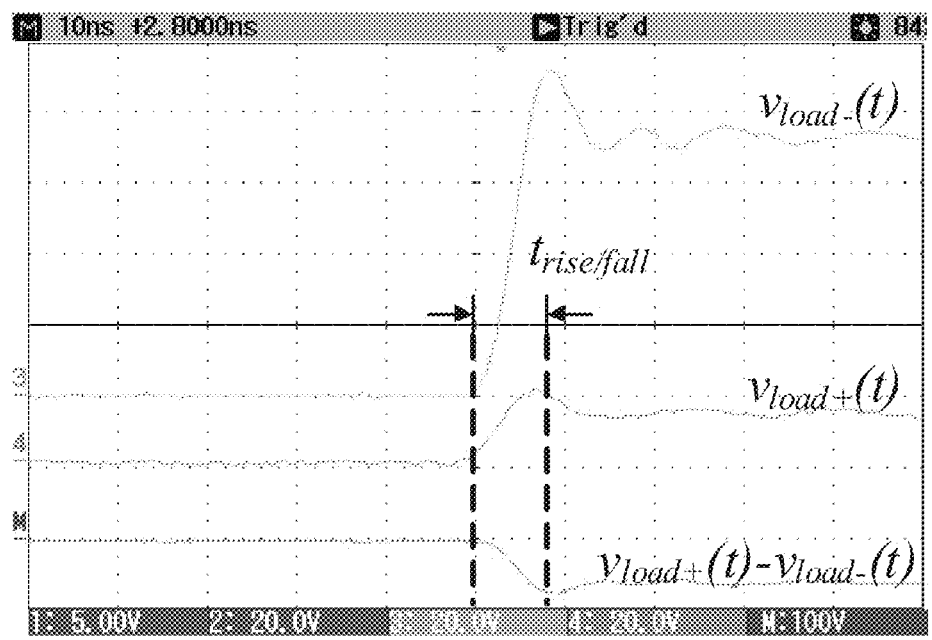

FIG. 34 shows the rise/fall time of two different current pulse waveforms. In (a) the rise time for a −30 mA current pulse is shown to be less than 10 ns while (b) verifies a −60 mA current pulse with the same result.

The experimental conditions from 34b (i.e. Asymmetric, 30 mA, 40 Hz, 250 µs) were used to assess the approximate power consumption of the prototype and how it related to prospective average operating time in a portable FES unit. It will be appreciated that these values provide only an example of potential power consumption values, and that embodiments may be designed and operated to consume more or less energy depending on the FES application at hand and/or various other parameters, as will be readily apparent to the person of ordinary skill in the art. The setup used an 8V source with 300 mA of current, which is equivalent to 2.4 W of power. Commercially available lithium ion batteries are rated at approximately 6 Ah. The energy supplied by this battery at 8V is:

$$E_{sup} = \text{capacity} \times v_{battery} \times 1\frac{J}{s} \times 3600\frac{s}{h}$$

$$E_{sup} = 6 \text{ Ah} \times 8 \text{ V} \times 3600\frac{J}{h}$$

$$E_{sup} = 172.8 \text{ kJ}$$

Now, to find the number of hours of operation, the supplied energy from the battery was divided by the power in J/s needed by the device as shown:

$$T_{operating} = \frac{E_{sup}}{P_{device}} \times \frac{1}{3600} \frac{h}{s}$$

$$T_{operating} = \frac{172.8 \text{ kJ}}{2.9 \frac{J}{s}} \times \frac{1}{3600} \frac{h}{s}$$

$$T_{operating} \cong 16.55 \text{ h}$$

As discussed above, many FES devices have been developed in the past that have proven useful in certain applications, however due to several main limitations, have not been able to address the full potential of emerging stimulation therapy. In these devices, charge balance cannot be ensured over time without extra discharging circuitry because of partial control over temporal characteristics and amplitude. Second, they provide a limited number of pulses and require complicated and costly adjustments for use in different FES applications. Finally, they fail to achieve clean pulse shapes, which is important in minimizing the amount of current needed for stimulation. As a consequence, researchers and practitioners are functionally constrained by these devices as they do not have access to all the different pulses needed for various FES applications.

In comparison, the four channel prototype discussed above provides significant improvements over known devices. For example, all stimulation variable control components can be integrated using a single chip system design; the output stage produces current regulated pulses that have unmatched amplitude, duration, frequency and waveform regulation accuracy; the pulse rise time is several orders of magnitude better than the known designs; charge balancing for bipolar pulses is ensured through the use of the described output circuit; and the operating time is estimated to be much greater than current external FES systems. The proposed systems also generated "clean" pulses, i.e., pulses with very sharp edges and accurate current and duration regulation, which are much better suited for emerging FES applications than previous designs. Furthermore, the pulses of all 4 channels are controlled separately and can be triggered simultaneously, which may allow for real-time stimulation and recording, as generally needed in closed-loop EMG controlled applications, such as neuroprosthesis for grasping.

The above-described prototype features many improvements over previous designs, especially with respect to versatility, efficiency, compactness, and safety. Furthermore, this output stage was also designed having in mind FES applications that require high degree of programmability and versatility. While the above was designed for surface FES applications, the person of ordinary skill in the art will readily appreciate the applicability of the above design to implantable electrical stimulators, particularly in the context of the integrated design architecture considered in the illustrative embodiment described above, which may have advantages in providing for a reduction in the number of parts and energy consumption, for example.

Example 3

This example provides results an exemplary FES therapy process for improving brain and associated muscle function in individuals suffering from a neuromuscular deficit, which process provides an example only of the various FES applications, methods and treatments that may be facilitated by the above-described FES devices and systems. In this example, the individual was suffering from the neurological disorder following a stroke. It will be appreciated that this kind of neurological disorder of the central nervous system may have resulted from stroke, spinal cord injury, brain injury, multiple sclerosis, and any other injury both traumatic and non-traumatic to the central nervous system, for example.

Individual Description

The individual was a 22-year-old woman who suffered a hemorrhagic stroke in the right frontal parietal area two years prior to the participation in this study. The individual presented at an individual rehabilitation centre with motor recovery status scored by CMSMR (Chedoke McMaster Stages of Motor Recovery) as follows: arm=1, hand=2, leg=2, and foot=2. After four months of rehabilitation, the CMSMR scores were as follows: arm=2, hand=2, leg=4, and foot=2. While left leg showed some recovery, the left arm was not functional. At the beginning of the FES-mediated protocol, the individual was independent in activities of daily living with the help of cane and ankle-foot orthosis, but reported that she rarely, if ever, used her paretic upper limb. Movement of the upper extremity was characterized by a flexor synergy pattern. The individual had increased resistance to passive stretching in the distal flexor musculature. Tactile sensation was shown not to be severely impaired throughout the upper limb by the use of the two point discrimination test. Stroke patients, such as the individual of the instant study, are considered neurologically stable and do not show any signs of further improvement 24 months following stroke. Therefore, the individual recruited to this study was in the chronic phase of injury, 24 months post stroke, was severely disable as measured by CMSMR and was not expected to improve regardless which therapy is provided to her.

Functional Electrical Stimulation Therapy—

An FES-mediated protocol was delivered by way of an electric stimulator (electrical stimulator used was a prototype of the electrical stimulator discussed above), with standard self-adhesive surface stimulation electrodes. In the study the following muscles were stimulated with the surface stimulation electrodes (the locations of the electrodes for each muscle are shown in the FIG. 35B): anterior (aDel) and posterior deltoid (pDel), biceps brachialis (BB) and triceps brachialis (TB), extensor carpi radialis, extensor carpi ulnaris, flexor carpi radialis, and flexor carpi ulnaris. Stimulus parameters used to stimulate the nerves that are innervating the muscles of interest were asymmetric bipolar current pulses with the pulse duration of 250 μsec and frequency 40 Hz. During the protocol the stimulus was delivered to the muscles of the paralyzed limb in such a way that these muscles produced movements that accurately mimicked the movements that the brain would produced if the patient were not paralyzed. When the stimulus was delivered to the muscles, it was gradually increased or decreased (instead of being delivered instantaneously) using ramp up and ramp down functions lasting from 0.5 to 2 seconds. The therapist used a hand switch to trigger stimulation when he determined that the individual needed assistance with the task.

FES-Mediated Protocol—

Figure 35A:
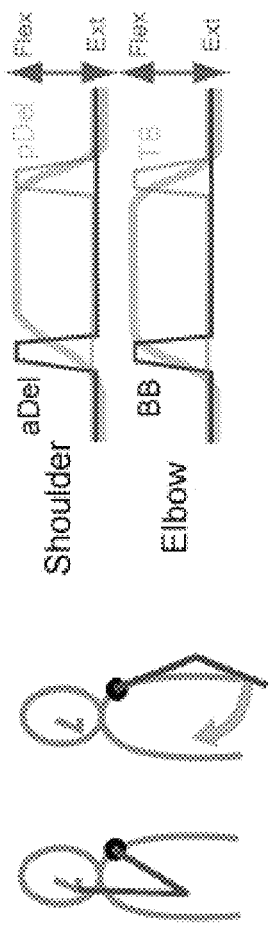
FIG. 35A is a schematic picture of functional motion tasks conducted, and of shoulder and elbow joint angle changes and stimulus pattern of each muscle where thick and thin lines indicate joint motion and stimulus pattern (timing of ON/OFF)
Figure 35A:
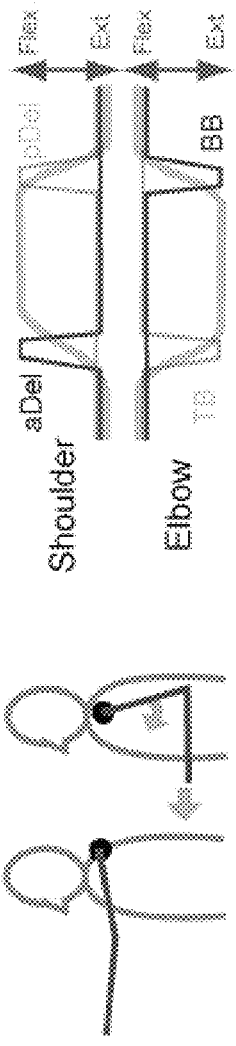
Figure 35A:
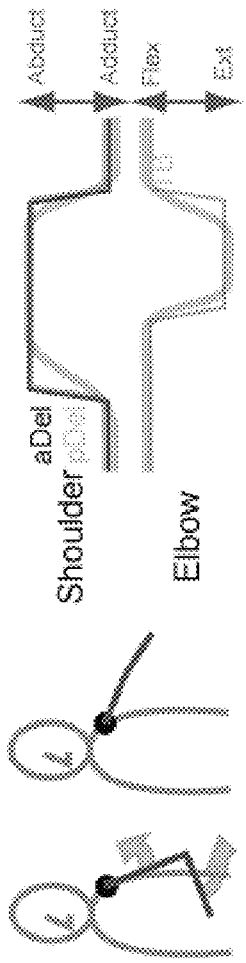
Figure 35B:
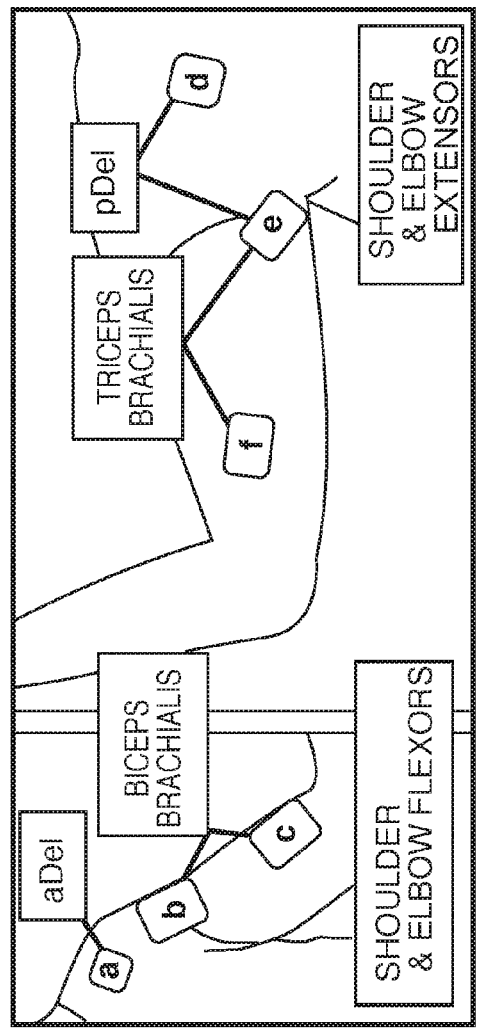
FIG. 35B is a schematic depiction of electrode locations.
Figure 35B:
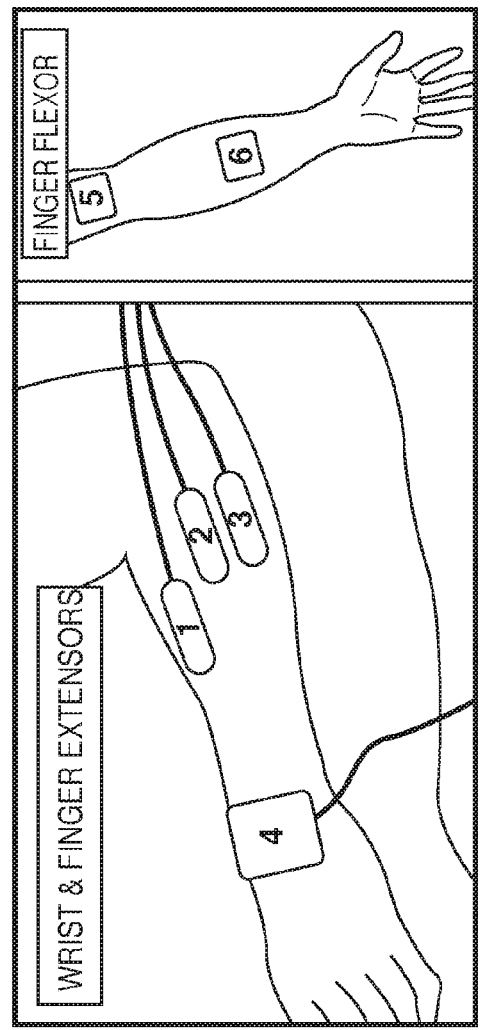

Briefly, the FES-mediated protocol consisted of pre-programmed coordinate muscular stimulation and manual assisted (externally generated) passive motion to establish physiologically correct movement. During the movement, the individual was asked to imagine the movements and to try to carry it out herself. At the beginning of the study the patient was unable to move the arm voluntarily and therefore was not able to physically execute voluntarily imagined movements. As shown in FIG. 35A, the FES was delivered to shoulder, elbow, wrist and finger extensor and flexor muscles, while the individual (assisted by the therapist) performed the following types of motions: (1) touch nose, (2) touch shoulder, (3) move arm forward, (4) lift arm left side up, (5) reach and grasp large objects, (6) reach and grasp small objects, (7) manipulate objects during grasp, and (8) place the object at a designated location and release the object. The FES-mediated protocol was carried out for an hour. The protocol, at a minimum, comprises 40 one-hour sessions wherein at least 3 one-hour sessions are delivered per week, however the protocol may be repeated more frequently, if desired. In case of the individual of the instant example, the protocol was preformed twice daily. In individuals who have suffered a stroke, the neuromuscular recovery typically starts proximally followed by the recovery of the distal neuromuscular compartments. Therefore, the FES-mediated protocol began by training shoulder and upper arm muscles first, followed by writs and fingers training.

TABLE 2

Upper limb motion tasks, types of motion, and electrodes used for in each task. The alphabetical characters and numbers in this figure match to those in the FIG. 35B

| SHOULDER & ELBOW MOTION | | | | |
|---|---|---|---|---|
| Task | Shoulder motion | (Electrode) | Elbow motion | (Electrode) |
| Touch nose | Flexion | a-b | Flexion | b-c |
| Touch shoulder | Flexion&Int. rotation | a-b | Flexion | b-c |
| Swing forward | Extension | d-e | Extension | e-f |
| Left side up | Abduction | a-b & d-e | Extension | e-f |

| WRIST & HAND MOTION | | |
|---|---|---|
| Task | Target motion | (Electrode) |
| Bottle grasping | Wrist extension & full finger open | 1-4, 2-4 & 3-4 |
|  | Finger flexion | 5-6 |
| Small object picking | Two finger (thumb & index) open | 1-4 |

During the FES-mediated protocol, a therapist controlled/triggered the arm movements using a pushbutton. During the movements, the physiotherapist guided the arm and assisted the individual with the neuroprosthesis in performing the desired task. This assistance provided that all movements were carried out in a correct physiological way, i.e., neuroprosthesis induced movements did not oppose natural joint movements and respected the anatomy of bone and soft tissue composition. In the early stages of the treatment, the arm tasks were performed by the combination of muscular stimulation and therapist's assistance. As the individual improved, the assistance was reduced to the necessary minimum. Typically, the stimulation protocols were adjusted weekly or biweekly. The individual was asked to repeat the same arm task 10 times for each motion during a single treatment session. The treatment sessions lasted up to 60 minutes.

Outcome Measures—Clinical assessments:

CMSMR and Motricity Index tests for the upper limb were used to assess the arm and hand functions. The degree of spasticity in the affected upper limb was evaluated using the five-grade Modified Ashworth Scale (MAS).

H-Reflex and M Max:

To assess the excitability of the spinal motoneuron pool in the flexor carpi radialis (FCR) muscle, the Hoffman reflex (H-reflex) was elicited. The H-reflex was evoked by stimulation of the left median nerve with a monopolar electrode placed in the inside of cubital joint. A rectangular pulse (1 ms) was generated by a constant voltage stimulator (DPS-007, Dia Medical System Co., Japan) that was triggered once every 5 s.

Maximal Voluntary Contraction (MVC):

The electromyographic (EMG) signals in the following paralyzed upper arm muscles were detected by a bipolar differential amplifier (Bortec AMT-8; Bortec Biomedical, Canada): aDel, pDel, BB, TB, flexor capiradialis (FCR), extensor digitrum longus (EDL), and first distal interosseous muscles (FDI). A pair of surface electrode (BiPole; Bortec Biomedical, Canada) was placed along the muscle fibers over the belly in each muscle with an inter-electrode distance (center to center) of 10 mm. The recorded EMG signals were amplified 500 times and digitized at a sampling rate of 1,000 Hz over a period of 500 ms before and 500 ms after the onset of the movement.

Active Range of Motion Test:

The individual was asked to move her arm toward following five directions as much as she could: (1) forward, (2) backward, (3) upward, (4) right side, and (5) left side. During the movements, we recorded the position of the shoulder, elbow, and wrist joints, and the second joint of index finger. The individual did three trials for each of the five movements.

Circle Drawing Test:

This test was aimed to assess the ability to coordinate shoulder and elbow joints. During circle drawing, the subject requires the ability to coordinate shoulder and elbow movements. Specifically for individuals whom have suffered a stroke who have spasm in their elbow joint it is not easy to draw a wide and a properly shaped circle. The position of the shoulder, elbow, and wrist joints, and the second joint of index finger while the individual drew the circle on a table was recorded. During the assessment the movements were self-paced, and the task continued for 30 seconds.

Originally, it was planned to assess the individual using tests 1 through 3. However, during the first 6 weeks of training the individual surprisingly showed remarkable improvement of her shoulder and elbow function, thereby prompting the addition of tests 4 and 5 to further evaluate functional motion of the upper limb.

Results

Figure 37:
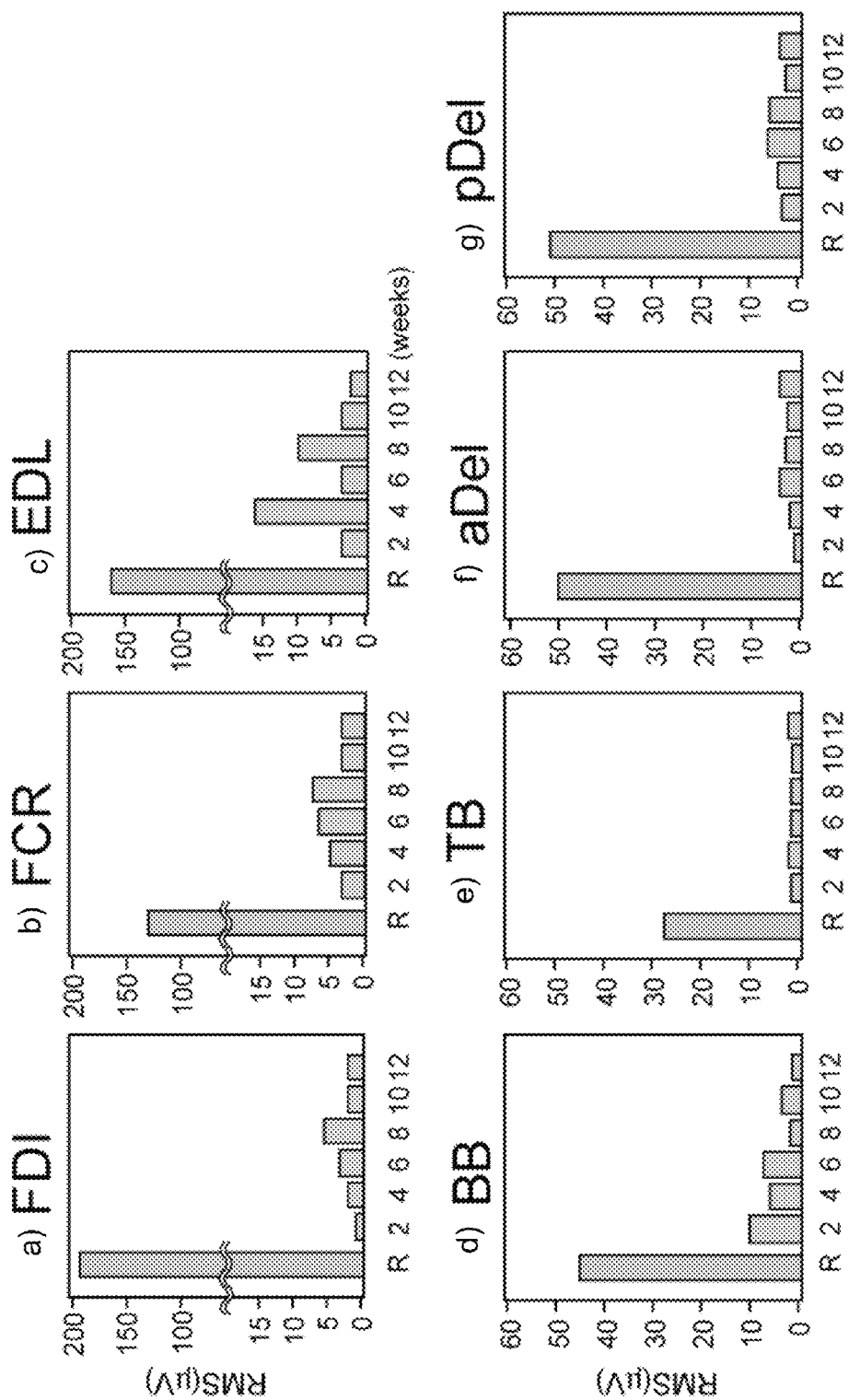
FIG. 37 is a graph of a time course showing changes of a maximal voluntary contraction level of the first distal interosseous muscles (FDI) (a), flexor capi radialis (FCR) (b), extensor digitorum (EDL) (c), biceps brachialis (BB) (d), triceps brachialis (TB) (e), anterior (aDel) (f) and posterior deltoid (pDel) (g) muscles compared to the unaffected side arm as a reference.

The individual successfully completed all training sessions and assessments. Following 12 weeks of FES-mediated protocol, the individual was able to pick a thin object, touch her nose and draw circles, for example, tasks which could not be accomplished prior to the FES-mediated protocol sessions. As the clinical measures selected, namely the CMSMR and Motricity Index tests are coarse measures, these tests did not show changes in the scores following the 12-week protocol. However, the MAS of the hand and wrist showed reduction in spasticity over the course of the training (wrist: 3 to 2, hand: 4 to 3). H-reflex, which reflects the spinal motoneuron excitability, also showed remarkable reduction with training (FIGS. 36a, 36b and 36c). Namely, the size of the H-reflex was quite high at the beginning of the protocol (82.09% Mmax) and as the time passed it decreased considerably (53.65% in 6$^{th}$ week and 45.04% in 12$^{th}$ week), indicating that the high tone which is commonly associated with the damaged to the supra spinal compartments of the central nervous system is reverting, and that the central nervous system function is returning back to its normal levels of tone and reflex responses. FIG. 37 shows the changes in the MVC in the upper arm muscles obtained every two weeks. The MVC levels in all muscles measured were at "zero" during the baseline assessment. In other words, the patient was unable to activate a single muscle in the affected arm voluntarily. As the protocol progressed the patient gained ability to voluntarily activate the muscles and further improved with continuation of the protocol. It is worth mentioning that the MVC levels in the affected arm were remarkably smaller than that of the unaffected arm. However, even the low levels of MVCs were sufficient to allow the patient to effectively and voluntarily move the arm and fingers to reach and grasp objects. A good example of the muscles which showed considerable improvement following the FES-mediated protocol are the FDI and TB muscles, which did not show any EMG (RMS μV) activity at the baseline and following the FES-mediated protocol showed remarkable improvements in voluntary EMG and muscle contraction control. Table 3 shows the shoulder and elbow dynamic range of motion. It is clearly shown that the value of dynamic range of motion for the shoulder and elbow joint at week 12 showed remarkable improvement as compared to those measured at week 6. At week 0 the individual did not have any voluntary movement in the affected arm. Therefore, transformation from no movement in week 0, to restricted movement in week 6 followed by much more expanded range of motion in week 12 is a remarkable change. Given that the individual of this study was in the chronic injury phase, as noted above, and therefore not expected to show improvement regardless whether any intervention was provided, the changes observed and noted herein are remarkable. Furthermore, such changes have not been previously observed in chronic severe stroke patients.

the protocol progressed. At week 0 the individual do not have any voluntary movement in the affected arm and was unable to drawn circles.

The purpose of this study was to assess the effect of 12 weeks intensive FES-mediated protocol on a chronic severe stroke individual (CMSMR score 2 or less). Although motor capacity score, i.e., CMSMR and MVC tests did not show any significant changes, due to the courses of the tests, the MAS and the amplitude of H-reflex were reduced as the result of the FES-mediated protocol. Additionally, the kinematic results showed a profound improvement in the ability to perform arm movements and to coordinate shoulder and elbow joints. These results suggest that the improvement of the upper arm functional motion can be attributed to retraining of the central nervous systems through means of neuroplasticity, which is observed in improvement of the upper limb voluntary motor function as well as the reduction of muscle tone and/or spasticity.

Traditionally neuromuscular electrical stimulation has been used to increase strength of the voluntary muscle contractions in various neurological patients and healthy individuals. But recent applications of electrical stimulation are shifting the focus from muscle strengthening towards re-training the central nervous system and improving motor control of the stroke individuals. In this study, FES-mediated protocol was used to retrain a chronic stroke individual to voluntarily perform coordinated multi-joint movements with the arm that was previously paralyzed as a result of stroke. Since the stimulus intensity we used was approximately two times larger than the motor threshold, one could not expect that the FES-mediated protocol generated changes in muscular function due to an associated increase in muscle strength. This assumption was confirmed by the results shown in the FIG. 37, that is, there were no consistent changes of the MVC in the upper limb muscles.

At the beginning of the FES-mediated protocol, the individual's upper limb had high muscle tone. However, the muscle tone of wrist and elbow flexors was remarkably decreased as the result of the FES-mediated protocol, which was clearly reflected by the results of MAS (Table 2) and

TABLE 3

Dynamic range of motion (rom) of the shoulder and elbow joints.

| | Shoulder | | | | | | | | Elbow | |
|---|---|---|---|---|---|---|---|---|---|---|
| | Flexion | | Abduction | | Int. rotation | | Ext. rotation | | Extention | |
| Direction of Motion | 6th wk (deg) | 12th wk (deg) | 6th wk (deg) | 12th wk (deg) | 6th wk (deg) | 12th wk (deg) | 6th wk (deg) | 12th wk (deg) | 6th wk (deg) | 12th wk (deg) |
| Forward | 19.82 | 28.77 | 31.25 | 31.77 | | | | | 74.90 | 75.36 |
| Upward | 34.81 | 44.25 | 55.22 | 62.63 | | | | | 100.78 | 112.67 |
| Left side | | | 32.51 | 40.47 | | | 22.74 | 31.84 | | |
| Right side | 52.19 | 47.35 | | | 83.47 | 108.70 | | | | |

Figure 38A:
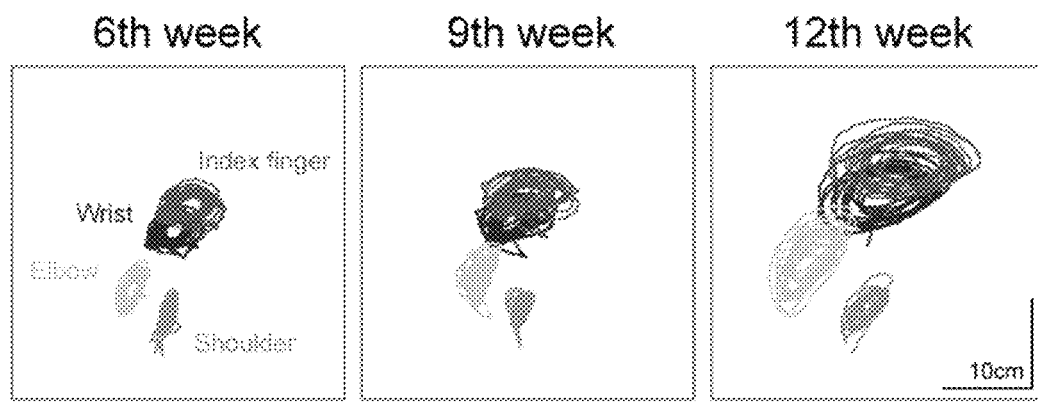
FIG. 38A is an exemplary x-y plot of the absolute positions of the shoulder, elbow, wrist joint, and index finger position during a circle drawing test.
Figure 38B:
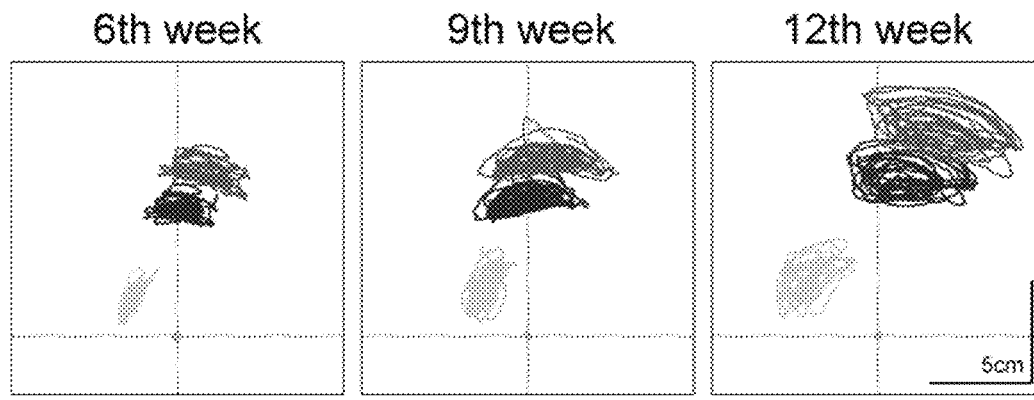
FIG. 38B is an exemplary x-y plot of the positions of the elbow, wrist joint, and index finger position during a circle drawing test normalized to the shoulder position.

FIG. 38a shows the x-y plot of the shoulder, elbow, wrist, and index finger positions while the individual was performing circle drawing test. The absolute coordinates of individual joints were represented in the upper three figures in FIG. 38a. The joints and index finger coordinates with respect to the shoulder joint coordinate frame (i.e., assuming that the reference coordinate frame is in the shoulder joint) are shown in the bottom three figures in FIG. 38b. While the size of drawn circle by the index finger was small at the 6$^{th}$ week of the FES-mediated protocol, its size became larger as H-reflex (FIG. 37). This result was in good agreement with the previous findings that describe the effects of the electrical stimulation on the reduction of the abnormally high muscle tone. It should be noted that the resting condition of the individual's arm, specifically hand, was drastically changed with the time course of training. Namely, the individual was able to relax her hand and keep the hand relaxed during reaching motion. Therefore, the improvement of the upper arm functional motion can be partly attributed to the reduction of muscle tone and/or spasticity. This finding supports the classical concept that muscle tone reduction represents simplistic solutions to the deficit in motor control after stroke.

Pre-programmed stimulus patterns were developed that are able to generate variety of upper limb movements/functions. The temporal activations of the muscles induced by the FES were similar to those of intact neuromuscular system that is performing the same task, i.e., the muscle activations were designed to clone actual natural movements. Thus, during the movements the individual could feel when she was supposed to activate muscle contractions and how to sequence them to produce desired movements. The fact that marked changes in the H-reflex were observed and that a number of muscles that the individual was unable to voluntarily contract prior to the FES-mediated protocol were under her voluntary control at the end of the protocol suggests that the functional improvements induced by the FES-mediated protocol are in part due to changes that occur in the central nervous system. In other words, the intensive, repetitive and yet diverse FES-mediated protocol may be promoting plastic reorganization of the central nervous system. Therefore it is predicted that the following mechanism may cause the changes observed. If a hemiplegic individual who strains to execute a task is assisted with the FES to carry out that same task, he/she is effectively voluntarily generating the motor command (desire to move the arm, i.e., efferent motor command) and the FES is providing the afferent feedbacks (afferent sensory input), indicating that the command was executed successfully. Therefore, it is believed that by providing both the motor command and sensory input to the central nervous system repetitively for prolonged periods of time, this type of FES-mediated protocol facilitates functional reorganization and retraining of intact parts of the of central nervous system and allows them to take over the function of the damaged part of the central nervous system. As the individual continues to improve the voluntary function then the volitional-related sensory feedback from the stimulated muscles and arm further contributes to this retraining process. This is possible due to the distributed nature of the central nervous system and the fact that various parts of the brain are responsible for processing similar tasks. For example, motor tasks are typically associated with motor and pre-motor cortex activity. However, the motor tasks are also processed in the occipital lobe. Therefore, FES-mediated protocol is allowing the central nervous system to access such distributed networks and used them to help patient relearn new motor tasks, lost due to injury or disease of the central nervous system.

The present exemplary FES-mediated study may confirm that the FES-mediated protocol can be used to improve the upper limb functions in chronic stroke individuals. Furthermore, as this type of protocol may be effective in individuals with severe upper limb impairment, it is very likely that it is effective in individuals with less severe upper limb disability. The exemplary study investigated on weekly basis how the H-reflex and the EMGs of various muscles changed over time due to FES-mediated protocol. The key finding is that the muscles that were paralyzed prior to the study became active and were under voluntary control of the individual after the FES-mediated protocol. Furthermore, the H-reflex decreased almost 50% after the FES-mediated protocol was completed suggesting a significant reduction in muscle tone and/or spasticity as a result of this exemplary FES-mediated protocol.

While the present disclosure describes various exemplary embodiments, the disclosure is not so limited. To the contrary, the disclosure is intended to cover various modifications and equivalent arrangements included within the spirit and scope of the appended claims. The scope of the following claims is to be accorded the broadest interpretation so as to encompass all such modifications and equivalent structures and functions.

The invention claimed is:

1. An electrical stimulation device for providing sequential bipolar pulse stimulation to an area of a living body via one or more electrode leads applied to the area, comprising:
a substantially constant voltage supply;
a current pulse generating circuit comprising output nodes for operative coupling to the one or more electrode leads, and configured for operative coupling to the substantially constant voltage supply, said current pulse generating circuit comprising positive and negative stimulation paths drawing from said substantially constant voltage supply to respectively apply positive and negative currents through the area via the one or more electrode leads, said stimulation paths comprising respective capacitive elements, wherein periodic alternative activation of said stimulation paths provides the sequential bipolar pulse stimulation, said stimulation paths comprising a positive stimulation loop and a negative stimulation loop, each one of which serially encompassing said output nodes, drawing from said substantially constant voltage supply, and comprising respective loop activation switches and said respective capacitive elements, wherein a capacitance ratio of said capacitive elements dictates, at least in part, an amplitude ratio of said positive and negative currents, the electrical stimulation device further comprising a controller configured for alternatively activating said loop activation switches to provide negative and positive current pulses, a duration ratio of which being inversely proportional to said capacitance ratio.

2. The electrical stimulation device of claim 1, wherein at least one of said respective capacitive elements comprises two or more serially connected capacitive elements, at least one of which being selectively activated during operation to modify a combined capacitance thereof thereby adjusting said capacitance ratio.

3. The electrical stimulation device of claim 2, wherein adjustment of said capacitance ratio provides for selection between symmetric and asymmetric pulse stimulation.

4. The electrical stimulation device of claim 1, wherein a charge applied to the area via the bipolar stimulation is substantially balanced by each sequential pair of said negative and positive currents.

5. The electrical stimulation device of claim 1, wherein at least one of said respective capacitive elements is disposed in series with the stimulated area during activation of each of said stimulation paths, thereby reducing charge accumulation in the stimulated area during operation.

6. The electrical stimulation device of claim 1, wherein a pulse rise time of said pulse stimulation is predominantly dictated by a switching speed of said respective loop activation switches.

7. The electrical stimulation device of claim 1, further comprising a dual stage switched mode power supply (SMPS) said dual stage SMPS comprising a flyback converter operatively coupled to a power source, and a buck converter operatively coupled thereto to adjust said voltage supply in regulating pulse current amplitudes available through said current pulse generating circuit.

8. The electrical stimulation device of claim 1, wherein the current pulses are provided at a frequency of about 40 Hz.

9. The electrical stimulation device of claim 1, wherein each of the current pulses are applied for about 250 μsec.

10. The electrical stimulation device of claim 1, wherein said pulse rise time is no greater than 500 ns.

11. The electrical stimulation device of claim 1, wherein said pulse rise time is no greater than 100 ns.

12. The electrical stimulation device of claim 1, wherein said pulse rise time is no greater than 20 ns.

13. The electrical stimulation device of claim 1, wherein said pulse rise time is no greater than 10 ns.

14. Use of the electrical stimulation device of claim 1 for providing functional electrical stimulation for improving one or more of muscle, associated nerve, brain and spinal cord function in individuals suffering from a neuromuscular deficit, stroke, multiple sclerosis, spinal cord injury, central nervous system injury or a muscular injury.

15. Use of the electrical stimulation device of claim 1 for providing functional electrical stimulation to a plurality of associated nerves capable of communicating therebetween, so as to encourage communication amongst said nerves.

16. The use as defined in claim 15, wherein the functional electrical stimulation is applied at an intensity of from about a multiple of the motor unit activation threshold to about three times the motor unit activation threshold.

17. The use as defined in claim 16 wherein the functional electrical stimulation is applied at an intensity of about two times the motor unit activation threshold.

18. The use as defined in claim 15, wherein over time a communicative interconnectivity between the nerves improves.

* * * * *